(12) United States Patent
Wu et al.

(10) Patent No.: US 11,866,487 B2
(45) Date of Patent: Jan. 9, 2024

(54) FILAMIN A BINDING PROTEINS AND USES THEREOF

(71) Applicant: BPGbio, Inc., Framingham, MA (US)

(72) Inventors: Wenfang Sybil Wu, Wayland, MA (US); Shobha Ravipaty, Framingham, MA (US); Tracey Friss, Holliston, MA (US); Viatcheslav R. Akmaev, Sudbury, MA (US); Nikunj Narendra Tanna, Belmont, MA (US)

(73) Assignee: BPGbio, Inc., Framingham, MA (US)

( * ) Notice: Subject to any disclaimer, the term of this patent is extended or adjusted under 35 U.S.C. 154(b) by 438 days.

(21) Appl. No.: 16/935,596

(22) Filed: Jul. 22, 2020

(65) Prior Publication Data
US 2021/0139570 A1    May 13, 2021

Related U.S. Application Data

(62) Division of application No. 15/801,093, filed on Nov. 1, 2017, now Pat. No. 10,759,850.
(60) Provisional application No. 62/415,893, filed on Nov. 1, 2016.

(51) Int. Cl.
| | | |
|---|---|---|
| *C07K 16/18* | (2006.01) | |
| *C07K 16/30* | (2006.01) | |
| *G01N 23/2258* | (2018.01) | |
| *G01N 3/50* | (2006.01) | |
| *G01N 27/623* | (2021.01) | |
| *G01N 33/574* | (2006.01) | |
| *A01K 67/027* | (2006.01) | |
| *G01N 33/68* | (2006.01) | |

(52) U.S. Cl.
CPC .......... *C07K 16/18* (2013.01); *A01K 67/0275* (2013.01); *C07K 16/3069* (2013.01); *G01N 3/50* (2013.01); *G01N 33/57434* (2013.01); *A01K 2217/05* (2013.01); *A01K 2227/105* (2013.01); *C07K 2317/21* (2013.01); *C07K 2317/56* (2013.01); *C07K 2317/565* (2013.01); *C07K 2317/92* (2013.01); *G01N 27/623* (2021.01); *G01N 33/6848* (2013.01); *G01N 2333/47* (2013.01); *G01N 2333/4742* (2013.01); *G01N 2333/96455* (2013.01)

(58) Field of Classification Search
CPC .......... G01N 2333/47; G01N 33/6848; G01N 33/6851; G01N 23/2258; C07K 16/18; C07K 2317/21; C07K 2317/56; C07K 2317/565; C12Q 1/6872

See application file for complete search history.

(56) References Cited

U.S. PATENT DOCUMENTS

| | | | |
|---|---|---|---|
| 10,759,850 B2 | 9/2020 | Wu et al. | |
| 2005/0153311 A1 | 7/2005 | Nelson et al. | |
| 2006/0063214 A1 * | 3/2006 | Alper | G01N 33/57415 435/7.23 |
| 2012/0171782 A1 | 7/2012 | Nelson et al. | |
| 2012/0294861 A1 | 11/2012 | Sonoda et al. | |
| 2014/0178391 A1 | 6/2014 | Domon et al. | |
| 2016/0258958 A1 | 9/2016 | Narain et al. | |

FOREIGN PATENT DOCUMENTS

| | | | |
|---|---|---|---|
| WO | WO-2013019634 A1 * | 2/2013 | ........... C07K 14/705 |
| WO | WO-2016196522 A1 * | 12/2016 | ............... C12Q 1/68 |

OTHER PUBLICATIONS

Lin et al . . . J Proteome Res., 2013, 12:5996-6003.*
Van Platerink et al., J Chromatography B, 2006, 830:151-157.*
Bedolla et al., Nuclear versus cytoplasmic localization of filamin A in prostate cancer: immunohistochemical correlation with metastases. Clin Cancer Res. Feb. 1, 2009;15(3):788-96.
Bendig et al., Humanization of Rodent Monoclonal Antibodies by CDR Grafting Methods: A Companion to Methods in Enzymology. 1995,8:83-93.
Colman, Effects of amino acid sequence changes on antibody-antigen interactions. Res Immunol. Jan. 1994;145 (1):33-6.
Khantasup et al., Design and Generation of Humanized Single-chain Fv Derived from Mouse Hybridoma for Potential Targeting Application. Monoclon Antib Immunodiagn Immunother. Dec. 2015;34(6):404-17.
Krastins et al., Rapid development of sensitive, high-throughput, quantitative and highly selective mass spectrometric targeted immunoassays for clinically important proteins in human plasma and serum. Clin Biochem. Apr. 2013;46(6):399-410.
Lin et al., Comparison of protein immunoprecipitation-multiple reaction monitoring with ELISA for assay of biomarker candidates in plasma. J Proteome Res. Dec. 6, 2013;12(12):5996-6003.
Paul, Fundamental Immunology, Third Edition. Raven Press, New York. pp. 292-295, (1993).
Ravipaty et al., Clinical Validation of a Serum Protein Panel (FLNA, FLNB and KRT19) for Diagnosis of Prostate Cancer. Journal of Molecular Biomarkers & Diagnosis. 2017;8(2):1-8.
Rudikoff et al., Single amino acid substitution altering antigen-binding specificity. Proc Natl Acad Sci U S A. Mar. 1982;79(6):1979-83.
Van Der Flier et al., Structural and functional aspects of filamins. Biochim Biophys Acta. Apr. 23, 2001;1538 (2-3):99-117.

(Continued)

*Primary Examiner* — Hong Sang
(74) *Attorney, Agent, or Firm* — McCarter & English, LLP; Jill Mello

(57) ABSTRACT

The present invention encompasses filamin A (FLNA) binding proteins. Specifically, the invention relates to antibodies to FLNA. An antibody of the invention can be a full-length antibody or an antigen-binding portion thereof. Methods of making and methods of using the antibodies of the invention in methods of diagnosis, monitoring and prognosis of prostate cancer are also provided.

11 Claims, 11 Drawing Sheets

Specification includes a Sequence Listing.

(56) References Cited

OTHER PUBLICATIONS

International Search Report and Written Opinion for Application No. PCT/US2017/059573, dated Feb. 26, 2018. 19 pages.

* cited by examiner

Clone 2C12

Clone 3F4

Clone 6E3

FILAMIN A BINDING PROTEINS AND USES THEREOF

RELATED APPLICATION

This application is a continuation of U.S. application Ser. No. 15/801,093, filed on Nov. 1, 2017, pending, which claims priority to U.S. provisional application No. 62/415,893, filed on Nov. 1, 2016. The entire contents of the foregoing application are incorporated herein by reference.

SEQUENCE LISTING

This specification incorporates by reference the Sequence Listing submitted via EFS web identified as 119992_12703_seqlist.txt, which is 153,629 bytes, and was created on Jul. 15, 2023. The Sequence Listing, electronically filed, does not extend beyond the scope of the specification and does not contain new matter.

FIELD OF THE INVENTION

The present invention relates to filamin A (FLNA) binding proteins and their use in the diagnosis, monitoring and prognosis of cancers, including prostate cancer.

BACKGROUND OF THE INVENTION

Prostate cancer is a form of cancer that develops in the prostate, a gland in the male reproductive system. Most prostate cancers are slow growing. However, there are cases of aggressive prostate cancers. The cancer cells may metastasize from the prostate to other parts of the body, particularly to the bones and lymph nodes. Prostate cancer may cause pain, difficulty in urinating, problems during sexual intercourse, or erectile dysfunction. Other symptoms can potentially develop during later stages of the disease.

Rates of detection of prostate cancers vary widely across the world, with detection rates in south and east Asia being lower than those in Europe, and especially in the United States. Prostate cancer tends to develop in men over the age of fifty and, although it is one of the most prevalent types of cancer in men, many never have symptoms or undergo therapy for prostate cancer, and eventually die of other causes. Further, treatment of prostate cancer may do more harm to the subject than the prostate cancer itself. Prostate specific antigen (PSA) screening has led to a significant rise in the number of men diagnosed with prostate cancer with an associated increase in potentially unnecessary biopsies preformed. Despite its limitations, including a positive predictive value of only 25-40%, PSA remains the only generally accepted biomarker for prostate cancer.

Prostate cancer is, in most cases, slow-growing and symptom-free. Moreover, since men with the condition are typically older, they often die of causes unrelated to the prostate cancer, such as heart/circulatory disease, pneumonia, other unrelated cancers, or old age. On the other hand, the more aggressive prostate cancers account for more cancer-related deaths among men in the United States than any other cancer except lung cancer.

About two-thirds of prostate cancer cases are slow growing, whereas the other third are more aggressive and fast developing. It is important to be able to distinguish between aggressive and non-aggressive forms of the disease, and further, to distinguish prostate cancer from benign prostate hyperplasia (BPH). Commonly used screening tests, e.g., for prostate specific antigen (PSA) cannot distinguish between prostate cancer and BPH.

Filamin A (FLNA) (also known as FLN-A, FLN1, ABP-280, OPD1, OPD2, Endothelial Actin-Binding Protein, CVD1, FMD, MNS, NHBP, XLVD, XMVD, Actin Binding Protein 280, Alpha-Filamin, Filamin-1, Filamin-A—each of which may appear herein and are considered equivalent terms as used herein) is a 280-kD protein that is thought to crosslink actin filaments into orthogonal networks in cortical cytoplasm. The large molecular-weight protein also participates in the anchoring of membrane proteins to the actin cytoskeleton. FLNA has previously been associated with various cancers.

There remains a need for markers and methods that can be used for the diagnosis, monitoring or prognosis of prostate cancer.

SUMMARY OF THE INVENTION

This invention pertains to FLNA binding proteins, in particular, to human FLNA binding proteins. Binding proteins of the inventions include, but are not limited to antibodies, antigen binding portions, and other antigen binding proteins capable of binding the FLNA. Further, the invention provides methods of making and using FLNA binding proteins. The inventions also provides methods for the diagnosis, monitoring or prognosis of prostate cancer in a subject.

In one aspect, the invention provides a binding protein comprising an antigen binding domain, said binding protein capable of binding filamin A (FLNA), said antigen binding domain comprising a heavy chain CDR3 domain comprising the amino acid sequence selected from the group consisting of SEQ ID NO: 9, SEQ ID NO: 15 or SEQ ID NO: 21.

In one embodiment of the foregoing aspect, the binding protein further comprises a heavy chain CDR2 domain comprising the amino acid sequence selected from the group consisting of SEQ ID NO: 8, SEQ ID NO: 14 or SEQ ID NO: 20.

In another embodiment of the foregoing aspect, the binding protein further comprises a heavy chain CDR1 domain comprising the amino acid sequence selected from the group consisting of SEQ ID NO: 7, SEQ ID NO: 13 or SEQ ID NO: 19.

In another embodiment of the foregoing aspect, the binding protein further comprises a light chain CDR3 domain comprising the amino acid sequence selected from the group consisting of SEQ ID NO: 12, SEQ ID NO: 18 or SEQ ID NO: 24.

In another embodiment of the foregoing aspect, the binding protein further comprises a light chain CDR2 domain comprising the amino acid sequence selected from the group consisting of SEQ ID NO: 11, SEQ ID NO: 17 or SEQ ID NO: 23.

In another embodiment of the foregoing aspect, the binding protein further comprises a light chain CDR1 domain comprising the amino acid sequence selected from the group consisting of SEQ ID NO: 10, SEQ ID NO: 16 or SEQ ID NO: 22.

In another aspect, the invention provides a binding protein comprising an antigen binding domain, said binding protein capable of binding filamin A (FLNA), said antigen binding domain comprising a heavy chain variable region comprising a CDR3 domain comprising the amino acid sequence set forth in SEQ ID NO: 9, a CDR2 domain comprising the amino acid sequence set forth in SEQ ID NO: 8, and a CDR1 domain comprising the amino acid sequence set forth in SEQ ID NO: 7 or a heavy chain variable region comprising a CDR3 domain comprising the amino acid sequence set forth in SEQ ID NO: 15, a CDR2 domain comprising the amino acid sequence set forth in SEQ ID NO: 14, and a CDR1 domain comprising the amino acid sequence set forth in SEQ ID NO: 13 or a heavy chain variable region comprising a CDR3 domain comprising the amino acid sequence set forth in SEQ ID NO: 21, a CDR2 domain comprising the amino acid sequence set forth in SEQ ID NO: 20, and a CDR1 domain comprising the amino acid sequence set forth in SEQ ID NO: 19; and a light chain variable region comprising a CDR3 domain comprising the amino acid sequence set forth in SEQ ID NO: 12, a CDR2 domain comprising the amino acid sequence set forth in SEQ ID NO: 11, and a CDR1 domain comprising the amino acid sequence set forth in SEQ ID NO: 10 or a light chain variable region comprising a CDR3 domain comprising the amino acid sequence set forth in SEQ ID NO: 18, a CDR2 domain comprising the amino acid sequence set forth in SEQ ID NO: 17, and a CDR1 domain comprising the amino acid sequence set forth in SEQ ID NO: 16 or a light chain variable region comprising a CDR3 domain comprising the amino acid sequence set forth in SEQ ID NO: 24, a CDR2 domain comprising the amino acid sequence set forth in SEQ ID NO: 23, and a CDR1 domain comprising the amino acid sequence set forth in SEQ ID NO: 22.

In one embodiment of any of the foregoing aspects, the antigen binding domain comprises a heavy chain variable region selected from the group consisting of: the amino acid sequence set forth in SEQ ID NO: 1, the amino acid sequence set forth in SEQ ID NO: 3 or the amino acid sequence set forth in SEQ ID NO: 5.

In another embodiment of any of the foregoing aspects, the antigen binding domain comprises a light chain variable region selected from the group consisting of: the amino acid sequence set forth in SEQ ID NO: 2, the amino acid sequence set forth in SEQ ID NO: 4 or the amino acid set forth in SEQ ID NO: 6.

In another embodiment of any of the foregoing aspects, the antigen binding domain comprises a heavy chain variable region comprising the amino acid sequence set forth in SEQ ID NO: 1 and a light chain variable region comprising the amino acid sequence set forth in SEQ ID NO: 2.

In another embodiment of any of the foregoing aspects, the antigen binding domain comprises a heavy chain variable region comprising the amino acid sequence set forth in SEQ ID NO: 3 and a light chain variable region comprising the amino acid sequence set forth in SEQ ID NO: 4.

In another embodiment of any of the foregoing aspects, the antigen binding domain comprises a heavy chain variable region comprising the amino acid sequence set forth in SEQ ID NO: 5 and a light chain variable region comprising the amino acid sequence set forth in SEQ ID NO: 6.

In another embodiment of any of the foregoing aspects, the antigen binding domain comprises a heavy chain comprising the amino acid sequence set forth in SEQ ID NO: 25, and a light chain comprising the amino acid sequence set forth in SEQ ID NO: 26; or the antigen binding domain comprises a heavy chain comprising the amino acid sequence set forth in SEQ ID NO: 27, and a light chain comprising the amino acid sequence set forth in SEQ ID NO: 28; or the antigen binding domain comprises a heavy chain comprising the amino acid sequence set forth in SEQ ID NO: 29, and a light chain comprising the amino acid sequence set forth in SEQ ID NO: 30.

In another embodiment of any of the foregoing aspects, the binding protein has an on rate constant ($K_{on}$) to FLNA selected from the group consisting of: at least about $7.90 \times 10^4$ $M^{-1}$ $s^{-1}$, at least about $8.05 \times 10^5$ $M^{-1}$ $s^{-1}$, and at least about $1.95 \times 10^5$ $M^{-1}$ $s^{-1}$. In another embodiment of any of the foregoing aspects, the binding protein has a dissociation constant ($K_D$) to FLNA selected from the group consisting of: $4.82 \times 10^{-9}$ $s^{-1}$ or less; $9.99 \times 10^{-10}$ $s^{-1}$ or less; $4.02 \times 10^{-9}$ $s^{-1}$ or less.

In one embodiment of any of the foregoing aspects, the binding protein is an antibody.

In another aspect, the invention provides an antibody construct comprising the binding protein of any one of the foregoing aspects, said antibody construct further comprises a linker polypeptide or an immunoglobulin constant domain.

In one embodiment of any of the foregoing aspects, the binding protein is selected from the group consisting of: an immunoglobulin molecule, a monoclonal antibody, a murine antibody, a chimeric antibody, a CDR-grafted antibody, a humanized antibody, a single domain antibody, a Fv, a disulfide linked Fv, a scFv, a diabody, a Fab, a Fab', a F(ab')2, a multispecific antibody, a dual specific antibody, and a bispecific antibody.

In another embodiment of any of the foregoing aspects, the binding protein comprises a heavy chain immunoglobulin constant domain selected from the group consisting of: a IgM constant domain, a IgG4 constant domain, a IgG1 constant domain, a IgE constant domain, a IgG2 constant domain, a IgG3 constant domain and a IgA constant domain. In one embodiment of any of the foregoing aspects, the binding protein comprises a IgG1 or IgG2 constant domain.

In another aspect, the invention provides an isolated nucleic acid encoding a binding protein amino acid sequence of the invention.

In another aspect, the invention provides an isolated nucleic acid encoding an antibody construct amino acid sequence of the invention.

In another aspect, the invention provides a vector comprising an isolated nucleic acid of the invention.

In another aspect, the invention provides a host cell comprising a vector of the invention. In one embodiment, the host cell is a prokaryotic cell or a eukaryotic cell. In another embodiment, the prokaryotic host cell is *E. Coli*. In another embodiment, the eukaryotic cell is selected from the group consisting of a protist cell, an animal cell, a plant cell and a fungal cell. In one embodiment, the animal cell is selected from the group consisting of a mammalian cell, an avian cell, and an insect cell.

In another embodiment of any of the foregoing aspects, the host cell is selected from the group consisting of a CHO cell, a COS cell, a yeast cell, and an insect Sf9 cell. In one embodiment, the yeast cell is *Saccharomyces cerevisiae*.

In another aspect, the invention provides a method of producing an antibody, or antigen binding portion thereof, comprising culturing a host cell of the invention in culture medium so that the nucleic acid is expressed and the antibody is produced.

In another aspect, the invention provides a transgenic mouse comprising the host cell of the invention, wherein the mouse expresses a polypeptide encoded by the nucleic acid, or antigen binding portion thereof, that binds to FLNA.

In another aspect, the invention provides a hybridoma that produces an antibody construct of the invention.

In another aspect, the invention provides a method of producing a protein capable of binding FLNA, comprising culturing a host cell of the invention in culture medium under conditions sufficient to produce a binding protein capable of binding FLNA.

In another aspect, the invention provides a protein produced according to any of the methods of the invention.

In one embodiment of any of the foregoing aspects, the method of preparing an antibody comprises expressing a nucleic acid under conditions to bring about expression of said antibody, and recovering said antibody.

In another aspect, the invention provides a pharmaceutical composition comprising the binding protein of the invention, and a pharmaceutically acceptable carrier.

In one aspect, the invention provides methods for diagnosing an abnormal prostate state in a subject comprising detecting a level of FLNA in a biological sample from the subject; and comparing the level of FLNA in the biological sample with the level of FLNA in a normal control sample, wherein the level of FLNA is detected using a binding protein of the invention; and wherein an altered level of FLNA in the biological sample relative to the normal control sample is indicative of an abnormal prostate state in the subject.

In one embodiment of the foregoing aspect, the level of FLNA is detected using an enzyme-linked immunosorbent assay (ELISA), radioimmunoassay (RIA), antibody-labeled fluorescence imaging, tissue immunohistochemistry, or an immunoprecipitation-multiple reaction monitoring (IP-MRM) assay In another aspect, the invention provides methods for diagnosing an abnormal prostate state in a subject comprising detecting a level of FLNA in a biological sample from the subject; and comparing the level of FLNA in the biological sample with the level of FLNA in a normal control sample, wherein the level of FLNA is detected using multiple reaction monitoring (MRM) mass spectrometry, wherein the MRM comprises detecting one or more surrogate peptides comprising the amino acid sequence of SEQ ID NO:40 (P2) and/or SEQ ID NO:41 (P4); and wherein an altered level of FLNA in the biological sample relative to the normal control sample is indicative of an abnormal prostate state in the subject.

In one embodiment of the foregoing aspect, the range of detection for P2 is 62.5 pg/mL to 1500 pg/mL and the range of detection for P4 563 pg/mL to 27000 pg/mL.

In another embodiment of the foregoing aspect, the MRM is immunoprecipitation-multiple reaction monitoring (IP-MRM) comprising a FLNA immunoprecipitation step.

In one embodiment of the foregoing aspect, the immunoprecipitation step is carried out using a binding protein of the invention.

In another embodiment of the foregoing aspect, a P2 internal standard (P2_IS) and/or a P4 internal standard (P4_IS) is also detected.

In another embodiment of the foregoing aspect, the MRM comprises monitoring one or more mass transitions m/z selected from the group consisting of: 441.7 $(M+2H)^{2+} \rightarrow$ 584.5 $(y_5^{1+})$ for P2; 535 $(M+3H)^{3+} \rightarrow$ 832.4 $(y_8^{1+})$ for P4, 445.5 $(M+2H)^{2+} \rightarrow$ 592.1 $(y_5^{1+})$ for P2 internal standard (P2_IS), and 538.4 $(M+3H)^{3+} \rightarrow$ 842.5 $(y_8^{1+})$ for P4 internal standard P4_IS.

In one embodiment of the foregoing aspects, an increased level of FLNA in the biological sample relative to the normal control sample is indicative of an abnormal prostate state in the subject. In another embodiment of the foregoing aspects, no increase in the detected level of FLNA in the biological sample relative to the normal control sample is indicative of a normal prostate state in the subject.

In one embodiment, the methods of the foregoing aspects further comprise detecting the level of prostate specific antigen (PSA) in the biological sample.

In another embodiment, the methods of the foregoing aspects further comprise comparing the level of PSA in the biological sample to the level of PSA in a normal control sample. In one embodiment, an increase in the level of FLNA in the biological sample relative to the normal control sample, in combination with an increase in the level of PSA in the biological sample relative to the level of PSA in the normal control sample is indicative of an abnormal prostate state in the subject. In another embodiment, no increase in the detected level of expression FLNA in the biological sample relative to the normal control sample, in combination with a decreased or normal level of PSA in the biological sample as compared to the level of PSA in the normal control sample, is indicative of a normal prostate state in the subject.

In one embodiment, the methods of the foregoing aspects further comprise detecting the level of keratin 19 (KRT19) and/or filamin B (FLNB) in the biological sample. In another embodiment, the methods of the foregoing aspects further comprise comparing the level of keratin 19 (KRT19) and/or filamin B (FLNB) in the biological sample to the level of keratin 19 (KRT19) and/or filamin B (FLNB) in a normal control sample.

In one embodiment of the foregoing aspects, the abnormal prostate state is prostate cancer. In one embodiment, prostate cancer is selected from the group consisting of: androgen-dependent prostate cancer, androgen-independent prostate cancer, aggressive prostate cancer and non-aggressive prostate cancer.

In another aspect, the invention provides methods for identifying a subject as being at increased risk for developing prostate cancer, the method comprising detecting a level of FLNA in a biological sample from the subject; and comparing the level of FLNA in the biological sample with the level of FLNA in a normal control sample, wherein the level of FLNA is detected using a binding protein of the invention; and wherein an altered level of FLNA in the biological sample relative to the normal control sample is indicative of an increased risk for developing prostate cancer in the subject.

In one embodiment of the foregoing aspect, the level of FLNA is detected using an enzyme-linked immunosorbent assay (ELISA), radioimmunoassay (RIA), antibody-labeled fluorescence imaging, tissue immunohistochemistry, or an immunoprecipitation-multiple reaction monitoring (IP-MRM) assay.

In another aspect, the invention provides methods for identifying a subject as being at increased risk for developing prostate cancer, the method comprising detecting a level of FLNA in a biological sample from the subject; and comparing the level of FLNA in the biological sample with the level of FLNA in a normal control sample, wherein the level of FLNA is detected using multiple reaction monitoring (MRM) mass spectrometry, wherein the MRM comprises detecting one or more surrogate peptides comprising the amino acid sequence of SEQ ID NO:40 (P2) and/or SEQ ID NO:41 (P4); and wherein an altered level of FLNA in the biological sample relative to the normal control sample is indicative of an increased risk for developing prostate cancer in the subject.

In one embodiment of the foregoing aspects, the range of detection for P2 is 62.5 pg/mL to 1500 pg/mL and the range of detection for P4 563 pg/mL to 27000 pg/mL.

In another embodiment of the foregoing aspects, the MRM is immunoprecipitation-multiple reaction monitoring (IPMRM) comprising a FLNA immunoprecipitation step.

In one embodiment of the foregoing aspects, the immunoprecipitation step is carried out using a binding protein of the invention.

In one embodiment of the foregoing aspects, a P2 internal standard (P2_IS) and/or a P4 internal standard (P4_IS) is also detected.

In another embodiment of the foregoing aspects, MRM comprises monitoring one or more mass transitions m/z selected from the group consisting of: 441.7 $(M+2H)^{2+} \rightarrow$ 584.5 $(y_5^{1+})$ for P2; 535 $(M+3H)^{3+} \rightarrow$ 832.4 $(y_8^{1+})$ for P4, 445.5 $(M+2H)^{2+} \rightarrow$ 592.1 $(y_5^{1+})$ for P2 internal standard (P2_IS), and 538.4 $(M+3H)^{3+} \rightarrow$ 842.5 $(y_8^{1+})$ for P4 internal standard P4_IS.

In another embodiment of the foregoing aspects, the method further comprises detecting the level of PSA, keratin 19 (KRT19) and/or filamin B (FLNB) in the biological sample. In another embodiment of the foregoing aspects, the method further comprises comparing the level of PSA, keratin 19 (KRT19) and/or filamin B (FLNB) in the biological sample to the level of PSA, keratin 19 (KRT19) and/or filamin B (FLNB) in a normal control sample.

In another aspect, the invention provides methods for monitoring prostate cancer in a subject, the method comprising detecting a level of FLNA in a first biological sample obtained at a first time from a subject having prostate cancer; detecting a level of expression of FLNA in a second biological sample obtained from the subject at a second time, wherein the second time is later than the first time; and comparing the level of FLNA in the second sample with the level of FLNA in the first sample, wherein the level of FLNA is detected using a binding protein of the invention; and wherein a change in the level of FLNA in the second sample as compared to the first sample is indicative of a change in prostate cancer status in the subject.

In one embodiment of the foregoing aspects, the level of FLNA is detected using an enzyme-linked immunosorbent assay (ELISA), radioimmunoassay (RIA), antibody-labeled fluorescence imaging, tissue immunohistochemistry, or an immunoprecipitation-multiple reaction monitoring (IPMRM) assay.

In another aspect, the invention provides methods for monitoring prostate cancer in a subject, the method comprising detecting a level of FLNA in a first biological sample obtained at a first time from a subject having prostate cancer; detecting a level of expression of FLNA in a second biological sample obtained from the subject at a second time, wherein the second time is later than the first time; and comparing the level of FLNA in the second sample with the level of FLNA in the first sample, wherein the level of FLNA is detected using multiple reaction monitoring (MRM) mass spectrometry, wherein the MRM comprises detecting one or more surrogate peptides comprising the amino acid sequence of SEQ ID NO:40 (P2) and/or SEQ ID NO:41 (P4); and wherein a change in the level of FLNA in the second sample as compared to the first sample is indicative of a change in prostate cancer status in the subject.

In one embodiment of the foregoing aspects, the range of detection for P2 is 62.5 pg/mL to 1500 pg/mL and the range of detection for P4 563 pg/mL to 27000 pg/mL.

In one embodiment of the foregoing aspects, the MRM is immunoprecipitation-multiple reaction monitoring (IPMRM) comprising a FLNA immunoprecipitation step.

In another embodiment of the foregoing aspects, the immunoprecipitation step is carried out using a binding protein of the invention.

In one embodiment of the foregoing aspects, a P2 internal standard (P2_IS) and/or a P4 internal standard (P4_IS) is also detected.

In one embodiment of the foregoing aspects, the MRM comprises monitoring one or more mass transitions m/z selected from the group consisting of: 441.7 $(M+2H)^{2+} \rightarrow$ 584.5 $(y_5^{1+})$ for P2; 535 $(M+3H)^{3+} \rightarrow$ 832.4 $(y_8^{1+})$ for P4, 445.5 $(M+2H)^{2+} \rightarrow$ 592.1 $(y_5^{1+})$ for P2 internal standard (P2_IS), and 538.4 $(M+3H)^{3+} \rightarrow$ 842.5 $(y_8^{1+})$ for P4 internal standard P4_IS.

In one embodiment of the foregoing aspects, the subject is actively treated for prostate cancer prior to obtaining the second sample. In another embodiment of the foregoing aspects, the subject is not actively treated for prostate cancer prior to obtaining the second sample.

In one embodiment of the foregoing aspects, an increased level of FLNA in the second biological sample as compared to the first biological sample is indicative of progression of the prostate cancer in the subject. In another embodiment of the foregoing aspects, no increase in the detected level of expression of FLNA in the second biological sample as compared to the first biological sample is indicative of non-progression of the prostate cancer in the subject.

In one embodiment of the foregoing aspects, the methods further comprise determining the level of prostate specific antigen (PSA) in the first biological sample and the second biological sample. In another embodiment of the foregoing aspects, the methods further comprise comparing the level of PSA in the second biological sample to the level of PSA in the first biological sample.

In one embodiment of the foregoing aspects, the methods further comprise detecting the level of keratin 19 (KRT19) and/or filamin B (FLNB) in the biological sample. In another embodiment of the foregoing aspects, the methods further comprise comparing the level of keratin 19 (KRT19) and/or filamin B (FLNB) in the biological sample to the level of keratin 19 (KRT19) and/or filamin B (FLNB) in a normal control sample.

In another aspect, the invention provides methods for detecting and/or quantifying the level of FLNA in a sample, comprising contacting the sample with a binding protein of the invention under conditions such that the binding protein binds to FLNA in the sample, to thereby detect and/or quantify the level of FLNA in a sample.

In another aspect, the invention provides a method for detecting and/or quantifying the level of FLNA in a sample, comprising detecting and/or quantifying one or more surrogate peptides, wherein the one or more surrogate peptides comprise the amino acid sequence of SEQ ID NO:40 (P2) and/or SEQ ID NO:41 (P4), in a protein digest prepared from said sample using mass spectrometry.

In one embodiment of the foregoing aspects, the mass spectrometry is multiple reaction monitoring (MRM) mass spectrometry.

In one embodiment of the foregoing aspects, the MRM is immunoprecipitation-multiple reaction monitoring (IP-MRM) comprising a FLNA immunoprecipitation step.

In one embodiment of the foregoing aspects, the immunoprecipitation step is carried out using a binding protein of the invention.

In another embodiment of the foregoing aspects, the range of detection for P2 is 62.5 pg/mL to 1500 pg/mL and the range of detection for P4 563 pg/mL to 27000 pg/mL.

In another embodiment of the foregoing aspects, a P2 internal standard (P2_IS) and/or a P4 internal standard (P4_IS) is also detected.

In one embodiment of the foregoing aspects, the MRM comprises monitoring one or more mass transitions m/z selected from the group consisting of: 441.7 $(M+2H)^{2+}\rightarrow$ 584.5 $(y_5^{1+})$ for P2; 535 $(M+3H)^{3+}\rightarrow$832.4 $(y_8^{1+})$ for P4, 445.5 $(M+2H)^{2+}\rightarrow$592.1 $(y_5^{1+})$ for P2 internal standard (P2_IS), and 538.4 $(M+3H)^{3+}\rightarrow$842.5 $(y_8^{1+})$ for P4 internal standard P4_IS.

In another aspect, the invention provides a panel of one or more reagents for use in a detection method, the panel comprising a detection reagent specific for the detection of FLNA, wherein the detection reagent is a binding protein of the invention.

In one embodiment of the foregoing aspects, the panel further comprises a detection reagent for specific for the detection of PSA, keratin 19 (KRT19), filamin B (FLNB), or a combination thereof.

In another aspect, the invention provides a kit for the diagnosis, monitoring, or characterization of an abnormal prostate state, comprising: at least one reagent specific for the detection of a level of FLNA, wherein the detection reagent is a binding protein of the invention.

In one embodiment of the foregoing aspects, the kit further comprises instructions for the diagnosis, monitoring, or characterization of an abnormal prostate state based on the level of FLNA detected.

In one embodiment of the foregoing aspects, the kit further comprises instructions to detect the level of PSA, keratin 19 (KRT19), filamin B (FLNB), or a combination thereof, in a sample in which FLNA is detected.

In another embodiment of the foregoing aspects, the kit further comprises at least one reagent specific for the detection of a level of PSA, keratin 19 (KRT19), filamin B (FLNB), or a combination thereof.

DETAILED DESCRIPTION OF THE INVENTION

Figure 1:
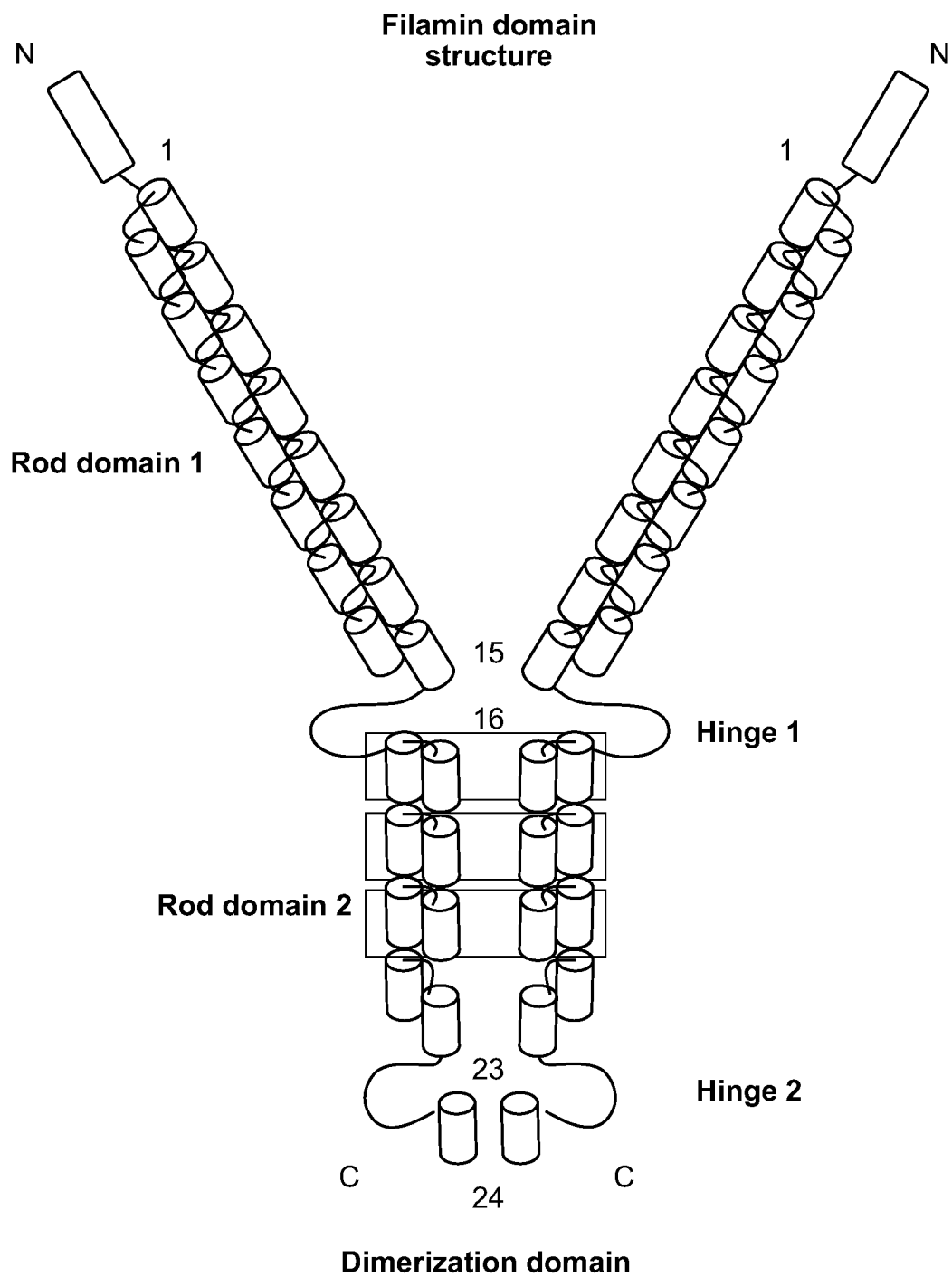
FIG. 1 shows a schematic of filamin domain structure.

This invention pertains to FLNA binding proteins, particularly human FLNA binding proteins, and more particularly anti-FLNA antibodies, or antigen-binding portions thereof, that bind FLNA, and uses thereof. Various aspects of the invention relate to antibodies and antibody fragments, conjugates thereof and pharmaceutical compositions thereof, as well as nucleic acids, recombinant expression vectors and host cells for making such antibodies and fragments. Methods of using the antibodies of the invention to detect FLNA and to diagnose, monitor or prognose disorders such as prostate cancer are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. The term "such as" is used herein to mean, and is used interchangeably, with the phrase "such as but not limited to."

The articles "a" and "an" are used herein to refer to one or to more than one (i.e. to at least one) of the grammatical object of the article. By way of example, "an element" means one element or more than one element.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. As used herein, "one or more" is understood as each value 1, 2, 3, 4, 5, 6, 7, 8, 9, 10, and any value greater than 10.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art. An example of an isolated polypeptide is an isolated antibody, or antigen-binding portion thereof.

The term "Filamin A" (FLNA) as used herein refers to a member of the filamin family. Filamin A (also known as FLN-A, FLN1, ABP-280, OPD1, OPD2, Endothelial Actin-Binding Protein, CVD1, FMD, MNS, NHBP, XLVD, XMVD, Actin Binding Protein 280, Alpha-Filamin, Filamin-1, Filamin-A—each of which may appear herein and are considered equivalent terms as used herein) is a 280-kD protein that is thought to crosslink actin filaments into orthogonal networks in cortical cytoplasm. As used herein, filamin A refers to both the gene and the protein unless clearly indicated otherwise by context. The large molecular-weight protein also participates in the anchoring of membrane proteins to the actin cytoskeleton. Remodeling of the cytoskeleton is central to the modulation of cell shape and migration cells. Filamin A, encoded by the FLNA gene, is a widely expressed protein that regulates reorganization of the actin cytoskeleton by interacting with integrins, transmembrane receptor complexes, and second messengers. At least two different isoforms are known, isoform 1 and isoform 2, all of which are contemplated by the invention and encompassed by the term "filamin A" It will be appreciated that isoform 1 is the predominant transcript encoding filamin A Isoform 2 includes an alternate in-frame exon and encodes a slightly longer protein isoform. Interaction with FLNA may allow neuroblast migration from the ventricular zone into the cortical plate. FLNA tethers cell surface-localized furin, modulates its rate of internalization and directs its intracellular trafficking. Further reference to filamin A can be found in the scientific literature, for example, in Gorlin J B et la., (October 1993). "Actin-binding protein (ABP-280) filamin gene (FLN) maps telomeric to the color vision locus (R/GCP) and centromeric to G6PD in Xq28". Genomics 17 (2): 496-8, and Robertson S P et al. (March 2003). "Localized mutations in the gene encoding the cytoskeletal protein filamin A cause diverse malformations in humans". Nat Genet 33 (4): 487-91, each of which are incorporated herein by reference. The nucleotide and amino acid sequences of human filamin A can be found as GenBank Accession No. NM_001456.3 (filamin A-isoform 1-mRNA transcript sequence-SEQ ID NO: 31) and the corresponding polypeptide sequence of NP_001447.2 (filamin A-isoform 1-polypeptide sequence-SEQ ID NO: 32) and as GenBank Accession No. NM_001110556 (filamin A-isoform 2-mRNA transcript sequence-SEQ ID NO: 33) and the corresponding polypeptide sequence of NP_001104026 (filamin A-isoform 2-polypeptide sequence-SEQ ID NO: 34). These GenBank numbers are incorporated herein by reference in the versions available on the earliest effective filing date of this application.

It is understood that the invention includes the use of any combination of one or more of the filamin A sequences provided in the sequence listing or any fragments thereof as long as the fragment can allow for the specific identification of filamin A. Methods of the invention and reagents can be used to detect single isoforms of filamin A, combinations of filamin A isoforms, or all of the filamin A isoforms simultaneously. Unless specified, filamin A can be considered to refer to one or more isoforms of filamin A, including total filamin A. Moreover, it is understood that there are naturally occurring variants of filamin A, which may or may not be associated with a specific disease state, the use of which are also included in the instant application.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., FLNA). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

An "isolated antibody", as used herein, is intended to refer to an antibody that is substantially free of other antibodies having different antigenic specificities (e.g., an isolated antibody that specifically binds FLNA is substantially free of antibodies that specifically bind antigens other than FLNA). An isolated antibody that specifically binds human FLNA may, however, have cross-reactivity to other antigens, such as FLNA molecules from other species. Moreover, an isolated antibody may be substantially free of other cellular material and/or chemicals.

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., *J. Mol. Biol.* 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (*J Mol Biol* 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

In preferred embodiments of the present invention, the CDRs are determined by the IMGT numbering system (Lefranc et al., Nucleic Acids Research, 27, 209-212 (1990)).

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

The term "epitope" includes any polypeptide determinant capable of specific binding to a binding protein, e.g., an antibody or antigen binding portion thereof. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In various embodiments, an epitope may be a linear or sequential epitope, i.e., a linear sequence of amino acids, of the primary structure of the antigen, i.e., FLNA. Alternatively, in other embodiments, an epitope may be a conformational epitope having a specific three-dimensional shape when the antigen assumes its secondary structure. For example, the conformational epitope may comprise non-linear, i.e., non-sequential, amino acids of the antigen.

In a particular embodiment, an epitope is a region of an antigen that is bound by a binding protein, e.g., antibody or antigen binding portion thereof. In certain embodiments, a binding protein, e.g., antibody or antigen binding portion thereof, is said to specifically bind an antigen when it preferentially recognizes its target antigen in a complex mixture of proteins and/or macromolecules.

In certain embodiments, the epitope is a linear motif ERPLVGV (SEQ ID NO: 42), corresponding to residue 1774-1780 in the hinge connecting Filamin domains 15 and 16 of the target protein.

The term "$K_D$", as used herein, is intended to refer to the dissociation constant of a particular antibody-antigen interaction as is known in the art.

The term "$k_{ON}$", as used herein, is intended to refer to the on rate constant for association of an antibody to the antigen to form the antibody/antigen complex as is known in the art.

The term "$k_{OFF}$", as used herein, is intended to refer to the off rate constant for dissociation of an antibody from the antibody/antigen complex as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "polynucleotide" as used herein refers to a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Protein constructs of the present invention may be expressed, and purified using expression vectors and host cells known in the art, including expression cassettes, vectors, recombinant host cells and methods for the recombinant expression and proteolytic processing of recombinant polyproteins and pre-proteins from a single open reading frame (e.g., WO 2007/014162 incorporated herein by reference).

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

A "patient" or "subject" to be treated by the method of the invention can mean either a human or non-human animal, preferably a mammal. By "subject" is meant any animal, including horses, dogs, cats, pigs, goats, rabbits, hamsters, monkeys, guinea pigs, rats, mice, lizards, snakes, sheep, cattle, fish, and birds. A human subject may be referred to as a patient. It should be noted that clinical observations described herein were made with human subjects and, in at least some embodiments, the subjects are human.

The terms "disorders", "diseases", and "abnormal state" are used inclusively and refer to any deviation from the normal structure or function of any part, organ, or system of the body (or any combination thereof). A specific disease is manifested by characteristic symptoms and signs, including biological, chemical, and physical changes, and is often associated with a variety of other factors including, but not limited to, demographic, environmental, employment, genetic, and medically historical factors. Certain characteristic signs, symptoms, and related factors can be quantitated through a variety of methods to yield important diagnostic information. As used herein the disorder, disease, or abnormal state is an abnormal prostate state, including benign prostate hyperplasia and cancer, particularly prostate cancer. The abnormal prostate state of prostate cancer can be further subdivided into stages and grades of prostate cancer as provided, for example in Prostate. In: Edge S B, Byrd D R, Compton C C, et al., eds.: AJCC Cancer Staging Manual. 7th ed. New York, N.Y.: Springer, 2010, pp 457-68 (incorporated herein by reference). Further, abnormal prostate states can be classified as one or more of benign prostate hyperplasia (BPH), androgen sensitive prostate cancer, androgen insensitive or resistant prostate cancer, aggressive prostate cancer, non-aggressive prostate cancer, metastatic prostate cancer, and non-metastatic prostate cancer. Further, the prostate cancer may be a prostatic intraepithelial neoplasia, adenocarcinoma, small cell carcinoma, or squamous cell carcinoma.

A subject at "increased risk for developing prostate cancer" may or may not develop prostate cancer. Identification of a subject at increased risk for developing prostate cancer should be monitored for additional signs or symptoms of prostate cancer. The methods provided herein for identifying a subject with increased risk for developing prostate cancer can be used in combination with assessment of other known risk factors or signs of prostate cancer including, but not limited to decreased urinary stream, urgency, hesitancy, nocturia, incomplete bladder emptying, and age.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene", "gene expression level", "level of a marker", and the like refer to the level of mRNA, as well as pre-mRNA nascent transcript(s), transcript processing intermediates, mature mRNA(s) and degradation products, or the level of protein, encoded by the gene in the cell.

The term "specific identification" is understood as detection of a marker of interest with sufficiently low background of the assay and cross-reactivity of the reagents used such that the detection method is diagnostically useful. In certain embodiments, reagents for specific identification of a marker bind to only one isoform of the marker. In certain embodiments, reagents for specific identification of a marker bind to more than one isoform of the marker. In certain embodiments, reagents for specific identification of a marker bind to all known isoforms of the marker.

The term "control sample," as used herein, refers to any clinically relevant comparative sample, including, for example, a sample from a healthy subject not afflicted with an oncological disorder, e.g., prostate cancer, or a sample from a subject from an earlier time point, e.g., prior to treatment, an earlier tumor assessment time point, at an earlier stage of treatment. A control sample can be a purified sample, protein, and/or nucleic acid provided with a kit. Such control samples can be diluted, for example, in a dilution series to allow for quantitative measurement of levels of analytes, e.g., markers, in test samples. A control sample may include a sample derived from one or more subjects. A control sample may also be a sample made at an earlier time point from the subject to be assessed. For example, the control sample could be a sample taken from the subject to be assessed before the onset of an oncological disorder, e.g., prostate cancer, at an earlier stage of disease, or before the administration of treatment or of a portion of treatment. The control sample may also be a sample from an animal model, or from a tissue or cell lines derived from the animal model of oncological disorder, e.g., prostate cancer. The level of activity or expression of a marker, e.g. FLNA, in a control sample consists of a group of measurements that may be determined based on any appropriate statistical measure, such as, for example, measures of central tendency including average, median, or modal values. Different from a control is preferably statistically significantly different from a control.

The term "control level" refers to an accepted or predetermined level of a marker in a subject sample. A control level can be a range of values. Marker levels can be compared to a single control value, to a range of control values, to the upper level of normal, or to the lower level of normal as appropriate for the assay.

In one embodiment, the control is a standardized control, such as, for example, a control which is predetermined using an average of the levels of expression of one or more markers from a population of subjects having no cancer, especially subjects having no prostate cancer. In still other embodiments of the invention, a control level of a marker in a non-cancerous sample(s) derived from the subject having cancer. For example, when a biopsy or other medical procedure reveals the presence of cancer in one portion of the tissue, the control level of a marker may be determined using the non-affected portion of the tissue, and this control level may be compared with the level of the marker in an affected portion of the tissue.

In certain embodiments, the control can be from a subject, or a population of subject, having an abnormal prostate state. For example, the control can be from a subject suffering from benign prostate hyperplasia (BPH), androgen sensitive prostate cancer, androgen insensitive or resistant prostate cancer, aggressive prostate cancer, non-aggressive prostate cancer, metastatic prostate cancer, or non-metastatic prostate cancer. It is understood that not all markers will have different levels for each of the abnormal prostate states listed. It is understood that a combination of maker levels may be most useful to distinguish between abnormal prostate states, possibly in combination with other diagnostic methods. Further, marker levels in biological samples can be compared to more than one control sample (e.g., normal, abnormal, from the same subject, from a population control). Marker levels can be used in combination with other signs or symptoms of an abnormal prostate state to provide a diagnosis for the subject.

A control can also be a sample from a subject at an earlier time point, e.g., a baseline level prior to suspected presence of disease, before the diagnosis of a disease, at an earlier assessment time point during watchful waiting, before the treatment with a specific agent (e.g., chemotherapy, hormone therapy) or intervention (e.g., radiation, surgery). In certain embodiments, a change in the level of the marker in a subject can be more significant than the absolute level of a marker, e.g., as compared to control.

As used herein, a sample obtained at an "earlier time point" is a sample that was obtained at a sufficient time in the past such that clinically relevant information could be obtained in the sample from the earlier time point as compared to the later time point. In certain embodiments, an earlier time point is at least four weeks earlier. In certain embodiments, an earlier time point is at least six weeks earlier. In certain embodiments, an earlier time point is at least two months earlier. In certain embodiments, an earlier time point is at least three months earlier. In certain embodiments, an earlier time point is at least six months earlier. In certain embodiments, an earlier time point is at least nine months earlier. In certain embodiments, an earlier time point is at least one year earlier. Multiple subject samples (e.g., 3, 4, 5, 6, 7, or more) can be obtained at regular or irregular intervals over time and analyzed for trends in changes in marker levels. Appropriate intervals for testing for a particular subject can be determined by one of skill in the art based on ordinary considerations.

As used herein, "changed as compared to a control" sample or subject is understood as having a level of the analyte or diagnostic or therapeutic indicator (e.g., marker) to be detected at a level that is statistically different than a sample from a normal, untreated, or abnormal state control sample. Changed as compared to control can also include a difference in the rate of change of the level of one or more markers obtained in a series of at least two subject samples obtained over time. Determination of statistical significance is within the ability of those skilled in the art, e.g., the number of standard deviations from the mean that constitute a positive or negative result.

As used herein, the term "obtaining" is understood herein as manufacturing, purchasing, or otherwise coming into possession of.

As used herein, "surrogate peptide" is understood as any peptide derived from a FLNA marker wherein the surrogate peptide is prepared by digesting the marker protein, e.g., FLNA, with a protease of known specificity (e.g., trypsin or endoproteinase Lys-C), and wherein the peptide can be used as a surrogate reporter to determine the abundance of the FLNA marker protein, and optionally isoforms or fragments thereof, in a sample, using a mass spectrometry-based assay, e.g., MRM or IPMRM. Surrogate peptides can be tryptic peptides between, for example, about 8 and 22 amino acids. Surrogate peptides can be chosen by methods known in the art, e.g., Skyline software and LC-MS/MS analysis (LTQ Orbitrap Velos coupled to Eksigent nano-LC) of recombinant protein (GenScript) tryptic digest. Surrogate peptides can be chosen based on surrogate peptide selection rules (Halquist, et al., *Biomed Chromatography* 25 (1-2):47-58) and signal intensities of the peptides in spiked and unspiked serum digests. The uniqueness of the surrogate peptides to the target FLNA marker can be confirmed by BLAST searches.

As used herein, "detecting", "detection", "determining", and the like are understood that an assay performed for identification of a specific marker in a sample, e.g., FLNA. The amount of marker expression or activity detected in the sample can be none or below the level of detection of the assay or method.

Reference will now be made in detail to exemplary embodiments of the invention. While the invention will be described in conjunction with the exemplary embodiments, it will be understood that it is not intended to limit the invention to those embodiments. To the contrary, it is intended to cover alternatives, modifications, and equivalents as may be included within the spirit and scope of the invention as defined by the appended claims.

I. Antibodies that Bind Filamin A (FLNA)

One aspect of the present invention provides isolated murine monoclonal antibodies, or antigen-binding portions thereof, that bind to FLNA. Preferably, the antibodies bind human FLNB. Methods of making the antibodies, methods of producing the antibodies and the anti-FLNA antibodies are described in detail hereinbelow.

A. Method of Making Anti-FLNA Antibodies

Antibodies of the present invention may be made by any of a number of techniques known in the art. The general methodology for making monoclonal antibodies by hybridomas is well known Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammering et al., "Monoclonal Antibodies And T cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; and 4,493,890. Methods for producing polyclonal anti-EFGR antibodies are well-known in the art. See U.S. Pat. No. 4,493,795 to Nestor et al.

Panels of monoclonal antibodies produced against FLNA can be screened for various properties; i.e., isotype, epitope, affinity, etc.

A monoclonal antibody, typically containing Fab and/or F(ab')2 portions of useful antibody molecules, can be prepared using the hybridoma technology described in Antibodies-A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an appropriate FLNA.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present antibody or binding member and their ability to inhibit specified tumorigenic or hyperproliferative activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/1 glucose, 20 mm glutamine, and 20% fetal calf serum. An exemplary inbred mouse strain is the Balb/c.

1. Anti-FLNA Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al.; Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. For example, monoclonal antibodies can be generated by the method of culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Briefly, mice can be immunized with a FLNA antigen. In certain embodiments, the FLNA antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with a FLNA antigen, antibodies and/or antibody-producing cells may be obtained from the animal. An anti-FLNA antibody-containing serum is obtained from the animal by bleeding or sacrificing the animal. The serum may be used as it is obtained from the animal, an immunoglobulin fraction may be obtained from the serum, or the anti-FLNB antibodies may be purified from the serum. Serum or immunoglobulins obtained in this manner are polyclonal, thus having a heterogeneous array of properties.

Once an immune response is detected, e.g., antibodies specific for the antigen FLNA are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding FLNA. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using FLNA, or a portion thereof, or a cell expressing FLNA. The initial screening is performed using an enzyme-linked immunoassay (ELISA) or a radioimmunoassay (RIA). An example of ELISA screening is provided in WO 00/37504, herein incorporated by reference.

Anti-FLNA antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described herein. In particular exemplary embodiments, the mouse hybridomas are 2C12, 3F4 and 6E7. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-FLNA antibody.

Antibody fragments that recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

In preferred embodiments, the present invention features a hybridoma that produces the antibody construct of any of the aspects or embodiments described herein. In certain embodiments, the hybridomas that produce the antibodies of the present invention are "2C12", "3F4" and "6E3," as described herein.

In certain embodiments, FLNA (aa 1443-2131) covering Filamin repeats 13-19 was manufactured as immunogen with E. coli expression system. The immunogen sequence is shown as below as SEQ ID NO: 35.

```
                                              SEQ ID NO: 35
MHHHHHHHDV TDASKVKCSG PGLSPGMVRA NLPQSFQVDT

SKAGVAPLQV KVQGPKGLVE PVDVVDNADG TQTVNYVPSR

EGPYSISVLY GDEEVPRSPF KVKVLPTHDA SKVKASGPGL

NTTGVPASLP VEFTIDAKDA GEGLLAVQIT DPEGKPKKTH

IQDNHDGTYT VAYVPDVTGR YTILIKYGGD EIPFSPYRVR

AVPTGDASKC TVTVSIGGHG LGAGIGPTIQ IGEETVITVD

TKAAGKGKVT CTVCTPDGSE VDVDVVENED GTFDIFYTAP

QPGKYVICVR FGGEHVPNSP FQVTALAGDQ PSVQPPLRSQ

QLAPQYTYAQ GGQQTWAPER PLVGVNGLDV TSLRPFDLVI

PFTIKKGEIT GEVRMPSGKV AQPTITDNKD GTVTVRYAPS

EAGLHEMDIR YDNMHIPGSP LQFYVDYVNC GHVTAYGPGL
```

```
            -continued
THGVVNKPAT FTVNTKDAGE GGLSLAIEGP SKAEISCTDN

QDGTCSVSYL PVLPGDYSIL VKYNEQHVPG SPFTARVTGD

DSMRMSHLKV GSAADIPINI SETDLSLLTA TVVPPSGREE

PCLLKRLRNG HVGISFVPKE TGEHLVHVKK NGQHVASSPI

PVVISQSEIG DASRVRVSGQ GLHEGHTFEP AEFIIDTRDA

GYGGLSLSIE GPSKVDINTE DLEDGTCRVT YCPTEPGNYI

INIKFADQHV PGSPFS
```

2. Anti-FLNA Monoclonal Antibodies Using Selected Lymphocyte Antibody Method

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) *Proc. Natl. Acad. Sci. USA* 93:7843-7848. In this method, single cells secreting antibodies of interest, e.g., lymphocytes derived from any one of the immunized animals described in Section 1, are screened using an antigen-specific hemolytic plaque assay, wherein the antigen FLNA, a subunit of FLNA, or a fragment thereof, is coupled to sheep red blood cells using a linker, such as biotin, and used to identify single cells that secrete antibodies with specificity for FLNA. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to FLNA. The amplified immunoglobulin sequences further can be manipulated in vitro, such as by in vitro affinity maturation methods such as those described in PCT Publication WO 97/29131 and PCT Publication WO 00/56772.

3. Anti-FLNA Monoclonal Antibodies Using Transgenic Animals

In another embodiment of the instant invention, antibodies are produced by immunizing a non-human animal comprising some, or all, of the human immunoglobulin locus with a FLNA antigen. In a preferred embodiment, the non-human animal is a XENOMOUSE transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and x light chain loci. See Mendez et al., *Nature Genetics* 15:146-156 (1997), Green and Jakobovits *J. Exp. Med.* 188:483-495 (1998), the disclosures of which are hereby incorporated by reference.

In certain embodiments, the invention features a transgenic mouse comprising a host cell comprising a vector comprising an isolated nucleic acid, wherein the mouse expresses a polypeptide encoded by the nucleic acid, or antigen binding portion thereof, that binds to FLNA. The isolated nucleic acid may encode a binding protein amino acid sequence as described herein, or an antibody construct as described herein.

4. Anti-FLNA Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

The recombinant antibody library may be from a subject immunized with FLNA, or a portion of FLNA, such as the extracellular domain. Alternatively, the recombinant antibody library may be from a naïve subject, i.e., one who has not been immunized with FLNA, such as a human antibody library from a human subject who has not been immunized with FLNA. Antibodies of the invention are selected by screening the recombinant antibody library with the peptide comprising FLNA to thereby select those antibodies that recognize FLNA. Methods for conducting such screening and selection are well known in the art, such as described in the references in the preceding paragraph. To select antibodies of the invention having particular binding affinities for FLNA, e.g. human FLNA, such as those that dissociate from FLNA with a particular $k_{off}$ rate constant, the art-known method of surface plasmon resonance can be used to select antibodies having the desired $k_{off}$ rate constant. To select antibodies of the invention having a particular neutralizing activity for FLNA, such as those with a particular an $IC_{50}$, standard methods known in the art for assessing the inhibition of FLNA activity may be used.

In one aspect, the invention pertains to an isolated antibody, or an antigen-binding portion thereof, that binds FLNA, in particular human FLNA. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., Gene 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in Wittrup et al. (U.S. Pat. No. 6,699,658) incorporated herein by reference.

5. Recombinant Anti-FLNA Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

The invention features in certain embodiments an isolated nucleic acid encoding a binding protein amino acid sequence as described herein. The invention also features in other certain embodiments, an isolated nucleic acid encoding an antibody construct amino acid sequence as described herein. In methods of production, an expression vector comprises the isolated nucleic acid. Non-limiting examples of such expression vectors are the pUC series of vectors (Fermentas Life Sciences), the pBluescript series of vectors (Stratagene, La Jolla, Calif.), the pET series of vectors (Novagen, Madison, Wis.), the pGEX series of vectors (Pharmacia Biotech, Uppsala, Sweden), and the pEX series vectors (Clontech, Palo Alto, Calif.).

A host cell comprises the vector described herein. According to embodiments of the invention, the host cell is a prokaryotic cell or a eukaryotic cell. For example, the prokaryotic host cells is *E. coli*. The eukaryotic cell may be selected from a protist cell, an animal cell, a plant cell or a fungal cell. The animal cell may be selected from a mammalian cell, an avian cell, and an insect cell. Preferably, the host cell is selected from a CHO cell, a COS cell, a yeast cell, and an insect Sf9 cell. In further related embodiments, the yeast cell is *Saccharomyces cerevisiae*.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.*

159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Also contemplated by the present invention are various methods of production of a protein capable of binding FLNA or of production of an antibody, or antigen binding portion thereof that binds FLNA, comprising culturing a host cell as described herein in culture medium so that the nucleic acid is expressed and the antibody is produced. An exemplary method of producing a protein capable of binding FLNA comprises culturing a host cell as described herein in culture medium under conditions sufficient to produce a binding protein capable of binding FLNA.

The invention also features a protein produced according to said methods.

6. Humanized Anti FLNA Antibodies

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed at the following websites, e.g., ncbi.nlm.nih.gov/entrez-/query.fcgi; atcc.org/phage/hdb.html; sciquest.com/; abcam.com/; antibodyresource.com/onlinecomp.html; public.iastate.edu/.about.pedro/research_tools.html; mgen.uni-heidelberg.de/SD/IT/IT.html; whfreeman.com/immunology/CH-05/kuby05.htm; library.thinkquest.org/12429/Immune/Antibody.html; hhmi org/grants/lectures/1996/vlab/; path.cam.ac.uk/.about.mrc7/m-ikeimages.html; antibodyresource.com/; mcb.harvard.edu/BioLinks/Immuno-logy; immunologylink.com/; pathbox.wustl.edu/.about.hcenter/index.-html; biotech.ufl.edu/.about.hcl/; pebio.com/pa/340913/340913.html-; nal.usda.gov/awic/pubs/antibody/; m.ehime-u.acjp/.about.yasuhito-/Elisa.html; biodesign.com/table.asp; icnet.uk/axp/facs/davies/lin-ks.html; biotech.ufl.edu/.about.fccl/protocol.html; isac-net.org/sites_geo.html; aximtl.imt.uni-marburg.deLabout.rek/AEP-Start.html; baserv.uci.kun.nl/.about.jraats/linksl html; recab.uni-hd.de/immuno.bme.nwu.edu/; mrc-cpe.cam.ac.uk/imt-doc/pu-blic/INTRO.html; ibt.unam.mx/vir/V_mice.html; imgt.cnusc.fr:8104/; biochem.ucl.ac.uk/.about.martin/abs/index.html; antibody.bath.ac.uk/; abgen.cvm.tamu.edu/lab/wwwabgen.html; unizh ch/.about.honegger/AHOsem-inar/Slide01.html; cryst.bbk.ac.uk/.about.ubcg07s/; nimr mrc.ac.uk/CC/ccaewg/ccaewg.htm; path.cam.ac.uk/.about.mrc7/h-umanisation/TAHHP.html; ibt.unam.mx/vir/structure/stat_aim.html; biosci.missouri.edu/smithgp/index.html; cryst.bioc.cam.ac.uk/.about.fmolina/Web-pages/Pept/spottech.html; jerini.de/fr roducts.htm; patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, each entirely incorporated herein by reference, included references cited therein.

Humanized anti-FLNA antibodies are contemplated by the present invention.

7. Additional Competing Antibodies

The term "competing antibodies" herein refers to any number of antibodies targeting the same molecular or stably but non-covalently linked supermolecular entity, preferably the same molecule, i.e., PRLR, wherein at least one is capable of specifically reducing the measurable binding of another, preferably by sterically hampering the other's access to its target epitope or by inducing and/or stabilizing a conformation in the target entity that reduces the target's affinity for the other antibody, more preferably by directly blocking access to the other's target epitope by binding to an epitope in sufficiently close vicinity of the former, overlapping with the former or identical to the former, most preferably overlapping or identical, in particular identical. Two epitopes are herein said to be "overlapping" if they share part of their chemical structures, preferably their amino acid sequences, and to be "identical", if their chemical structures, preferably their amino acid sequences, are identical.

In particular embodiments, the competing antibody, or antigen binding portion thereof, is an antibody, or antigen binding portion thereof, that competes with any one of the FLNA antibody constructs described herein.

8. FLNA Epitopes

In another aspect, the invention pertains to a binding protein, e.g., antibody, or antigen binding fragment thereof, capable of binding FLNA that binds to an epitope in FLNA comprising three, four, five, six, seven, or all of the amino acid residues of the motif ERPLVGV (SEQ ID NO: 42), corresponding to residue 1774-1780 in the hinge connecting Filamin domains 15 and 16 of the target protein. In one embodiment, the binding protein, e.g., antibody, or antigen binding fragment thereof, capable of binding FLNA, binds to an epitope, wherein the epitope comprises all of the amino acid residues. In other embodiments, the binding protein, e.g., antibody, or antigen binding fragment thereof, capable of binding FLNA, binds to a conformational epitope.

In a particular embodiment, the binding protein that binds to said epitope is an antibody, or antigen binding portion thereof.

B. Anti FLNA Antibodies

The present invention features binding proteins comprising an antigen binding domain, said binding protein capable of binding filamin A (FLNA).

A list of amino acid sequences of VH and VL regions of preferred anti-FLNA monoclonal antibodies of the invention are shown below. The CDRs, as determined by the IMGT numbering system (Lefranc, M.-P. et al., Nucleic Acids Research, 27, 209-212 (1999)), are underlined, and also shown below in Table 1.

TABLE 1

List of Amino Acid Sequences of VH and VL regions

| SEQ ID No. | Clone-Protein | Sequence |
|---|---|---|
| 1 | 2C12 VH | QVQLKQSGPGLVQPSQS LSITCTVSGFSLTNYGV HWVRQSPGKGLEWLGVI WRGGSTDYNAAFMSRLS ITKDNSKSQVFFKMNSL QADDTAIYFCALRGNYV HYYLMDYWGQGTSVTVS S |
| 7 | 2C12 VH CDR1 | GFSLTNYG |
| 8 | 2C12 VH CDR2 | IWRGGST |
| 9 | 2C12 VH CDR3 | ALRGNYVHYYLMDY |
| 2 | 2C12 VL | DIQVTQTPSSLSASLGD RVTISCRASQDISNYLN WYQQKPDGTVKLLIYYT SRLHSGVPSRFSGSGSG TDYSLTISNLDQEDIAT YFCQQGNTLPPTFGGGT NLEIK |
| 10 | 2C12 VL CDR1 | QDISNY |
| 11 | 2C12 VL CDR2 | YTS |
| 12 | 2C12 VL CDR3 | QQGNTLPPT |
| 3 | 3F4 VH | EVQLQESGPGLAKPSQT LSLTCSVTGYSITSNYW NWIRKFPGNKLEYMGYI SFSGSTYYNPSLKSRIS ITRDTSKNQYYLQLNSV TTEDTATYYCARWNYYA MDYWGQGTSVTVSS |
| 13 | 3F4 VH CDR1 | GYSITSNY |
| 14 | 3F4 VH CDR2 | ISFSGST |
| 15 | 3F4 VH CDR3 | ARWNYYAMDY |
| 4 | 3F4 VL | DFLLTQSPAILSVSPGE RVSFSCRASQSIGTNIH WYQQRTNGSPRLLIKFA SESISGIPSRFSGSGSG TDFTLTINSVESEDIAD YYCQQSNSWPYTFGGGT KLEIK |
| 16 | 3F4 VL CDR1 | QSIGTN |
| 17 | 3F4 VL CDR2 | FAS |
| 18 | 3F4 VL CDR3 | QQSNSWPYT |
| 5 | 6E3 VH | QVQLQQSGAELMKPGAS VKLSCKATGYTFTGYWI EWVKQRPGHGLEWIGEI LPGNGSTNCNEKFKGKA TFTATTSSNTAYMQLSS LTTEDSAIYYCTTVSYW GQGTTLTVSS |
| 19 | 6E3 VH CDR1 | GYTFTGYW |
| 20 | 6E3 VH CDR2 | ILPGNGST |

TABLE 1-continued

List of Amino Acid Sequences of VH and VL regions

| SEQ ID No. | Clone-Protein | Sequence |
|---|---|---|
| 21 | 6E3 VH CDR3 | TTVSY |
| 6 | 6E3 VL | DVVMTQTPLSLPVSLGD QASISCRSSQSLVHSNG NTYLHWYLQKPGQSPNL LIYKVSNRFSGVPDRFT GSGSGTDFTLKISRVEA EDLGVYFCSQSTHVPFT FGSGTKLEIK |
| 22 | 6E3 VL CDR1 | QSLVHSNGNTY |
| 23 | 6E3 VL CDR2 | KVS |
| 24 | 6E3 VL CDR3 | SQSTHVPFT |

The present invention features binding proteins, for example antibodies, and fragments thereof, comprising an antigen binding domain, said binding protein capable of binding filamin A (FLNA). In one aspect, the present invention features a binding protein comprising an antigen binding domain, said binding protein capable of binding filamin A (FLNA), said antigen binding domain comprising a heavy chain CDR3 domain comprising the amino acid sequence selected from the group consisting of SEQ ID NO: 9, SEQ ID NO: 15 or SEQ ID NO: 21.

In one embodiment, the binding protein further comprises a heavy chain CDR2 domain comprising the amino acid sequence selected from the group consisting of SEQ ID NO: 8, SEQ ID NO: 14 or SEQ ID NO: 20. In another embodiment, the binding protein further comprises a heavy chain CDR1 domain comprising the amino acid sequence selected from the group consisting of SEQ ID NO: 7, SEQ ID NO: 13 or SEQ ID NO: 19.

In one embodiment, the binding protein further comprises a light chain CDR3 domain comprising the amino acid sequence selected from the group consisting of SEQ ID NO: 12, SEQ ID NO: 18 or SEQ ID NO: 24. In another embodiment, the binding protein further comprises a light chain CDR2 domain comprising the amino acid sequence selected from the group consisting of SEQ ID NO: 11, SEQ ID NO: 17 or SEQ ID NO: 23. In another embodiment, the binding protein further comprises a light chain CDR1 domain comprising the amino acid sequence selected from the group consisting of SEQ ID NO: 10, SEQ ID NO: 16 or SEQ ID NO: 22.

The present invention also features in other aspects, a binding protein comprising an antigen binding domain, said binding protein capable of binding filamin A (FLNA), said antigen binding domain comprising a heavy chain variable region comprising a CDR3 domain comprising the amino acid sequence set forth in SEQ ID NO: 9, a CDR2 domain comprising the amino acid sequence set forth in SEQ ID NO: 8, and a CDR1 domain comprising the amino acid sequence set forth in SEQ ID NO: 7 or a heavy chain variable region comprising a CDR3 domain comprising the amino acid sequence set forth in SEQ ID NO: 15, a CDR2 domain comprising the amino acid sequence set forth in SEQ ID NO: 14, and a CDR1 domain comprising the amino acid sequence set forth in SEQ ID NO: 13 or a heavy chain variable region comprising a CDR3 domain comprising the amino acid sequence set forth in SEQ ID NO: 21, a CDR2 domain comprising the amino acid sequence set forth in SEQ ID NO: 20, and a CDR1 domain comprising the amino acid sequence set forth in SEQ ID NO: 19; and a light chain variable region comprising a CDR3 domain comprising the amino acid sequence set forth in SEQ ID NO: 12, a CDR2 domain comprising the amino acid sequence set forth in SEQ ID NO: 11, and a CDR1 domain comprising the amino acid sequence set forth in SEQ ID NO: 10 or a light chain variable region comprising a CDR3 domain comprising the amino acid sequence set forth in SEQ ID NO: 18, a CDR2 domain comprising the amino acid sequence set forth in SEQ ID NO: 17, and a CDR1 domain comprising the amino acid sequence set forth in SEQ ID NO: 16 or a light chain variable region comprising a CDR3 domain comprising the amino acid sequence set forth in SEQ ID NO: 24, a CDR2 domain comprising the amino acid sequence set forth in SEQ ID NO: 23, and a CDR1 domain comprising the amino acid sequence set forth in SEQ ID NO: 22.

The present invention also features in other aspects, a binding protein comprising an antigen binding domain, said binding protein capable of binding filamin A (FLNA), said antigen binding domain comprising a heavy chain variable region comprising a CDR3 domain comprising the amino acid sequence of SEQ ID NO: 9, a CDR2 domain comprising the amino acid sequence of SEQ ID NO: 8, and a CDR1 domain comprising the amino acid sequence of SEQ ID NO: 7, and a light chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10.

The present invention also features in other aspects, a binding protein comprising an antigen binding domain, said binding protein capable of binding filamin A (FLNA), said antigen binding domain comprising a heavy chain variable region comprising a CDR3 domain comprising the amino acid sequence of SEQ ID NO: 15, a CDR2 domain comprising the amino acid sequence of SEQ ID NO: 14, and a CDR1 domain comprising the amino acid sequence of SEQ ID NO: 13, and a light chain variable region comprising a CDR3 domain comprising the amino acid sequence of SEQ ID NO: 18, a CDR2 domain comprising the amino acid sequence of SEQ ID NO: 17, and a CDR1 domain comprising the amino acid sequence of SEQ ID NO: 16.

The present invention also features in other aspects, a binding protein comprising an antigen binding domain, said binding protein capable of binding filamin A (FLNA), said antigen binding domain comprising a heavy chain variable region comprising a CDR3 domain comprising the amino acid sequence of SEQ ID NO: 21, a CDR2 domain comprising the amino acid sequence of SEQ ID NO: 20, and a CDR1 domain comprising the amino acid sequence of SEQ ID NO: 19, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22.

In one embodiment of the above aspects, the antigen binding domain comprises a heavy chain variable region selected from the group consisting of: the amino acid sequence set forth in SEQ ID NO: 1, the amino acid sequence set forth in SEQ ID NO: 3 or the amino acid sequence set forth in SEQ ID NO: 5.

In another embodiment of the above aspects, the antigen binding domain comprises a light chain variable region selected from the group consisting of: the amino acid sequence set forth in SEQ ID NO: 2, the amino acid sequence set forth in SEQ ID NO: 4 or the amino acid set forth in SEQ ID NO: 6.

In one embodiment of the above aspects, the antigen binding domain comprises a heavy chain variable region comprising the amino acid sequence set forth in SEQ ID NO: 1 and a light chain variable region comprising the amino acid sequence set forth in SEQ ID NO: 2.

In another embodiment of the above aspects, the antigen binding domain comprises a heavy chain variable region comprising the amino acid sequence set forth in SEQ ID NO: 3 and a light chain variable region comprising the amino acid sequence set forth in SEQ ID NO: 4.

In another embodiment of the above aspects, the antigen binding domain comprises a heavy chain variable region comprising the amino acid sequence set forth in SEQ ID NO: 5 and a light chain variable region comprising the amino acid sequence set forth in SEQ ID NO: 6.

In certain embodiments, the term "2C12" refers to a hybridoma that produces an antibody comprising (i) one variable heavy chain having an amino acid sequence comprising SEQ ID NO:1; and (ii) one variable light chain having an amino acid sequence comprising SEQ ID NO:2. In certain embodiments, the 2C12 heavy chain variable region comprises a CDR3 domain comprising the amino acid sequence of SEQ ID NO: 9, a CDR2 domain comprising the amino acid sequence of SEQ ID NO: 8, and a CDR1 domain comprising the amino acid sequence of SEQ ID NO: 7, and the light chain variable region comprises a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10. In certain embodiments, antibody 2C12 can have an on rate constant ($K_{ON}$) to FLNA of at least about $1\times10^4$ $M^{-1}$ $s^{-1}$ to about $6\times10^6$ $M^{-1}$ $s^{-1}$ or about $5\times10^4$ $M^{-1}$ $s^{-1}$ to about $9\times10^5$ $M^{-1}$ $s^{-1}$ as measured by surface plasmon resonance. In other embodiments, the binding protein according to the present invention can have an on rate constant ($K_{ON}$) to FLNA of least about $7.9\times10^4$ $M^{-1}$ $s^{-1}$ as measured by surface plasmon resonance. In other embodiments, the binding protein according to the present invention can have a dissociation constant ($K_D$) to FLNA of $4.82\times10^{-9}$ $s^{-1}$ or less. In certain preferred embodiments, the binding protein according to the present invention has a dissociation constant ($K_D$) to FLNA of about $1.0\times10^{-7}$ $s^{-1}$ or less, or about $1\times10^{-8}$ M or less. According to preferred embodiments of the invention, the isotype of the antibody construct produced by the 2C12 hybridoma clone is IgG1/κ.

In other certain embodiments, the term "3F4" refers to a hybridomas that produces an antibody comprising (i) one variable heavy chain having an amino acid sequence comprising SEQ ID NO:3; and (ii) one variable light chain having an amino acid sequence comprising SEQ ID NO:4. In certain embodiments, the 3F4 heavy chain variable region comprises a CDR3 domain comprising the amino acid sequence of SEQ ID NO: 15, a CDR2 domain comprising the amino acid sequence of SEQ ID NO: 14, and a CDR1 domain comprising the amino acid sequence of SEQ ID NO: 13, and the light chain variable region comprises a CDR3 domain comprising the amino acid sequence of SEQ ID NO: 18, a CDR2 domain comprising the amino acid sequence of SEQ ID NO: 17, and a CDR1 domain comprising the amino acid sequence of SEQ ID NO: 16. In certain embodiments, the antibody 3F4 can have an on rate constant ($K_{ON}$) to FLNA of at least about $1\times10^4$ $M^{-1}$ $s^{-1}$ to about $6\times10^6$ $M^{-1}$ $s^{-1}$ or about $5\times10^4$ $M^{-1}$ $s^{-1}$ to about $9\times10^5$ $M^{-1}$ $s^{-1}$ as measured by surface plasmon resonance. In other embodiments, the binding protein according to the present invention can have an on rate constant ($K_{ON}$) to FLNA of at least about $8.05\times10^5$ $M^{-1}$ $s^{-1}$ as measured by surface plasmon resonance. In other embodiments, the binding protein according to the present invention can have a dissociation constant ($K_D$) to FLNA of $9.99\times10^{40}$ $s^{-1}$ or less. In certain preferred embodiments, the binding protein according to the present invention has a dissociation constant ($K_D$) to FLNA of about $1.0\times10^{-7}$ $s^{-1}$ or less, or about $1\times10^{-8}$ M or less. According to other preferred embodiments of the invention, the isotype of the antibody construct produced by the 3F4 hybridoma clone is IgG2B/κ.

In other certain embodiments, the term "6E3" refers to a hybridomas that produces an antibody comprising (i) one variable heavy chain having an amino acid sequence comprising SEQ ID NO:5; and (ii) one variable light chain having an amino acid sequence comprising SEQ ID NO:6. In certain embodiments, the 6E3 heavy chain variable region comprises a CDR3 domain comprising the amino acid sequence of SEQ ID NO: 21, a CDR2 domain comprising the amino acid sequence of SEQ ID NO: 20, and a CDR1 domain comprising the amino acid sequence of SEQ ID NO: 19, and the light chain variable region comprises a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22. In certain embodiments, antibody 6E3 can have an on rate constant ($K_{ON}$) to FLNA of at least about $1\times10^4$ $M^{-1}$ $s^{-1}$ to about $6\times10^6$ $M^{-1}$ $s^{-1}$ or about $5\times10^4$ $M^{-1}$ $s^{-1}$ to about $9\times10^5$ $M^{-1}$ $s^{-1}$ as measured by surface plasmon resonance. In other embodiments, the binding protein according to the present invention can have an on rate constant ($K_{ON}$) to FLNA of at least about $1.95\times10^5$ $M^{-1}$ $s^{-1}$ as measured by surface plasmon resonance. In other embodiments, the binding protein according to the present invention can have a dissociation constant ($K_D$) to FLNA of $4.09\times10^{-9}$ $s^{-1}$ or less. In certain preferred embodiments, the binding protein according to the present invention has a dissociation constant ($K_D$) to FLNA of about $1.0\times10^{-7}$ $s^{-1}$ or less, or about $1\times10^{-8}$ M or less. According to other preferred embodiments of the invention, the isotype of the antibody construct produced by the 6E3 hybridoma clone is IgG1/κ.

In one embodiment, the antigen binding domain comprises a heavy chain comprising the amino acid sequence set forth in SEQ ID NO: 25, and a light chain comprising the amino acid sequence set forth in SEQ ID NO: 26.

In another embodiment, the antigen binding domain comprises a heavy chain comprising the amino acid sequence set forth in SEQ ID NO: 27, and a light chain comprising the amino acid sequence set forth in SEQ ID NO: 28.

In another embodiment, the antigen binding domain comprises a heavy chain comprising the amino acid sequence set forth in SEQ ID NO: 29, and a light chain comprising the amino acid sequence set forth in SEQ ID NO: 30.

In certain embodiments, the heavy chain consensus amino acid sequence produced by the 2C12 hybridoma comprises SEQ ID NO: 25, shown below. In SEQ ID NO:25, the variable heavy domain is highlighted in bold.

SEQ ID NO: 25
MAVLGLLFCLVTFPSCVLSQVQLKQSGPGLVQPSQSLSITCTVSGFSLTN

YGVHWVRQSPGKGLEWLGVIWRGGSTDYNAAFMSRLSITKDNSKSQVFFK

MNSLQADDTAIYFCALRGNYVHYYLMDYWGQGTSVTVSSAKTTPPSVYPL

AP

In certain embodiments, the light chain consensus amino acid sequence produced by the 2C12 hybridoma comprises SEQ ID NO: 26, shown below. In SEQ ID NO:26, the variable light domain is highlighted in bold.

SEQ ID NO: 26
MVSTAQFLGLLLLCFQGTRCDIQVTQTPSSLSASLGDRVTISCRASQDIS

NYLNWYQQKPDGTVKLLIYYTSRLHSGVPSRFSGSGSGTDYSLTISNLDQ

EDIATYFCQQGNTLPPTFGGGTNLEIKRADAAPTVSIFPPSSEQLTSGGA

SVVCFLNNFYPK

In certain embodiments, the heavy chain consensus amino acid sequence produced by the 3F4 hybridoma comprises SEQ ID NO: 27, shown below. In SEQ ID NO:27, the variable heavy domain is highlighted in bold.

SEQ ID NO: 27
MMVLSLLYLLTALPGILSEVQLQESGPGLAKPSQTLSLTCSVTGYSITSN

YWNWIRKFPGNKLEYMGYISFSGSTYYNPSLKSRISITRDTSKNQYYLQL

NSVTTEDTATYYCARWNYYAMDYWGQGTSVTVSSAKTTPPSVFPLA

In certain embodiments, the light chain consensus amino acid sequence produced by the 3F4 hybridoma comprises SEQ ID NO: 28, shown below. In SEQ ID NO:28, the variable light domain is highlighted in bold.

SEQ ID NO: 28
MVSTAQFLVFLLFWIPASRGDFLLTQSPAILSVSPGERVSFSCRASQSIG

TNIHWYQQRTNGSPRLLIKFASESISGIPSRFSGSGSGTDFTLTINSVES

EDIADYYCQQSNSWPYTFGGGTKLEIKRADAAPTVSIFPPSSEQLTSGGA

SVVCFLNNFYPR

In certain embodiments, the heavy chain consensus amino acid sequence produced by the 6E3 hybridoma comprises SEQ ID NO: 29, shown below. In SEQ ID NO:29, the variable heavy domain is highlighted in bold.

SEQ ID NO: 29
MGWSWVMLFLLSVTAGVHSQVQLQQSGAELMKPGASVKLSCKATGYTFTG

YWIEWVKQRPGHGLEWIGEILPGNGSTNCNEKFKGKATFTATTSSNTAYM

QLSSLTTEDSAIYYCTTVSYWGQGTTLTVSSAKTTPPSVFPLA

In certain embodiments, the light chain consensus amino acid sequence produced by the 6E3 hybridoma comprises SEQ ID NO: 30, shown below. In SEQ ID NO:30, the variable light domain is highlighted in bold.

SEQ ID NO: 30
MKLPVRLLVLMFWIPASTSDVVMTQTPLSLPVSLGDQASISCRSSQSLVH

SNGNTYLHWYLQKPGQSPNLLIYKVSNRFSGVPDRFTGSGSGTDFTLKIS

RVEAEDLGVYFCSQSTHVPFTFGSGTKLEIKRADAAPTVSIFPPSSEQLT

SGGASVVCFLNNFYPK

According to preferred embodiments of the present invention, the binding protein as described herein is an antibody.

Accordingly, the present invention features an antibody construct comprising a binding protein as described herein, wherein the antibody construct further comprises a linker polypeptide or an immunoglobulin constant domain.

The antibody construct according the present invention may comprise a heavy chain immunoglobulin constant domain selected from the group consisting of a IgM constant domain, a IgG4 constant domain, a IgG1 constant domain, a IgE constant domain, a IgG2 constant domain, a IgG3 constant domain and a IgA constant domain.

In certain embodiments, the binding protein comprises an IgG1 constant domain. In other embodiments, the binding protein comprises an IgG2 constant region, preferably IgG2b.

Furthermore, the antibody can comprise a light chain constant region, either a kappa light chain constant region or a lambda light chain constant region. Preferably, the antibody comprises a kappa light chain constant region. According to preferred embodiments of the invention, the isotype of the antibody construct produced by the 2C12 hybridoma clone is IgG1/κ. According to other preferred embodiments of the invention, the isotype of the antibody construct produced by the 3F4 hybridoma clone is IgG2B/κ. According to other preferred embodiments of the invention, the isotype of the antibody construct produced by the 6E3 hybridoma clone is IgG1/κ.

In certain embodiments, the binding protein according to the present invention can have an on rate constant ($K_{ON}$) to FLNA of at least about $1 \times 10^4$ $M^{-1}$ $s^{-1}$ to about $6 \times 10^6$ $M^{-1}$ $s^{-1}$ or about $5 \times 10^4$ $M^{-1}$ $s^{-1}$ to about $9 \times 10^5$ $M^{-1}$ $s^{-1}$. In other embodiments, the binding protein according to the present invention can have an on rate constant ($K_{ON}$) to FLNA selected from the group consisting of at least about $7.9 \times 10^4$ $M^{-1}$ $s^{-1}$, at least about $8.05 \times 10^5$ $M^{-1}$ $s^{-1}$, and at least about $1.95 \times 10^5$ $M^{-1}$ $s^{-1}$ as measured by surface plasmon resonance.

In other embodiments, the binding protein according to the present invention can have a dissociation constant ($K_D$) to FLNA selected from the group consisting of $4.82 \times 10^{-9}$ $s^{-1}$ or less, $9.99 \times 10^{-10}$ $s^{-1}$ or less and $4.09 \times 10^{-9}$ $s^{-1}$ or less. In certain preferred embodiments, the binding protein according to the present invention has a dissociation constant ($K_D$) to FLNA of about $1.0 \times 10^{-7}$ $s^{-1}$ or less, or about $1 \times 10^{-8}$ M or less.

The binding protein can be selected from an immunoglobulin molecule, a monoclonal antibody, a murine antibody, a chimeric antibody, a CDR-grafted antibody, a humanized antibody, a single domain antibody, a Fv, a disulfide linked Fv, a scFv, a diabody, a Fab, a Fab', a F(ab')2, a multispecific antibody, a dual specific antibody, and a bispecific antibody.

Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to one or more functional molecule(s) (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

II. Uses of Anti-FLNA Antibodies

A. Detection

Given their ability to bind to FLNA, in particular human FLNA, the anti-FLNA antibodies, or portions thereof, of the invention can be used to detect FLNA (e.g., in a biological sample, such as serum, plasma, tissues or cells), using a conventional immunoassay, such as an enzyme linked immunosorbent assays (ELISA), a radioimmunoassay (RIA), antibody-labeled fluorescence imaging, or tissue immunohistochemistry. It is understood that the invention includes the use of any fragments of filamin A polypeptide as long as the fragment allows for the specific identification of filamin A by a detection method of the invention. For example, an ELISA antibody must be able to bind to the filamin A fragment so that detection is possible.

In one exemplary ELISA, antibodies binding to FLNA are immobilized onto a selected surface exhibiting protein affinity, such as a well in a polystyrene microtiter plate. Then, a test composition suspected of containing the prostate cancer marker antigen, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label.

In another exemplary ELISA, the samples suspected of containing FLNA are immobilized onto the well surface and then contacted with anti-FLNA antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Irrespective of the format employed, ELISAs have certain features in common, such as coating, incubating or binding, washing to remove non-specifically bound species, and detecting the bound immunecomplexes. These are described as follows.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human prostate, cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

The phrase "under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25 to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple. Quantitation is then achieved by measuring the degree of color generation, e.g., using a visible spectra spectrophotometer.

In certain embodiments, an alternative approach for detection of FLNA using the anti-FLNA antibodies of the invention is employing protein immunoprecipitation combined with multiple reaction monitoring mass spectrometry (IPMRM). IPMRM is known in the art and is described, for example, in Lin et al. (Journal of Proteome Research, 2013, 12, 5996-6003) and Ravipaty et al. (J. Mol. Biomark Diagn), 2017, vol. 8, issue 2), the contents of which are expressly incorporated herein by reference.

B. Labeling

The invention provides a method for detecting FLNA in a biological sample comprising contacting a biological sample with an antibody, or antibody portion, of the invention and detecting either the antibody (or antibody portion) bound to FLNA or unbound antibody (or antibody portion), to thereby detect FLNA in the biological sample. The antibody is directly or indirectly labeled with a detectable substance to facilitate detection of the bound or unbound antibody.

Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

One skilled in the art will recognize that many strategies can be used for labeling target molecules to enable their detection or discrimination in a mixture of particles (e.g., labeled anti-filamin A antibodies as described herein). The labels may be attached by any known means, including methods that utilize non-specific or specific interactions of label and target. Labels may provide a detectable signal or affect the mobility of the particle in an electric field. In addition, labeling can be accomplished directly or through binding partners.

In some embodiments, the label comprises a binding partner, e.g. a FLNA antibody as described herein, that binds to FLNA, where the binding partner is attached to a fluorescent moiety. The compositions and methods of the invention may utilize highly fluorescent moieties, e.g., a moiety capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. Moieties suitable for the compositions and methods of the invention are described in more detail below.

In some embodiments, the invention provides a label for detecting a biological molecule comprising a binding partner for the biological molecule, e.g. a FLNA antibody as described herein, that is attached to a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the moiety comprises a plurality of fluorescent entities, e.g., about 2 to 4, 2 to 5, 2 to 6, 2 to 7, 2 to 8, 2 to 9, 2 to 10, or about 3 to 5, 3 to 6, 3 to 7, 3 to 8, 3 to 9, or 3 to 10 fluorescent entities. In some embodiments, the moiety comprises about 2 to 4 fluorescent entities. The fluorescent entities can be fluorescent dye molecules. In some embodiments, the fluorescent dye molecules comprise at least one substituted indolium ring system in which the substituent on the 3-carbon of the indolium ring contains a chemically reactive group or a conjugated substance. In some embodiments, the dye molecules are Alexa Fluor molecules selected from the group consisting of Alexa Fluor 488, Alexa Fluor 532, Alexa Fluor 647, Alexa Fluor 680 or Alexa Fluor 700. In some embodiments, the dye molecules are Alexa Fluor molecules selected from the group consisting of Alexa Fluor 488, Alexa Fluor 532, Alexa Fluor 680 or Alexa Fluor 700. In some embodiments, the dye molecules are Alexa Fluor 647 dye molecules. In some embodiments, the dye molecules comprise a first type and a second type of dye molecules, e.g., two different Alexa Fluor molecules, e.g., where the first type and second type of dye molecules have different emission spectra. The ratio of the number of first type to second type of dye molecule can be, e.g., 4 to 1, 3 to 1, 2 to 1, 1 to 1, 1 to 2, 1 to 3 or 1 to 4. The binding partner can be, e.g. a FLNA antibody as described herein.

In some embodiments, the invention provides a label for the detection of FLNA, wherein the label comprises a binding partner for the marker and a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the fluorescent moiety comprises a fluorescent molecule. In some embodiments, the fluorescent moiety comprises a plurality of fluorescent molecules, e.g., about 2 to 10, 2 to 8, 2 to 6, 2 to 4, 3 to 10, 3 to 8, or 3 to 6 fluorescent molecules. In some embodiments, the label comprises about 2 to 4 fluorescent molecules. In some embodiments, the fluorescent dye molecules comprise at least one substituted indolium ring system in which the substituent on the 3-carbon of the indolium ring contains a chemically reactive group or a conjugated substance. In some embodiments, the fluorescent molecules are selected from the group consisting of Alexa Fluor 488, Alexa Fluor 532, Alexa Fluor 647, Alexa Fluor 680 or Alexa Fluor 700. In some embodiments, the fluorescent molecules are selected from the group consisting of Alexa Fluor 488, Alexa Fluor 532, Alexa Fluor 680 or Alexa Fluor 700. In some embodiments, the fluorescent molecules are Alexa Fluor 647 molecules. In some embodiments, the binding partner comprises an anti-FLNA antibody as described herein.

Alternative to labeling the antibody, FLNA can be assayed in biological fluids by a competition immunoassay utilizing FLNA standards labeled with a detectable substance and an unlabeled FLNA antibody. In this assay, the biological sample, the labeled FLNA standards and the FLNA antibody are combined and the amount of labeled standard bound to the unlabeled antibody is determined. The amount of FLNA in the biological sample is inversely proportional to the amount of labeled standard bound to the anti-FLNA antibody. Similarly, FLNA can also be assayed in biological fluids by a competition immunoassay utilizing FLNA standards labeled with a detectable substance and an unlabeled FLNA antibody.

C. Diagnostic and Prognostic Uses of the Invention

The invention provides methods for diagnosing an abnormal prostate state, e.g., BPH or an oncological disease state, e.g., prostate cancer, in a subject. The invention further provides methods for prognosing or monitoring progression or monitoring response of an abnormal prostate state, e.g., BPH or prostate cancer, to a therapeutic treatment during active treatment or during watchful waiting. In one embodiment, the invention provides methods for diagnosis of prostate cancer versus benign prostatic hyperplasia (BPH) in a subject, e.g., using one or more marker described herein.

As used herein the disorder, disease, or abnormal state is an abnormal prostate state, including benign prostate hyperplasia and cancer, particularly prostate cancer. Abnormal prostate states can be classified as one or more of benign prostate hyperplasia (BPH), androgen sensitive prostate cancer, androgen insensitive or resistant prostate cancer, aggressive prostate cancer, non-aggressive prostate cancer, metastatic prostate cancer, and non-metastatic prostate cancer. Further, the prostate cancer may be a prostatic intraepithelial neoplasia, adenocarcinoma, small cell carcinoma, or squamous cell carcinoma.

The invention provides, in one embodiment, methods for diagnosing an oncological disorder, e.g., prostate cancer. The methods of the present invention can be practiced in conjunction with any other method used by the skilled practitioner to provide a prognosis of the occurrence or recurrence of an oncologic disorder and/or the survival of a subject being treated for an oncologic disorder. The diagnostic and prognostic methods provided herein can be used to determine if additional and/or more invasive tests or monitoring should be performed on a subject. It is understood that a disease as complex as an oncological disorder is rarely diagnosed using a single test. Therefore, it is understood that the diagnostic, prognostic, and monitoring methods provided herein are typically used in conjunction with other methods known in the art. For example, the methods of the invention may be performed in conjunction with a morphological or cytological analysis of the sample obtained from the subject, imaging analysis, and/or physical exam. Cytological methods would include immunohistochemical or immunofluorescence detection (and quantitation if appropriate) of any other molecular marker either by itself, in conjunction with other markers. Other methods would include detection of other markers by in situ PCR, or by extracting tissue and quantitating other markers by real time PCR. PCR is defined as polymerase chain reaction.

Methods for assessing tumor progression during watchful waiting or the efficacy of a treatment regimen, e.g., chemotherapy, radiation therapy, e.g., radiation of the prostate, surgery, e.g., surgical prostate resection, hormone therapy, or any other therapeutic approach useful for treating an oncologic disorder in a subject are also provided. In these methods the amount of marker in a pair of samples (a first sample obtained from the subject at an earlier time point or prior to the treatment regimen and a second sample obtained from the subject at a later time point, e.g., at a later time point when the subject has undergone at least a portion of the treatment regimen) is assessed. It is understood that the methods of the invention include obtaining and analyzing more than two samples (e.g., 3, 4, 5, 6, 7, 8, 9, or more samples) at regular or irregular intervals for assessment of marker levels. Pairwise comparisons can be made between consecutive or non-consecutive subject samples. Trends of marker levels and rates of change of marker levels can be analyzed for any two or more consecutive or non-consecutive subject samples.

The invention also provides a method for determining whether an oncologic disorder, e.g., prostate cancer, is aggressive. The method comprises determining the amount of a marker present in a sample and comparing the amount to a control amount of the marker present in one or more control samples, as defined in Definitions, thereby determining whether an oncologic disorder is aggressive. Marker levels can be compared to marker levels in samples obtained at different times from the same subject or marker levels from normal or abnormal prostate state subjects. A rapid increase in the level of marker may be indicative of a more aggressive cancer than a slow increase or no increase or change in the marker level.

The methods of the invention may also be used to select a compound that is capable of modulating, i.e., decreasing, the aggressiveness of an oncologic disorder, e.g., prostate cancer. In this method, a cancer cell is contacted with a test compound, and the ability of the test compound to modulate the expression and/or activity of a marker in the invention in the cancer cell is determined, thereby selecting a compound that is capable of modulating aggressiveness of an oncologic disorder.

Using the methods described herein, a variety of molecules may be screened in order to identify molecules which modulate, e.g., increase or decrease the expression and/or activity of a marker of the invention, i.e., FLNA, optionally in combination with one or more additional markers such as PSA, keratin 19 (KRT19), and/or filamin B (FLNB). Compounds so identified can be provided to a subject in order to inhibit the aggressiveness of an oncologic disorder in the subject, to prevent the recurrence of an oncologic disorder in the subject, or to treat an oncologic disorder in the subject.

In particular embodiments, the invention provides methods for detecting an abnormal prostate state in a subject by contacting a biological sample from a subject with a detection reagent specific for a prostate-cancer related marker, e.g. FLNA; (2) measuring the amount of the prostate-cancer related marker detected in the biological sample by the detection reagent; and (3) comparing the level of expression of the prostate-cancer related marker in the biological sample obtained from the subject with a level of expression of the prostate-cancer related protein in a normal control sample, thereby detecting an abnormal prostate state. In preferred embodiments, the detection reagent is an anti-FLNA antibody, or an antigen-binding portion thereof and the prostate cancer-related marker is FLNA. Optionally, additional prostate cancer-related markers can be detected such as PSA, keratin 19 (KRT19), and/or filamin B (FLNB) in the methods of the invention. In one embodiment, prostate cancer-related markers FLNA, KRT19 and PSA are detected in the methods of the invention. In one embodiment, prostate cancer-related markers FLNA and KRT19 are detected in the methods of the invention. In one embodiment, prostate cancer-related markers FLNA, FLNB and PSA are detected in the methods of the invention. In one embodiment, prostate cancer-related markers FLNA and FLNB are detected in the methods of the invention. Additional markers, including filamin B and keratin 19, and uses thereof in the diagnosis and prognosis of prostate cancer, are described in PCT Publication Nos. WO 2014/004931, filed on Jun. 27, 2013, and WO 2016/094425, filed on Dec. 8, 2015, the contents of which are expressly incorporated herein by reference.

In certain embodiments, detecting an abnormal prostate state comprises diagnosing prostate cancer status in a subject. In certain embodiments, an abnormal prostate state comprises identifying a predisposition to developing prostate cancer.

The invention provides methods for monitoring the treatment of prostate cancer in a subject by (1) contacting a first biological sample obtained from the subject prior to administering at least a portion of a treatment regimen to the subject with a detection reagent specific for a prostate-cancer related protein, e.g. FLNA; (2) contacting a second biological sample obtained from the subject after administering at least a portion of a treatment regimen to the subject with a detection reagent specific for a prostate-cancer related protein, e.g., FLNA; (3) measuring the amount of prostate-cancer related marker detected in each the first biological sample and the second biological sample by each detection reagent; and (4) comparing the level of expression of the prostate-cancer related marker in the first sample with the expression level of the prostate-cancer related marker in the second sample, thereby monitoring the treatment of prostate cancer in the subject. In preferred embodiments, the detection reagent is an anti-FLNA antibody, or an antigen-binding portion thereof and the prostate cancer-related marker is FLNA. Optionally, additional prostate cancer-related markers are detected such as PSA, keratin 19 (KRT19), and/or filamin B (FLNB). In one embodiment, prostate cancer-related markers FLNA, KRT19 and PSA are detected in the methods of the invention. In one embodiment, prostate cancer-related markers FLNA and KRT19 are detected in the methods of the invention. In one embodiment, prostate cancer-related markers FLNA, FLNB and PSA are detected in the methods of the invention. In one embodiment, prostate cancer-related markers FLNA and FLNB are detected in the methods of the invention.

The invention provides method of selecting for administration of active treatment or against administration of active treatment of prostate cancer in a subject by (1) contacting a first biological sample obtained from the subject prior to administering a treatment regimen to the subject with a detection reagent specific for a prostate-cancer related protein, e.g. FLNA; (2) contacting a second biological sample obtained from the subject prior to administering a treatment regimen to the subject with a detection reagent specific for a prostate-cancer related protein; (3) measuring the amount of prostate-cancer related marker detected in each the first biological sample and the second biological sample by each detection reagent; and (4) comparing the level of expression of the prostate-cancer related markers in the first sample with the expression level of the prostate-cancer related markers in the second sample, wherein selecting for administration of active treatment or against administration of active treatment of prostate cancer is based on the presence or absence of changes in the level of expression of one or more markers between the first sample and the second sample. Treatment includes, e.g., chemotherapy, radiation therapy, e.g., radiation of the prostate, surgery, e.g., surgical prostate resection, hormone therapy, or any other therapeutic approach useful for treating an oncologic disorder in a subject. In preferred embodiments, the detection reagent is an anti-FLNA antibody, or an antigen-binding portion thereof and the prostate cancer-related marker is FLNA. Optionally, additional prostate cancer-related markers are detected such as PSA, keratin 19 (KRT19), and/or filamin B (FLNB). In one embodiment, prostate cancer-related markers FLNA, KRT19 and PSA are detected in the methods of the invention. In one embodiment, prostate cancer-related markers FLNA and KRT19 are detected in the methods of the invention. In one embodiment, prostate cancer-related markers FLNA, FLNB and PSA are detected in the methods of the invention. In one embodiment, prostate cancer-related markers FLNA and FLNB are detected in the methods of the invention.

In certain embodiments of the diagnostic methods provided herein, an increase in the level of expression of a prostate-cancer related markers, e.g. FLNA, in the biological sample as compared to the level of expression of the prostate-cancer related markers, e.g. FLNA, in a normal control sample is an indication that the subject is afflicted with prostate cancer. In one embodiment, an increase in the level of expression of prostate cancer-related markers FLNA and KRT19 (and optionally PSA) in the biological sample as compared to the level of expression of FLNA and KRT19 in a normal control sample is an indication that the subject is afflicted with prostate cancer.

In certain embodiments of the diagnostic methods provided herein, no increase in the detected expression level of FLNA in the biological sample as compared to the expression level in a normal control sample is an indication that the subject is not afflicted with prostate cancer or not predisposed to developing prostate cancer. In one embodiment, no increase in the level of expression of prostate cancer-related markers FLNA and KRT19 (and optionally PSA) in the biological sample as compared to the level of expression of FLNA and KRT19 (and optionally PSA) in a normal control sample is an indication that the subject is not afflicted with prostate cancer or not predisposed to developing prostate cancer.

In certain embodiments of the diagnostic methods provided herein, an increase in the level of expression of the prostate-cancer related markers, e.g. FLNA, in the biological sample as compared to the level of expression of the prostate-cancer related markers, e.g. FLNA, in a normal control sample is an indication that the subject is predisposed to developing prostate cancer. In one embodiment, an increase in the level of expression of prostate cancer-related markers FLNA, KRT19 and PSA in the biological sample as compared to the level of expression of FLNA, KRT19 and PSA in a normal control sample is an indication that the subject is predisposed to developing prostate cancer.

In certain embodiments of the monitoring methods provided herein, no increase in the detected level of expression of any of the prostate-cancer related markers, e.g. FLNA, in the second sample as compared to the level of expression of the prostate-cancer related markers, e.g. FLNA, in the first sample is an indication that the therapy is efficacious for treating prostate cancer in the subject. In certain embodiments the monitoring methods provided herein, further comprise comparing the level of expression of the prostate-cancer related markers, e.g. FLNA, in the first sample or the level of expression of the prostate-cancer related markers, e.g. FLNA, in the second sample with the expression of the one or more prostate-cancer related markers in a control sample.

In certain embodiments of the monitoring methods provided herein, an increase in the level of expression of the prostate-cancer related markers, e.g. FLNA, in the second sample as compared to the level of expression of the prostate-cancer related markers, e.g. FLNA, in the first sample is an indication for selection of active treatment of prostate cancer in the subject. In certain embodiments of the monitoring methods provided herein, no increase in the detected level of expression of any of the prostate-cancer related markers, e.g. FLNA, in the second sample as compared to the level of expression of the prostate-cancer related markers, e.g. FLNA, in the first sample is an indication against selection of active treatment of prostate cancer in the subject, e.g., adopting watchful waiting. In certain embodiments of the monitoring methods provided herein, wherein an increased expression level of FLNA in the second sample as compared to the expression level in the first sample is an indication that the therapy is not efficacious in the treatment of prostate cancer.

In certain embodiments of the monitoring methods provided herein, modulation of the level of expression of FLNA in the second sample as compared to the level of expression of FLNA in the first sample is indicative of a change in prostate cancer status in response to treatment of the prostate cancer in the subject. In certain embodiments of the monitoring methods provided herein, the methods further comprise comparing the level of expression of FLNA in the first sample; or the level of expression of FLNA in the second sample to the level of expression of one or more prostate-cancer related markers in a normal control sample.

In certain embodiments the diagnostic methods provided herein further comprise detecting the level of expression of prostate specific antigen (PSA), keratin 19, and/or filamin B in the biological sample and preferably further comprise comparing the level of expression of PSA, keratin 19, and/or filamin B in the biological sample to a PSA, keratin 19, and/or filamin B expression level in a normal control sample. In certain embodiments, the combination of PSA, keratin 19, and/or filamin B level with one or more of the prostate-cancer maker levels increases the predictive value of the method. In certain embodiments, the combination of PSA, keratin 19, and FLNA levels increases the predictive value of the method. In certain embodiments, the combination of FLNA and KRT19 levels increases the predictive value of the method. In a particular embodiment, the combination of FLNA and KRT19 levels and age increases the predictive value of the method. In certain embodiments, the combination of PSA, FLNA, and FLNB levels increases the predictive value of the method. In certain embodiments, the combination of FLNA and FLNB levels increases the predictive value of the method.

In particular embodiments, the invention provides methods for diagnosing or predicting prostate cancer in a subject by contacting a biological sample from a subject with a detection reagent specific for prostate cancer markers FLNA, FLNB, and PSA; (2) measuring the amount of FLNA, FLNB, and PSA in the biological sample by the detection reagent; and (3) comparing the level of expression of FLNA, FLNB, and PSA in the biological sample obtained from the subject with a level of expression of the prostate-cancer related protein in a normal control sample, thereby diagnosing or predicting prostate cancer in the subject. In one embodiment of this method, age is also used as a prostate-cancer marker. In one embodiment, prostate cancer markers FLNA, FLNB, age and PSA together predict prostate cancer more accurately than PSA alone between patients with or without prostate cancer. In another embodiment, the method provides a predictive score, or AUC, of about 0.59, 0.64, or 0.69 (see FIG. 10).

In particular embodiments, the invention provides methods for diagnosing or predicting prostate cancer versus benign prostatic hyperplasia (BPH) in a subject by contacting a biological sample from a subject with a detection reagent specific for prostate cancer markers FLNA, KRT19, and PSA; (2) measuring the amount of FLNA, KRT19, and PSA in the biological sample by the detection reagent; and (3) comparing the level of expression of FLNA, KRT19, and PSA in the biological sample obtained from the subject with a level of expression of the prostate-cancer related protein in a normal control sample, thereby diagnosing or predicting prostate cancer versus BPH in the subject, i.e., distinguishing between prostate cancer and BPH in the subject. In one embodiment of this method, age is also used as a prostate-cancer marker to distinguish prostate cancer from BPH. In one embodiment, prostate cancer markers FLNA, KRT19, PSA and age together discriminate between prostate cancer and BPH over use of PSA alone. In one embodiment, the method provides a predictive score, or AUC, of about 0.59, 0.69, or 0.70 (see FIG. 11).

In certain embodiments the monitoring methods provided herein further comprise detecting the level of expression of prostate specific antigen (PSA), keratin 19, and/or filamin B in the first sample and the second sample, and preferably further comprising comparing the level of expression of PSA, keratin 19, and/or filamin B in the first sample with the level of expression of PSA, keratin 19, and/or filamin B in the second sample. In certain monitoring methods, the change in PSA, keratin 19, and/or filamin B level in combination with the change in prostate-cancer maker level increases the predictive value of the method.

In certain embodiments the diagnostic and monitoring methods provided herein further comprise comparing the detected level of the one or more prostate markers in the biological samples with one or more control samples wherein the control sample is one or more of a sample from the same subject at an earlier time point than the biological sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and sample obtained from a subject with non-aggressive prostate cancer. Comparison of the marker levels in the biological samples with control samples from subjects with various normal and abnormal prostate states facilitates the differentiation between various prostate states including normal prostate and prostate cancer, benign prostate hyperplasia and prostate cancer, benign prostate hyperplasia and normal prostate, androgen dependent and androgen independent prostate cancer, aggressive prostate cancer and non-aggressive prostate cancer, aggressive prostate cancer and non-aggressive prostate cancer, or between any two or more prostate states including normal prostate, prostate cancer, benign prostate hyperplasia, androgen dependent prostate cancer, androgen independent prostate cancer, aggressive prostate cancer, non-aggressive prostate cancer, metastatic prostate cancer, and non-metastatic prostate cancer. Further, the prostate cancer may be a prostatic intraepithelial neoplasia, adenocarcinoma, small cell carcinoma, or squamous cell carcinoma.

In certain embodiments the diagnostic and monitoring methods provided herein further comprising detecting the size of the prostate tumor in the subject. In certain embodiments the monitoring methods provided herein further comprise detecting a change in the size or relative aggressiveness of the tumor. In certain embodiments, the size of the prostate tumor in the subject is detected prior to administering the at least a portion of a treatment regimen to the subject. In certain embodiments, the size of the prostate tumor in the subject is detected after administering the at least a portion of a treatment regimen to the subject. Certain monitoring methods, further comprise comparing the size of the prostate tumor in the subject prior to administering the at least a portion of a treatment regimen to the subject to the size of the prostate tumor in the subject after administering the at least a portion of a treatment regimen to the subject.

In certain embodiments the diagnostic and monitoring methods provided herein further comprising obtaining a subject sample.

In certain embodiments the diagnostic and monitoring methods provided herein further comprising selecting a treatment regimen for the subject based on the level expression of one or more of the prostate-cancer related markers provided herein. A treatment regimen can include active treatment, for example, chemotherapy, radiation therapy, e.g., radiation of the prostate, surgery, e.g., surgical prostate resection, hormone therapy, or any other therapeutic approach useful for treating an oncologic disorder in a subject, or watchful waiting.

In certain embodiments the diagnostic and monitoring methods provided herein further comprising selecting a subject for having or being suspected of having prostate cancer.

In certain embodiments the diagnostic and monitoring methods provided herein further comprising treating the subject with a regimen including one or more treatments selected from the group consisting of surgery (e.g., surgical prostate resection), radiation (e.g., radiation of the prostate), hormone therapy, antibody therapy, therapy with growth factors, cytokines, and chemotherapy.

In certain embodiments the diagnostic and monitoring methods provided herein further comprising selecting the one or more specific treatment regimens for the subject based on the results of the diagnostic and monitoring methods provided herein. In certain embodiments, the treatment method is maintained based on the results from the diagnostic or prognostic methods. n certain embodiments, the treatment method is changed based on the results from the diagnostic or prognostic methods.

In certain embodiments, a change the treatment regimen comprises changing a hormone based therapy treatment. In certain embodiments, treatments for prostate cancer include one or more of surgery, e.g., surgical prostate resection, radiation, e.g., radiation of the prostate, hormone therapy, antibody therapy, therapy with growth factors, cytokines, or chemotherapy for an interval prior to performing a subsequent diagnostic, prognostic, or monitoring method provided herein.

In certain embodiments of the diagnostic and monitoring methods provided herein, the method of detecting a level comprises isolating a component of the biological sample.

In certain embodiments of the diagnostic and monitoring methods provided herein, the method of detecting a level comprises labeling a component of the biological sample.

In certain embodiments of the diagnostic and monitoring methods provided herein, the method of detecting a level comprises amplifying a component of a biological sample.

In certain embodiments of the diagnostic and monitoring methods provided herein, the method of detecting a level comprises forming a complex with a probe and a component of a biological sample. In certain embodiments, forming a complex with a probe comprises forming a complex with at least one non-naturally occurring reagent. In certain embodiments of the diagnostic and monitoring methods provided herein, the method of detecting a level comprises processing the biological sample. In certain embodiments of the diagnostic and monitoring methods provided herein, the method of detecting a level of at least two markers comprises a panel of markers. In certain embodiments of the diagnostic and monitoring methods provided herein, the method of detecting a level comprises attaching the marker to be detected to a solid surface.

The invention provides methods of selecting for administration of active treatment or against administration of active treatment of prostate cancer in a subject comprising: (1) detecting a level of a marker, e.g. FLNA, in a first sample obtained from the subject having prostate cancer wherein the subject has not been actively treated for prostate cancer; (2) detecting a level of a marker, e.g. FLNA, in a second sample from the subject; (3) comparing the level of the marker in the first sample with the level of the marker in the second sample; wherein selecting for administration of active treatment or against administration of active treatment of prostate cancer is based on the presence or absence of changes in the level of expression of the marker between the first sample and the second sample.

In certain embodiments, the method further comprising obtaining a third sample obtained from the subject, detecting a level of a marker, e.g. FLNA, in the third sample, and comparing the level of the marker in the third sample with the level of the marker in the first sample or the marker in the second sample.

In certain embodiments, an increased level of FLNA in the second sample as compared to the level of FLNA in the first sample is an indication that the therapy is not efficacious in the treatment of prostate cancer.

In certain embodiments, an increase of FLNA in the second sample as compared to the level of FLNA in the first sample is an indication for selecting active treatment for prostate cancer.

In certain embodiments, the method further comprises comparing the level of the marker, e.g. FLNA, in the first sample or the level of the marker, e.g. FLNA, in a control sample. In certain embodiments, the method comprises detecting the level of the marker, e.g. FLNA, in the second sample; and comparing the level of the marker, e.g. FLNA, in the second sample with the marker, e.g. FLNA, in the first sample. In certain embodiments, the method further comprises comparing the level of the marker, e.g. FLNA, in the first sample; or the level of expression of the marker, e.g. FLNA, in the second sample to the level of the marker, e.g. FLNA, in a control sample.

In certain embodiments, no change in the level of expression of the marker, e.g. FLNA, between the first sample and the second sample is an indication for selecting against active treatment for prostate cancer.

In certain embodiments, the methods further comprise detecting the level of prostate specific antigen (PSA), keratin 19, and/or filamin B in the first sample and the second sample, and then preferably further comprising comparing the level of PSA, keratin 19, and/or filamin B in the first sample with the level of PSA, keratin 19, and/or filamin B in the second sample. In one embodiment, FLNA and keratin 19 are detected and compared. In one embodiment, FLNA, keratin 19 and PSA are detected and compared. In one embodiment, FLNA, keratin 19 and age are detected or determined and compared. In one embodiment, FLNA and FLNB are detected and compared. In one embodiment, FLNA, FLNB and PSA are detected and compared.

In certain embodiments, a decrease in the level of FLNA in the second sample as compared to the level of FLNA in the first sample in combination with a decrease in the level of PSA, keratin 19, and/or filamin B in the second sample as compared to the level of PSA, keratin 19, and/or filamin B in the first sample has greater predictive value that the therapy is efficacious in treating prostate cancer in the subject than analysis of a single marker alone.

In certain embodiments, a decrease in the level of FLNA in the second sample as compared to the level of FLNA in the first sample in combination with a decrease in the level of expression of PSA, keratin 19, and/or filamin B in the second sample as compared to the level of PSA, keratin 19, and/or filamin B in the first sample has greater predictive value that for selecting against active treatment for prostate cancer than analysis of a single marker alone.

1. Diagnostic Assays

An exemplary method for detecting the presence or absence or change of expression level of a marker protein or nucleic acid in a biological sample involves obtaining a biological sample (e.g. an oncological disorder-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. In a preferred embodiment, the binding agent is an FLNA binding protein, e.g., antibody, or antigen binding fragment thereof, as described herein.

Methods provided herein for detecting the presence, absence, change of expression level of a marker protein or nucleic acid in a biological sample include obtaining a biological sample from a subject that may or may not contain the marker protein to be detected, contacting the sample with a marker-specific binding agent (i.e., a FLNA binding protein, e.g., antibody, or antigen binding fragment thereof, as described herein) that is capable of forming a complex with the marker protein, and contacting the sample with a detection reagent for detection of the marker-marker-specific binding agent complex, if formed. It is understood that the methods provided herein for detecting an expression level of a marker in a biological sample includes the steps to perform the assay. In certain embodiments of the detection methods, the level of the marker protein or nucleic acid in the sample is none or below the threshold for detection.

The methods include formation of either a transient or stable complex between the marker and the marker-specific binding agent (e.g., a FLNA antibody, or antigen binding fragment thereof as described herein). The methods require that the complex, if formed, be formed for sufficient time to allow a detection reagent to bind the complex and produce a detectable signal (e.g., fluorescent signal, a signal from a product of an enzymatic reaction, e.g., a peroxidase reaction, a phosphatase reaction, a beta-galactosidase reaction, or a polymerase reaction).

In certain embodiments, all markers are detected using the same method. In certain embodiments, all markers are detected using the same biological sample (e.g., same body fluid or tissue). In certain embodiments, different markers are detected using various methods. In certain embodiments, markers are detected in different biological samples.

In certain embodiments of the invention, the marker to be detected is a protein, in particular FLNA. Proteins are detected using a number of assays in which a complex between the marker protein to be detected and the marker specific binding agent would not occur naturally, for example, because one of the components is not a naturally occurring compound or the marker for detection and the marker specific binding agent are not from the same organism (e.g., human marker proteins detected using marker-specific binding antibodies from mouse, rat, or goat). In a preferred embodiment of the invention, the marker protein for detection is a human marker protein. In certain detection assays, the human markers for detection are bound by marker-specific, non-human antibodies, thus, the complex would not be formed in nature. The complex of the marker protein can be detected directly, e.g., by use of a labeled marker-specific antibody that binds directly to the marker, or by binding a further component to the marker-specific antibody complex. In certain embodiments, the further component is a second marker-specific antibody capable of binding the marker at the same time as the first marker-specific antibody. In certain embodiments, the further component is a secondary antibody that binds to a marker-specific antibody, wherein the secondary antibody preferably linked to a detectable label (e.g., fluorescent label, enzymatic label, biotin). When the secondary antibody is linked to an enzymatic detectable label (e.g., a peroxidase, a phosphatase, a beta-galactosidase), the secondary antibody is detected by contacting the enzymatic detectable label with an appropriate substrate to produce a colorimetric, fluorescent, or other detectable, preferably quantitatively detectable, product. Antibodies for use in the methods of the invention can be polyclonal, however, in a preferred embodiment monoclonal antibodies are used. An intact antibody, or a fragment or derivative thereof (e.g., Fab or F(ab')$_2$) can be used in the methods of the invention. Such strategies of marker protein detection are used, for example, in ELISA, RIA, immunoprecipitation and western blot, Immunoprecipitation-Multiple Reaction Monitoring (IP-MRM) or LC-MS/MS, and immunofluorescence assay methods.

In certain embodiments, the marker-specific binding agent complex is attached to a solid support for detection of the marker. The complex can be formed on the substrate or formed prior to capture on the substrate. For example, in an ELISA, RIA, immunoprecipitation assay, western blot, immunofluorescence assay, in gel enzymatic assay the marker for detection is attached to a solid support, either directly or indirectly. In an ELISA, RIA, or immunofluorescence assay, the marker is typically attached indirectly to a solid support through an antibody or binding protein. In a western blot or immunofluorescence assay, the marker is typically attached directly to the solid support. For in-gel enzyme assays, the marker is resolved in a gel, typically an acrylamide gel, in which a substrate for the enzyme is integrated.

In another aspect, this application provides methods for detecting the presence, absence, change of expression level of FLNA using an immunoaffinity enrichment approach coupled with MRM (i.e., IPMRM). IPMRM combines immunoprecipitation (IP) with mass spectrometry and allows for the rapid quantitation of proteins with enhanced sensitivity and specificity. For biomarkers, this technique has been shown to achieve low mg/mL quantitation by selective enrichment of target proteins in complex matrices (see Nicol G R, et al. (2008) Molecular & Cellular Proteomics 7 (10):1974-1982; Kulasingam V, et al. (2008) Journal of Proteome Research 7 (2):640-647; Berna M, Ackermann B (2009) Anal Chem 81 (10):3950-3956, the contents of which are incorporated herein by reference). For example, ELISA alone may not detect all forms of FLNA in a sample. However, IPMRM allows detection of different peptides along the length of the entire protein and thus has increased specificity. In one embodiment, IPMRM is used for the detection of FLNA in a serum sample. In one embodiment, IPMRM is used for the detection of FLNA in a plasma sample.

In one embodiment, IPMRM involves enrichment of one or more markers, e.g., FLNA, using one or more capture antibodies (e.g., one or more of the binding proteins of the invention), followed by digestion and analysis of surrogate peptides by stable isotope dilution MRM. For example, one or more of the 2C12, 3F4, and/or 6E3 antibodies may be used as the capture antibodies in the methods of the invention. In one embodiment, the 2C12 and 3F4 antibodies are used as the capture antibodies in the assay. In another embodiment, surrogate peptides can be tryptic peptides between, for example, 8 and 22 amino acids. In one embodiment, surrogate peptides used in FLNA IPMRM can comprise one or more of peptides P2 (AGVAPLQVK) (SEQ ID NO:40) and P4 (YNEQHVPGSPFTAR) (SEQ ID NO:41). In one embodiment, peptide P2 is used in the IPMRM.

In particular, for IPMRM, capture antibodies (e.g., one or more of the 2C12, 3F4, and/or 6E3 antibodies described herein), are immobilized onto a support using methods known in the art, e.g., onto an agarose support using, for example, the ThermoFisher Scientific Pierce Direct IP Kit (ThermoFisher Scientific), and coupled to coupling resin Immunoprecipitation can then be performed using methods known in the art. For example, the Pierce Direct IP Kit can be used. In one embodiment, the resin-coupled antibodies can be washed and human serum added along with prepared lysis buffer solution and EDTA, and incubated. The resin can then be washed again with IP lysis/wash buffer and conditioning buffer. The captured proteins can then be eluted and incubated. The IP eluates from the surrogate matrix can be used to prepare peptide (e.g., P2 and/or P4) calibration curves by spiking with a synthetic peptide stock solution. Samples can then by subjected to trypsin digestion using methods known in the art (e.g., using the Flash Digest Kit (Perfinity Biosciences, West Lafayette, IN).

MRM analysis can be performed on a mass spectrometer, e.g., a 6500 QTRAP mass spectrometer (Sciex) equipped with an electrospray source, a 1290 Infinity UPLC system (Agilent Technologies, Santa Clara, CA) and a XBridge Peptide BEH300 C18 (3.5 gm, 2.1 mm×150 mm) column (Waters, Milford, MA). Liquid chromatography can then be carried out. For example, liquid chromatography can be carried out at a flow rate of 400 µL/min, with a sample injection volume of 30 µL at a temperature of 60° C. In one embodiment, mobile phase A can consist of 0.1% formic acid (Sigma Aldrich) in water (ThermoFisher Scientific) and mobile phase B can consist of 0.1% formic acid in acetonitrile (ThermoFisher Scientific). The gradient with respect to % B can be as follows: 0-1.5 min, 5%; 1.5-2 min, 5-15%; 2-5 min, 15%; 5-7.1 min, 15-20%; 7.1-8.1 min, 20-80%; 8.1-9.0 min, 80%; and 9.0-9.1 min, 80-5%. 9.1-16 min, 5%.

In one embodiment, the instrument parameters for the mass spectrometer, e.g., a 6500 QTRAP mass spectrometer, can be as follows: Ion spray voltage of 5500 V, curtain gas of 20 psi, collision gas set to "medium", interface heater temperature of 400° C., nebulizer gas (GS1) of 80 psi and ion source gas (GS2) of 80 psi and unit resolution for both Q1 and Q3 quadrupoles.

Potential surrogate peptides for FLNA quantitation can be chosen by methods known in the art, e.g., using Skyline software and LC-MS/MS analysis (LTQ Orbitrap Velos coupled to Eksigent nano-LC) of recombinant FLNA protein (GenScript) tryptic digest. Surrogate peptides can be chosen based on surrogate peptide selection rules (Halquist, et al., *Biomed Chromatography* 25 (1-2):47-58) and signal intensities of the peptides in spiked and unspiked serum digests. The uniqueness of the surrogate peptides to the target protein can confirmed by running BLAST searches. In one embodiment, heavy labeled versions of surrogate peptide 2 (P2) and peptide 4 (P4), AGVAPLQV[K(13C6; 15N2)] (SEQ ID NO:40) and YNEQHVPGSPFTA[R(13C6; 15N4)] (SEQ ID NO:41), which were selected using the methods described above, can be used as internal standards.

MRM transitions can be optimized using synthetic surrogate peptides (GenScript) and their internal standards (ThermoFisher Scientific) and the following m/z transitions can be monitored: 441.7 $(M+2H)^{2+} \rightarrow 584.5$ $(y_5^{1+})$ for P2; 535 $(M+3H)^{3+} \rightarrow 832.4$ $(y_8^{1+})$ for P4, 445.5 $(M+2H)^{2+} \rightarrow 592.1$ $(y_5^{1+})$ for P2 internal standard (P2_IS), and 538.4 $(M+3H)^{3+} \rightarrow 842.5$ $(y_8^{1+})$ for P4 internal standard P4_IS.

Analysis and quantitation of IPMRM data can be performed using methods known in the art, for example, the Analyst® software (version 1.6.2, AB Sciex, Framingham, MA). In one embodiment, peak integrations can be reviewed manually. The calibration curve for FLNA P2 and P4 peptides can be constructed by plotting the peak area ratios (analyte/internal standard) versus concentration of the standard with $1/x^2$ linear least square regression.

In yet another aspect, this application provides a method for detecting the presence of FLNA in vivo (e.g., in vivo imaging in a subject). The subject method can be used to diagnose a disorder, e.g., prostate cancer. In exemplary embodiments, the method includes: (i) administering the anti-FLNA antibody or fragment thereof as described herein to a subject or a control subject under conditions that allow binding of the antibody or fragment to FLNA; and (ii) detecting formation of a complex between the antibody or fragment and FLNA, wherein a statistically significant change in the formation of the complex in the subject relative to the control subject is indicative of the presence of FLNA.

2. Detection of Expression Levels

Marker levels can be detected based on the absolute expression level or a normalized or relative expression level. Detection of absolute marker levels may be preferable when monitoring the treatment of a subject or in determining if there is a change in the prostate cancer status of a subject. For example, the expression level of one or more markers can be monitored in a subject undergoing treatment for prostate cancer, e.g., at regular intervals, such a monthly intervals. A modulation in the level of one or more markers can be monitored over time to observe trends in changes in marker levels. Expression levels of FLNA in the subject may be higher than the expression level of those markers in a normal sample, but may be lower than the prior expression level, thus indicating a benefit of the treatment regimen for the subject. Similarly, rates of change of marker levels can be important in a subject who is not subject to active treatment for prostate cancer (e.g., watchful waiting). Changes, or not, in marker levels may be more relevant to treatment decisions for the subject than marker levels present in the population. Rapid changes in marker levels in a subject who otherwise appears to have a normal prostate may be indicative of an abnormal prostate state, even if the markers are within normal ranges for the population.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cancer sample, or between samples from different sources.

Alternatively, the expression level can be provided as a relative expression level as compared to an appropriate control, e.g., population control, adjacent normal tissue control, earlier time point control, etc. Preferably, the samples used in the baseline determination will be from non-cancer cells. The choice of the cell source is dependent on the use of the relative expression level. Using expression found in normal tissues as a mean expression score aids in validating whether the marker assayed is cancer specific (versus normal cells). In addition, as more data is accumulated, the mean expression value can be revised, providing improved relative expression values based on accumulated data. Expression data from cancer cells provides a means for grading the severity of the cancer state.

As described in detail herein, the expression level of FLNA in a sample can be detected and/or quantified by using any one or more of the binding proteins described herein, wherein FLNA is detected and/or quantified under conditions such that the binding protein binds to FLNA in the sample.

In particular, the present invention provides methods for diagnosing an abnormal prostate state, e.g., prostate cancer, in a subject comprising detecting a level of FLNA in a biological sample from the subject; and comparing the level of FLNA in the biological sample with the level of FLNA in a normal control sample. The level of FLNA can be detected using a binding protein described herein, wherein an altered level of FLNA in the biological sample relative to the normal control sample is indicative of an abnormal prostate state, e.g., prostate cancer, in the subject.

The present invention also provides methods for identifying a subject as being at increased risk for developing prostate cancer, the method comprising detecting a level of FLNA in a biological sample from the subject; and comparing the level of FLNA in the biological sample with the level of FLNA in a normal control sample, wherein the level of FLNA is detected using a binding protein described herein. An altered level of FLNA in the biological sample relative to the normal control sample is indicative of an increased risk for developing prostate cancer in the subject.

The present invention further provides methods for monitoring prostate cancer in a subject, the method comprising detecting a level of FLNA in a first biological sample obtained at a first time from a subject having prostate cancer; detecting a level of expression of FLNA in a second biological sample obtained from the subject at a second time, wherein the second time is later than the first time; and comparing the level of FLNA in the second sample with the level of FLNA in the first sample. The level of FLNA is detected using a binding protein as described herein. A change in the level of FLNA in the second sample as compared to the first sample is indicative of a change in prostate cancer status in the subject.

In the methods of the invention, the level of FLNA can be detected using, for example, an enzyme-linked immunosorbent assay (ELISA), radioimmunoassay (RIA), antibody-labeled fluorescence imaging, tissue immunohistochemistry, or an immunoprecipitation-multiple reaction monitoring (IPMRM) assay, as described herein.

The present invention also provides methods for measuring the level of FLNA protein in a biological sample by detecting and/or quantifying the amount of one or more FLNA surrogate peptides in a protein digest prepared from the biological sample (e.g., protein digest prepared from filamin A protein isolated, purified or precipitated from the biological sample, e.g. by using a filamin A binding protein) using mass spectrometry; and calculating the level of FLNA protein in the sample. In one embodiment, the amount of FLNA is a relative amount or an absolute amount. In a particular embodiment, the protein digest comprises a protease digest, for example, a trypsin digest.

Quantifying the amount of one or more FLNA surrogate peptides may comprise comparing an amount of one or more FLNA surrogate peptides in one biological sample to the amount of the same FLNA surrogate peptides in a different and separate biological sample. Quantifying one or more FLNA surrogate peptides may comprise determining the amount of the each of the FLNA surrogate peptides in a biological sample by comparison to an added, corresponding internal standard peptide of known amount, where each of the FLNA surrogate peptides in the biological sample is compared to an internal standard peptide having the same amino acid sequence. The internal standard peptide may be an isotopically labeled peptide. The isotopically labeled internal standard peptide may contain one or more heavy stable isotopes selected from $^{18}O$, $^{17}O$, $^{34}S$, $^{15}N$, $^{13}C$, $^{2}H$ or combinations thereof.

In these embodiments, the mass spectrometry may comprise tandem mass spectrometry, ion trap mass spectrometry, triple quadrupole mass spectrometry, MALDI-TOF mass spectrometry, MALDI mass spectrometry, and/or time of flight mass spectrometry. The mode of mass spectrometry used may be, for example, Multiple Reaction Monitoring (MRM).

The present invention provides methods for detecting and/or quantifying the level of FLNA in a sample by detecting and/or quantifying one or more surrogate peptides comprising or consisting of the amino acid sequence of SEQ ID NO:40 (P2) and/or SEQ ID NO:41 (P4), in a protein digest prepared from the sample using a mass spectrometry technique, e.g., multiple reaction monitoring (MRM). In one embodiment, the protein digest is prepared from filamin A protein isolated, purified or precipitated from the biological sample, e.g. by using a filamin A binding protein such as a binding protein described herein. In one embodiment, the MRM is immunoprecipitation-multiple reaction monitoring (IPMRM) comprising a FLNA immunoprecipitation step, wherein the immunoprecipitation is carried out using one or more binding proteins as described herein. In one embodiment, the IPMRM detects more than one prostate cancer marker, e.g, the FLNA, PSA, and/or keratin 19 prostate cancer markers. In one embodiment, the IPMRM detects FLNA and keratin 19.

In these embodiments, the one or more surrogate peptides detected by mass spectrometry, e.g., MRM, have amino acid sequences consisting of SEQ ID NO:40 and/or SEQ ID NO:41. In other embodiments, the surrogate peptide detected by mass spectrometry, e.g., MRM, has an amino acid sequence comprising SEQ ID NO:40. In a preferred embodiment, the surrogate peptide detected in the mass spectrometry assay, e.g., MRM, has an amino acid sequence consisting of SEQ ID NO:40.

In one embodiment, MRM comprises identifying the one or more surrogate peptides using one or more mass transitions m/z selected from the group consisting of: 441.7 $(M+2H)^{2+} \rightarrow 584.5$ $(y_5^{1+})$ for P2; 535 $(M+3H)^{3+} \rightarrow 832.4$ $(y_8^{1+})$ for P4, 445.5 $(M+2H)^{2+} \rightarrow 592.1$ $(y_5^{1+})$ for P2 internal standard (P2_IS), and 538.4 $(M+3H)^{3+} \rightarrow 842.5$ $(y_8^{1+})$ for P4 internal standard P4_IS. In one embodiment, MRM comprises detecting and/or quantifying a surrogate peptide for FLNA having the amino acid sequence consisting of SEQ ID NO:40 (P2) using the mass transition m/z 441.7 $(M+2H)^{2+} \rightarrow 584.5$ $(y_5^{1+})$ for P2 and, optionally, further using the mass transition m/z 445.5 $(M+2H)^{2+} \rightarrow 592.1$ $(y_5^{1+})$ for P2 internal standard (P2_IS). In one embodiment, MRM comprises detecting and/or quantifying a surrogate peptide for FLNA having the amino acid sequence consisting of SEQ ID NO:41 (P4) using the mass transition 535 $(M+3H)^{3+} \rightarrow 832.4$ $(y_8^{1+})$ for P4 and, optionally, further using the mass transition 538.4 $(M+3H)^{3+} \rightarrow 842.5$ $(y_8^{1+})$ for P4 internal standard P4_IS.

Methods for diagnosing an abnormal prostate state, e.g., prostate cancer, in a subject using an MRM assay, e.g., immunoprecipitation-multiple reaction monitoring (IP-MRM), are also provided. In one embodiment, the level of FLNA in a biological sample from the subject is detected and compared with the level of FLNA in a normal control sample using MRM wherein one or more surrogate peptides comprising the amino acid sequence of SEQ ID NO:40 (P2) and/or SEQ ID NO:41 (P4) are detected, and wherein an altered level of FLNA in the biological sample relative to the normal control sample is indicative of an abnormal prostate state in the subject. An increased level of FLNA in the biological sample relative to the normal control sample is indicative of an abnormal prostate state, e.g., prostate cancer, in the subject, whereas no increase in the detected level of FLNA in the biological sample relative to the normal control sample is indicative of a normal prostate state in the subject.

The level of one or more of PSA, keratin 19 and/or filamin B in the biological sample can also be detected using any of the methods described herein, and compared to the level of the corresponding markers in a normal control sample.

The present invention also provides methods for identifying a subject as being at increased risk for developing prostate cancer comprising detecting a level of FLNA in a biological sample from the subject and comparing the level of FLNA in the biological sample with the level of FLNA in a normal control sample, wherein the level of FLNA is detected using an MRM assay, e.g., IPMRM, wherein one or more surrogate peptides comprising the amino acid sequence SEQ ID NO:40 (P2) and/or SEQ ID NO:41 (P4) are detected, and wherein an altered level of FLNA in the biological sample relative to the normal control sample is indicative of an increased risk for developing prostate cancer in the subject.

The level of one or more of PSA, keratin 19 and/or filamin B in the biological sample can also be detected using any of the methods described herein, and compared to the level of the corresponding markers in a normal control sample.

The present invention also provides methods for monitoring prostate cancer in a subject comprising detecting a level of FLNA in a first biological sample obtained at a first time from a subject having prostate cancer, detecting a level of expression of FLNA in a second biological sample obtained from the subject at a second time, wherein the second time is later than the first time, and comparing the level of FLNA in the second sample with the level of FLNA in the first sample. In one embodiment, the level of FLNA is detected using an MRM assay, e.g., IPMRM, wherein one or more surrogate peptides comprising the amino acid sequence of SEQ ID NO:40 (P2) and/or SEQ ID NO:41 (P4) are detected, and wherein a change in the level of FLNA in the second sample as compared to the first sample is indicative of a change in prostate cancer status in the subject. In one embodiment, the subject is actively treated for prostate cancer prior to obtaining the second sample. In another embodiment, the subject is not actively treated for prostate cancer prior to obtaining the second sample. In one embodiment, an increased level of FLNA in the second biological sample as compared to the first biological sample is indicative of progression of the prostate cancer in the subject. In another embodiment, no increase in the detected level of expression of FLNA in the second biological sample as compared to the first biological sample is indicative of non-progression of the prostate cancer in the subject.

In any of the foregoing embodiments, the immunoprecipitation step of the IPMRM can be carried out using any one or more of the binding proteins described herein. For example, the 2C12, 3F4, and/or the 6E3 antibodies may be used in the IPMRM methods of the invention. In one embodiment, the 2C12 and 3F4 antibodies are used in IPMRM. In one embodiment, the 2C12 antibody is used in IPMRM. In one embodiment, the 3F4 antibody is used in IPMRM. Also in any of the foregoing embodiments, the surrogate peptide detected in the assay can be P2 (SEQ ID NO:40).

D. Predictive Medicine

The present invention pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing a disease or disorder, such as, without limitation, an oncological disorder, e.g., prostate cancer. Such assays can be used for prognostic or predictive purposes to thereby prophylactically treat an individual prior to the onset of the disorder.

Yet another aspect of the invention pertains to monitoring the influence of agents (e.g., drugs or other compounds administered either to inhibit an oncological disorder, e.g., prostate cancer, or to treat or prevent any other disorder, i.e. in order to understand any carcinogenic effects that such treatment may have) on the expression or activity of a marker of the invention in clinical trials.

E. Monitoring Clinical Trials

Monitoring the influence of agents (e.g., drug compounds) on the level of expression of a marker of the invention can be applied not only in basic drug screening or monitoring the treatment of a single subject, but also in clinical trials. For example, the effectiveness of an agent to affect marker expression can be monitored in clinical trials of subjects receiving treatment for an oncological disorder. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention (e.g., FLNA, optionally in combination with PSA) in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased expression of the marker gene(s), e.g. FLNA, during the course of treatment may indicate ineffective dosage and the desirability of increasing the dosage. Conversely, decreased expression of the marker gene(s), e.g. FLNA, may indicate efficacious treatment and no need to change dosage.

F. Kits

The invention also provides compositions and kits for diagnosing, prognosing, or monitoring a disease or disorder, recurrence of a disorder, or survival of a subject being treated for a disorder (e.g., an abnormal prostate state, BPH, an oncologic disorder, e.g., prostate cancer). These kits include one or more of the following: a detectable antibody that specifically binds to a marker of the invention, reagents for obtaining and/or preparing subject tissue samples for staining, and instructions for use. In one embodiment, the antibody is any one or more of the binding proteins described herein, including the 2C12, 3F4, and/or 6E3 antibodies of the invention.

The invention also encompasses kits for detecting the presence of a marker protein or nucleic acid in a biological sample. Such kits can be used to determine if a subject is suffering from or is at increased risk of developing an abnormal prostate state. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for use of the kit for practicing any of the methods provided herein or interpreting the results obtained using the kit based on the teachings provided herein. The kits can also include reagents for detection of a control protein in the sample not related to the abnormal prostate state, e.g., actin for tissue samples, albumin in blood or blood derived samples for normalization of the amount of the marker present in the sample. The kit can also include the purified marker for detection for use as a control or for quantitation of the assay performed with the kit.

Kits include reagents for use in a method to diagnose prostate cancer in a subject (or to identify a subject predisposed to developing prostate cancer, etc.), the kit comprising a detection reagent, e.g. an antibody of the invention, wherein the detection reagent is specific for a prostate cancer-specific protein, e.g. FLNA. In one embodiment, the detection reagent is any one or more of the binding proteins described herein, including the 2C12, 3F4, and/or 6E3 antibodies of the invention. In one embodiment, the detection reagent comprises the 2C12 and/or 3F4 antibodies. In one embodiment, the detection reagent comprises the 2C12 antibody. In one embodiment, the detection reagent comprises the 3F4 antibody.

For antibody-based kits, the kit can comprise, for example: (1) a first antibody (e.g., attached to a solid support) which binds to a first marker protein; and, optionally, (2) a second, different antibody which binds to either the first marker protein or the first antibody and is conjugated to a detectable label. In certain embodiments, the kit includes (1) a second antibody (e.g., attached to a solid support) which binds to a second marker protein; and, optionally, (2) a second, different antibody which binds to either the second marker protein or the second antibody and is conjugated to a detectable label. The first and second marker proteins are different. In an embodiment, the first marker is FLNA. In another embodiment, either the first or the second marker is PSA. In other certain embodiments, neither the first marker nor the second marker is PSA. In certain embodiments, the kit comprises a third antibody which binds to a third marker protein which is different from the first and second marker proteins, and a second different antibody that binds to either the third marker protein or the antibody that binds the third marker protein wherein the third marker protein is different from the first and second marker proteins. Additional marker proteins can include, for example, keratin 19 and/or filamin B (FLNB).

Reagents specific for detection of a marker of the invention, e.g., FLNA, PSA, keratin 19 and/or FLNB, allow for detection and quantitation of the marker in a complex mixture, e.g., serum, tissue sample. In certain embodiments, the reagents are species specific. In certain embodiments, the reagents are not species specific. In certain embodiments, the reagents are isoform specific. In certain embodiments, the reagents are not isoform specific. In certain embodiments, the reagents detect total FLNA, PSA, keratin 19 and/or FLNB.

In certain embodiments, the kit includes reagents for use in an immunoprecipation assay for the detection of one or more markers, e.g., FLNA, PSA, keratin 19 and/or FLNB, wherein the immunoprecipitation assay is followed by a multiple reaction monitoring (MRM) assay. In one embodiment, labeled surrogate peptides for FLNA, e.g. P2 and/or P4, are included in the kit for use as internal standards.

In certain embodiments, the kits for the diagnosis, monitoring, or characterization of prostate cancer comprise at least one reagent specific for the detection of the level of expression of at least one marker, e.g., FLNA. In certain embodiments, the kits further comprise instructions for the diagnosis, monitoring, or characterization of prostate cancer based on the level of expression of the at least one marker, e.g. FLNA. In certain embodiments, the kits further comprise instructions to detect the level of PSA, keratin 19 and/or FLNB in a sample in which the at least one marker, e.g. FLNA. In certain embodiments, the kits further comprise at least one reagent for the specific detection of PSA, keratin 19 and/or FLNB. In certain embodiments, the kits further comprise at least one reagent for the specific detection of keratin 19. In certain embodiments, the kits further comprise at least one reagent for the specific detection of PSA. In certain embodiments, the kits further comprise at least one reagent for the specific detection of FLNB. In certain embodiments, the kits further comprise at least one reagent for the specific detection of FLNB and one reagent specific for the detection of PSA. In certain embodiments, the kits further comprise at least one reagent for the specific detection of keratin 19 and one reagent specific for the detection of PSA.

The invention provides kits comprising at least one reagent specific for the detection of a level of expression of at least one marker, e.g. FLNA, and at least one reagent specific for the detection of a level of expression of PSA, keratin 19 and/or FLNB. In one embodiment, the kits comprise at least one reagent specific for the detection of a level of expression of FLNA and at least one reagent specific for the detection of keratin 19. In one embodiment, the kits comprise at least one reagent specific for the detection of a level of expression of FLNA and at least one reagent specific for the detection of PSA. In one embodiment, the kits comprise at least one reagent specific for the detection of a level of expression of FLNA and at least one reagent specific for the detection of FLNB. In one embodiment, the kits comprise at least one reagent specific for the detection of a level of expression of FLNA and at least one reagent specific for the detection of keratin 19 and at least one reagent specific for the detection of PSA. In one embodiment, the kits comprise at least one reagent specific for the detection of a level of expression of FLNA and at least one reagent specific for the detection of FLNB and at least one reagent specific for the detection of PSA.

In certain embodiments, the kits can also comprise any one of, but not limited to, a buffering agent(s), a preservative, a protein stabilizing agent, reaction buffers. The kit can further comprise components necessary for detecting the detectable label (e.g., an enzyme or a substrate). The kit can also contain a control sample or a series of control samples which can be assayed and compared to the test sample. The controls can be control serum samples or control samples of purified proteins or nucleic acids, as appropriate, with known levels of target markers. Each component of the kit can be enclosed within an individual container and all of the various containers can be within a single package, along with instructions for interpreting the results of the assays performed using the kit.

The kits of the invention may optionally comprise additional components useful for performing the methods of the invention.

G. Panels

The invention provides panels of reagents for detection of a prostate-related marker, e.g. FLNA, in a subject sample and at least one control reagent. The invention also provides panels of reagents for detection of one or more prostate-related marker, e.g. FLNA and another marker, such as, for example, PSA, keratin 19 and/or FLNB, in a subject sample and at least one control reagent. In certain embodiments, the control reagent is to detect the marker for detection in the biological sample wherein the panel is provided with a control sample containing the marker for use as a positive control and optionally to quantitate the amount of marker present in the biological sample. In certain embodiments, the panel includes a detection reagent for a maker not related to an abnormal prostate state that is known to be present or absent in the biological sample to provide a positive or negative control, respectively. The panel can be provided with reagents for detection of a control protein in the sample not related to the abnormal prostate state, e.g., actin for tissue samples, albumin in blood or blood derived samples for normalization of the amount of the marker present in the sample. The panel can be provided with a purified marker for detection for use as a control or for quantitation of the assay performed with the panel.

In a preferred embodiment, the panel includes reagents for detection of markers of the invention, e.g. FLNA, preferably in conjunction with a control reagent or a detection reagent. In one embodiment, the detection reagent is any one or more of the binding proteins described herein, including the 2C12, 3F4, and/or 6E3 antibodies of the invention. In one embodiment, the detection reagent comprises the 2C12 and/or 3F4 antibodies.

In the panel, each marker is detected by a reagent specific for that marker. In certain embodiments, the panel further includes a reagent for the detection of PSA, keratin 19 and/or FLNB. In certain embodiments, the panel includes replicate wells, spots, or portions to allow for analysis of various dilutions (e.g., serial dilutions) of biological samples and control samples. In a preferred embodiment, the panel allows for quantitative detection of one or more markers of the invention.

In certain embodiments, the panel is a protein chip for detection of one or more markers. In certain embodiments, the panel is an ELISA plate for detection of one or more markers. In other embodiments, the panel provides reagents for use in an immunoprecipitation assay for the detection of one or more markers, e.g., FLNA, and optionally further providing reagents for the detection of one or more of PSA, keratin 19 and/or FLNB, wherein the immunoprecipitation assay is followed by a multiple reaction monitoring (MRM) assay. In one embodiment, labeled surrogate peptides for FLNA, e.g. P2 and/or P4, are included for use as internal standards.

In certain embodiments, the panel is a plate for quantitative PCR for detection of one or more markers.

In certain embodiments, the panel of detection reagents is provided on a single device including a detection reagent for one or more markers of the invention and at least one control sample. In certain embodiments, the panel of detection reagents is provided on a single device including a detection reagent for two or more markers of the invention and at least one control sample. In certain embodiments, multiple panels for the detection of different markers of the invention are provided with at least one uniform control sample to facilitate comparison of results between panels.

III. Pharmaceutical Compositions

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, detecting, monitoring or prognosing a disorder, and/or in research. In a specific embodiment, a pharmaceutical composition comprises one or more antibodies of the invention. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering an antibody of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes).

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

As will be appreciated by the skilled artisan, the route and/or mode of administration will vary depending upon the desired results.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1: Human FLNA Antibody Development

Animal Immunization and Fusion and Cloning

The partial FLNA protein (SEQ ID NO: 35) was used as the immunization target antigen. Lymphocytes from immunized animal with desired serum titer were fused with myeloma fusion partner derived from the P3X63Ag8.653 myeloma cell line for immortal hybridoma cell clones. Hybridoma clones 2C12, 3F4 and 6E3 were identified. These clones were propagated in DMEM (4.5 gm/L glucose, w/L-Glut, Sodium Pyruvate)+10% FBS+50 ug/ml Gentamicin. The medium is formulated for use with a 5% CO2 in air atmosphere. Cultures are incubated at 37° C. The hybridoma cells are semi-adherent, however the cells can be resuspended by pipetting alone. The 2C12, 3F4 and 6E3 clones were screened as follows for FLNA specificity.

*E. coli*-expressed partial FLNA and HEK293-expressed full length FLNA (UniProt: P21333) were screened for positive FLNA specificity. The HEK293-expressed full length FLNA sequence is shown as SEQ ID NO: 36.

Filamin B (FLNB) and Filamin C (FLNC) are the other two members from the Filamin family; they share 69% and 70% identity to FLNA, respectively. The clones were screened for negative with *E. coli*-expressed partial FLNB (aa 1416-2089) (UniProt: O75369) and *E. coli*-expressed FLNC (aa 1438-2128) (UniProt: Q14315) which cover the same region as FLNA (aa1443-2131), and HEK293-expressed full length FLNB. 10% human serum was further tested for any unexpected cross-reactivity. The sequences for these proteins are shown as SEQ ID NO: 37, SEQ ID NO: 38 and SEQ ID NO: 39, respectively.

Next, supernatants from clone 2C12, 3F4, and 6E3 were tested to bind the above proteins by ELISA. ELISA test results on 2C12, 3F4, and 6E3 specificity are shown in Table 2. FLNA proteins were tested for specificity, while homologous proteins FLNB and FLNC from the same family were tested for cross-reactivity. 10% pooled normal human serum was also included for any unexpected non-specific binding. The data in Table 2 indicates that the supernatants from the clones are highly reactive to partial or full length FLNA with limited reactivity to homologous proteins FLNB and FLNC or human serum.

TABLE 2

ELISA test results on 2C12, 3F4, and 6E3 specificity

|  | 2C12 | 3F4 | 6E3 | Neg ctl | Pos ctl |
|---|---|---|---|---|---|
| FLNA aa1443-2131 | 3.320 | 3.040 | 2.570 | 0.072 | 3.845 |
| Full-Length FLNA | 1.868 | 2.355 | 2.199 | 0.043 | 3.090 |

TABLE 2-continued

ELISA test results on 2C12, 3F4, and 6E3 specificity

|  | 2C12 | 3F4 | 6E3 | Neg ctl | Pos ctl |
|---|---|---|---|---|---|
| FLNB aa1416-2089 | 0.379 | 0.711 | 0.398 | 0.069 | OVRFLW |
| Full-Length FLNB | 1.105 | 0.696 | 0.364 | 0.072 | OVRFLW |
| FLNC aa1438-2128 | 0.044 | 0.042 | 0.041 | 0.042 | 1.700 |
| 10% Pooled Normal Human Serum | 0.627 | 0.779 | 0.635 | 0.321 | N/A |

Antibody Characterization
Kinetics Studies

Figure 2:
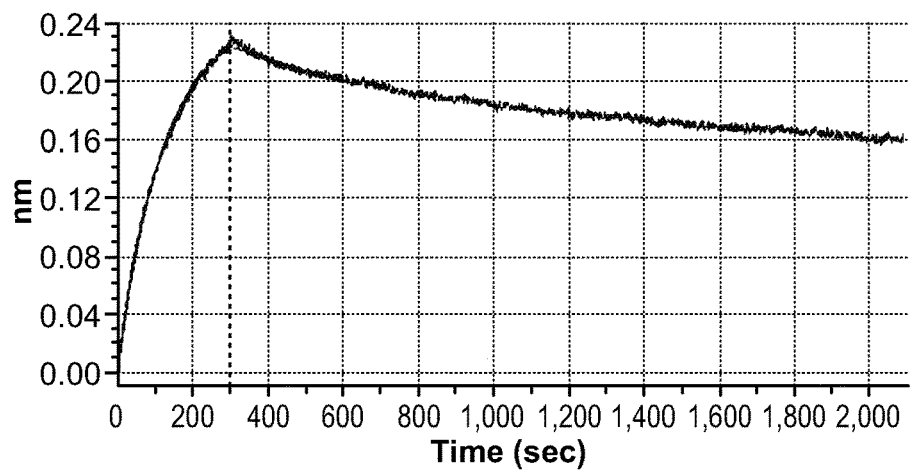
FIG. 2 shows the results of kinetics studies with ForteBio Bio-Layer Interferometry (BLI) technology.
Figure 2:
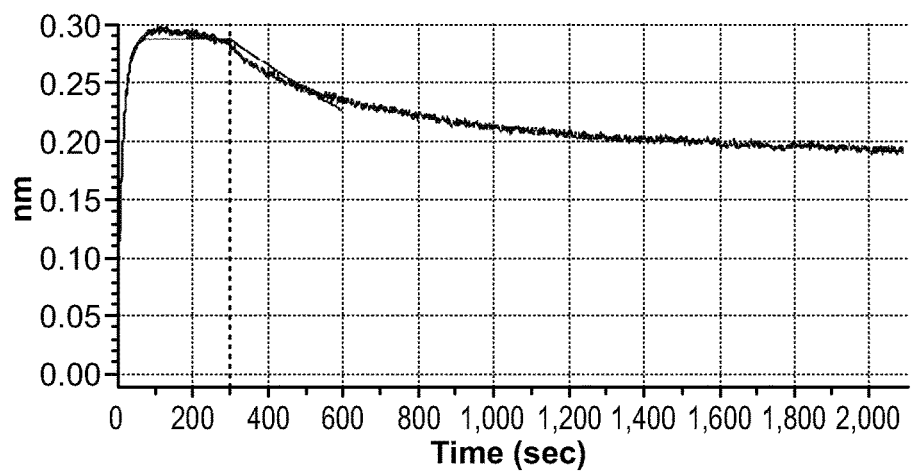
Figure 2:
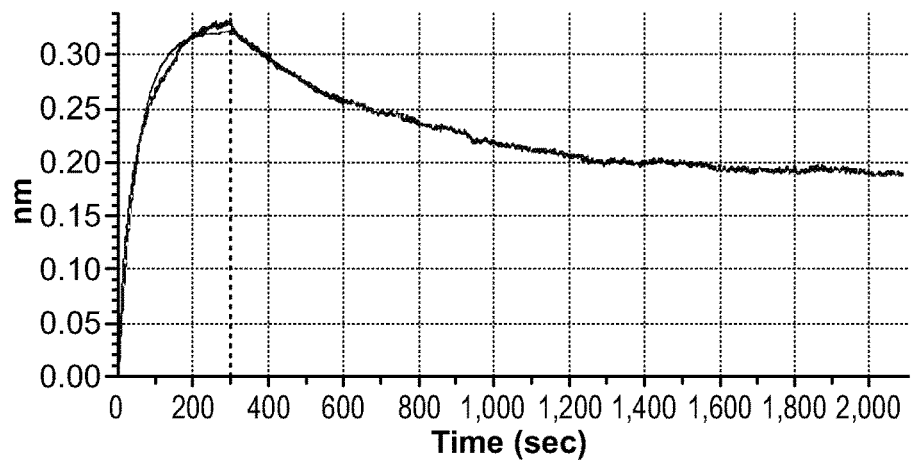

Kinetics studies with ForteBio Bio-Layer Interferometry (BLI) technology were carried out. BLI is a label-free technology for measuring biomolecular interactions. It is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time. The results are shown in FIG. 2. The Octet analysis results are shown as below in Table 3. Both antibodies show $K_D$ less than pM, suggesting their high affinity to the partial FLNA protein.

TABLE 3

Octet analysis of 2C12, 3F4, and 6E3 antibody binding kinetics to full length FLNA protein

| Clone | Sensor Type | Sample ID | Conc. (nM) | Response | KD (M) | kon(1/Ms) | Kdis (1/s) | Full X^2 | Full R^2 |
|---|---|---|---|---|---|---|---|---|---|
| 2C12 | AMC (Anti-mIgG Fc Capture) | FLNA Partial | 100 | 0.2224 | 4.82E−09 | 7.90E+04 | 3.81E−04 | 0.005684 | 0.996439 |
| 3F4 | AMC (Anti-mIgG Fc Capture) | FLNA Partial | 100 | 0.2831 | 9.99E−10 | 8.05E+05 | 8.04E−04 | 0.018584 | 0.97077 |
| 6E3 | AMC (Anti-mIgG Fc Capture) | FLNA Partial | 100 | 0.3299 | 4.02E−09 | 1.95E+05 | 7.84E−04 | 0.039811 | 0.975718 |

Antibody Isotype

Pierce rapid isotyping kit—mouse was used to decide the isotypes of the clones. According to results, 2C12 is IgG1/κ, 3F4 is IgG2b/κ, and 6E3 is IgG1/κ.

Sequencing

Hybridoma clones were sent to Fusion Antibodies for sequencing. mRNA was extracted and reverse-transcribed for PCR amplification of variable regions for sequencing. The results are as follows:

The heavy chain consensus amino acid sequence produced by the 2C12 hybridoma comprises SEQ ID NO: 25, shown below. In SEQ ID NO:25, the variable heavy domain is highlighted in bold.

SEQ ID NO: 25
MAVLGLLFCLVTFPSCVLSQVQLKQSGPGLVQPSQSLSITCTVSGFSLTN

YGVHWVRQSPGKGLEWLGVIWRGGSTDYNAAFMSRLSITKDNSKSQVFFK

MNSLQADDTAIYFCALRGNYVHYYLMDYWGQGTSVTVSSAKTTPPSVYPL

AP

The light chain consensus amino acid sequence produced by the 2C12 hybridoma comprises SEQ ID NO: 26, shown below. In SEQ ID NO:26, the variable light domain is highlighted in bold.

SEQ ID NO: 26
MVSTAQFLGLLLLCFQGTRCDIQVTQTPSSLSASLGDRVTISCRASQDIS
NYLNWYQQKPDGTVKLLIYYTSRLHSGVPSRFSGSGSGTDYSLTISNLDQ
EDIATYFCQQGNTLPPTFGGGTNLEIKRADAAPTVSIFPPSSEQLTSGGA
SVVCFLNNFYPK

The heavy chain consensus amino acid sequence produced by the 3F4 hybridoma comprises SEQ ID NO: 27, shown below. In SEQ ID NO:27, the variable heavy domain is highlighted in bold.

SEQ ID NO: 27
MMVLSLLYLLTALPGILSEVQLQESGPGLAKPSQTLSLTCSVTGYSITSN
YWNWIRKFPGNKLEYMGYISFSGSTYYNPSLKSRISITRDTSKNQYYLQL
NSVTTEDTATYYCARWNYYAMDYWGQGTSVTVSSAKTTPPSVFPLA

The light chain consensus amino acid sequence produced by the 3F4 hybridoma comprises SEQ ID NO: 28, shown below. In SEQ ID NO:28, the variable light domain is highlighted in bold.

SEQ ID NO: 28
MVSTAQFLVFLLFWIPASRGDFLLTQSPAILSVSPGERVSFSCRASQSIG
TNIHWYQQRTNGSPRLLIKFASESISGIPSRFSGSGSGTDFTLTINSVES
EDIADYYCQQSNSWPYTFGGGTKLEIKRADAAPTVSIFPPSSEQLTSGGA
SVVCFLNNFYPR

The heavy chain consensus amino acid sequence produced by the 6E3 hybridoma comprises SEQ ID NO: 29, shown below. In SEQ ID NO:29, the variable heavy domain is highlighted in bold.

SEQ ID NO: 29
MGWSWVMLFLLSVTAGVHSQVQLQQSGAELMKPGASVKLSCKATGYTFTG
YWIEWVKQRPGHGLEWIGEILPGNGSTNCNEKFKGKATFTATTSSNTAYM
QLSSLTTEDSAIYYCTTVSYWGQGTTLTVSSAKTTPPSVFPLA

The light chain consensus amino acid sequence produced by the 6E3 hybridoma comprises SEQ ID NO: 30, shown below. In SEQ ID NO:30, the variable light domain is highlighted in bold.

SEQ ID NO: 30
MKLPVRLLVLMFWIPASTSDVVMTQTPLSLPVSLGDQASISCRSSQSLVH
SNGNTYLHWYLQKPGQSPNLLIYKVSNRFSGVPDRFTGSGSGTDFTLKIS
RVEAEDLGVYFCSQSTHVPFTFGSGTKLEIKRADAAPTVSIFPPSSEQLT
SGGASVVCFLNNFYPK

Epitope Mapping

Figure 3:
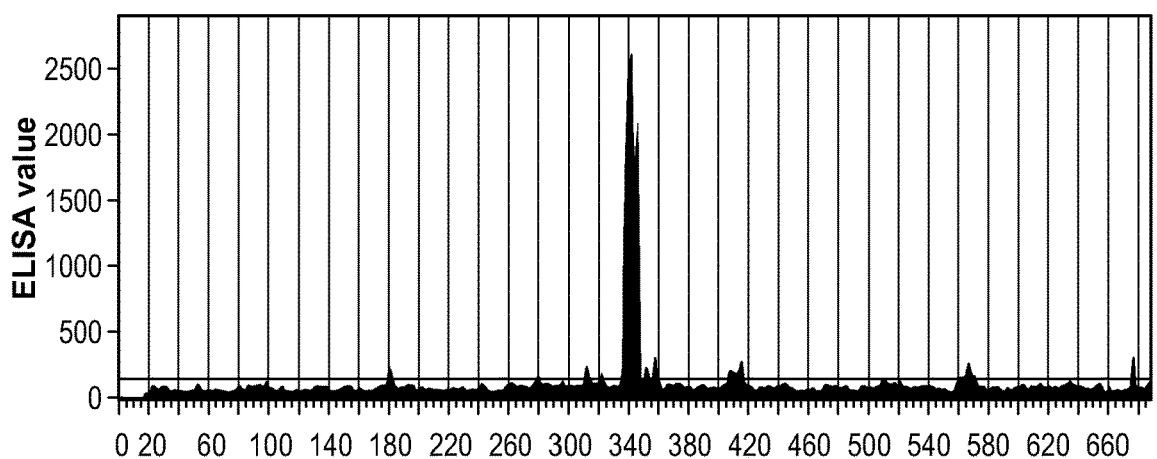
FIGS. 3 (A and B) shows that peptides containing motif ERPLVGV (SEQ ID NO: 42) are bound by anti-FLNA 6E3 antibody (A). The epitope of mab 6E3 (ERPLVGV) (SEQ ID NO: 42) is indicated at the top portion, superposed on all resolved structure depicted in cartoon representation (B).
Figure 3:
Figure 4:
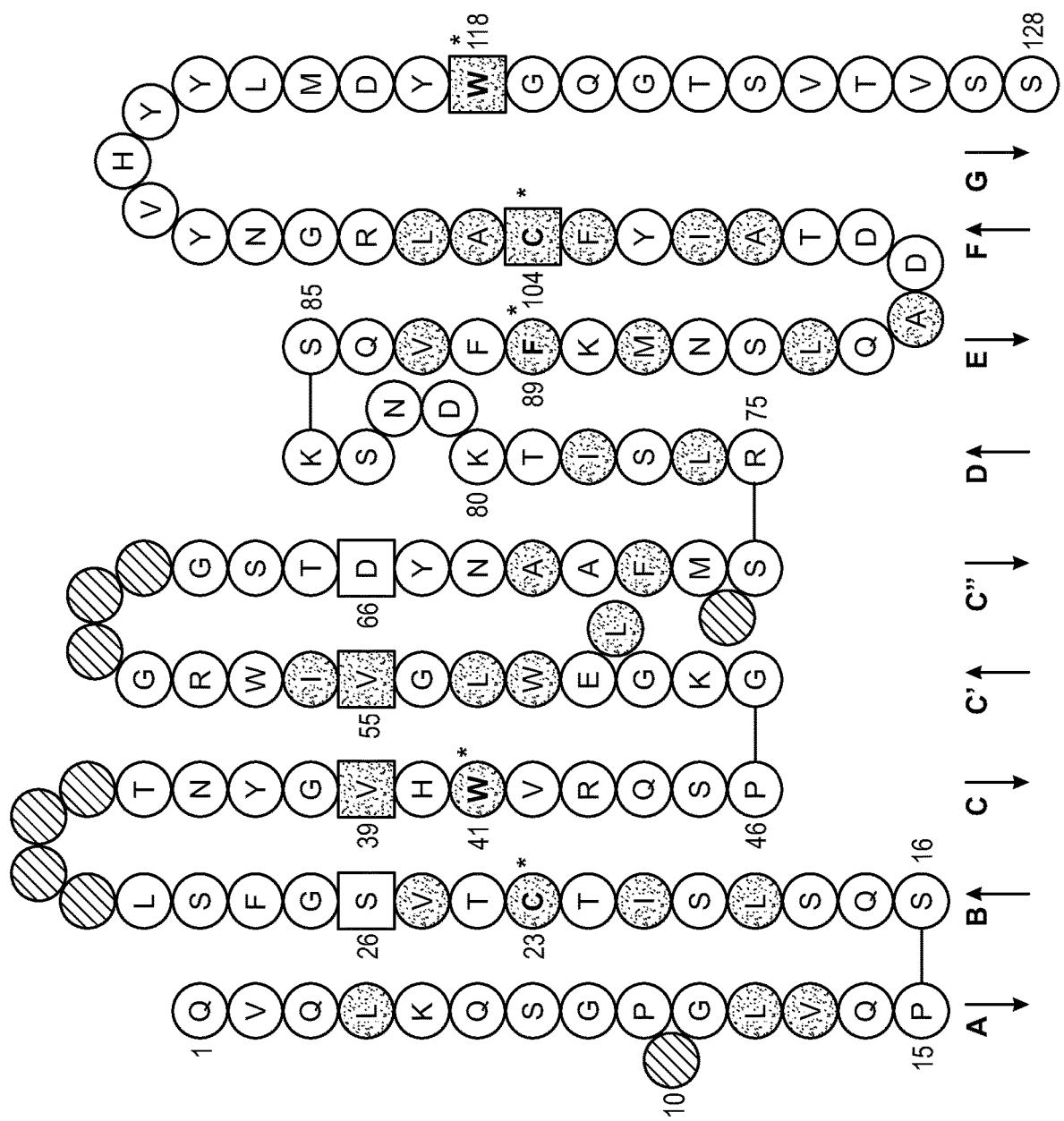
FIG. 4 shows a graphical representation of the CDR loops of the 2C12 clone variable heavy chain (SEQ ID NO: 1). Shaded circles are hydrophobic (non-polar) residues in frameworks 1-3 at sites that are hydrophobic in the majority of antibodies. Squares are key residues at the start and end of the CDR. Amino acids in the framework with an asterisk are structurally conserved amino acids.
Figure 5:
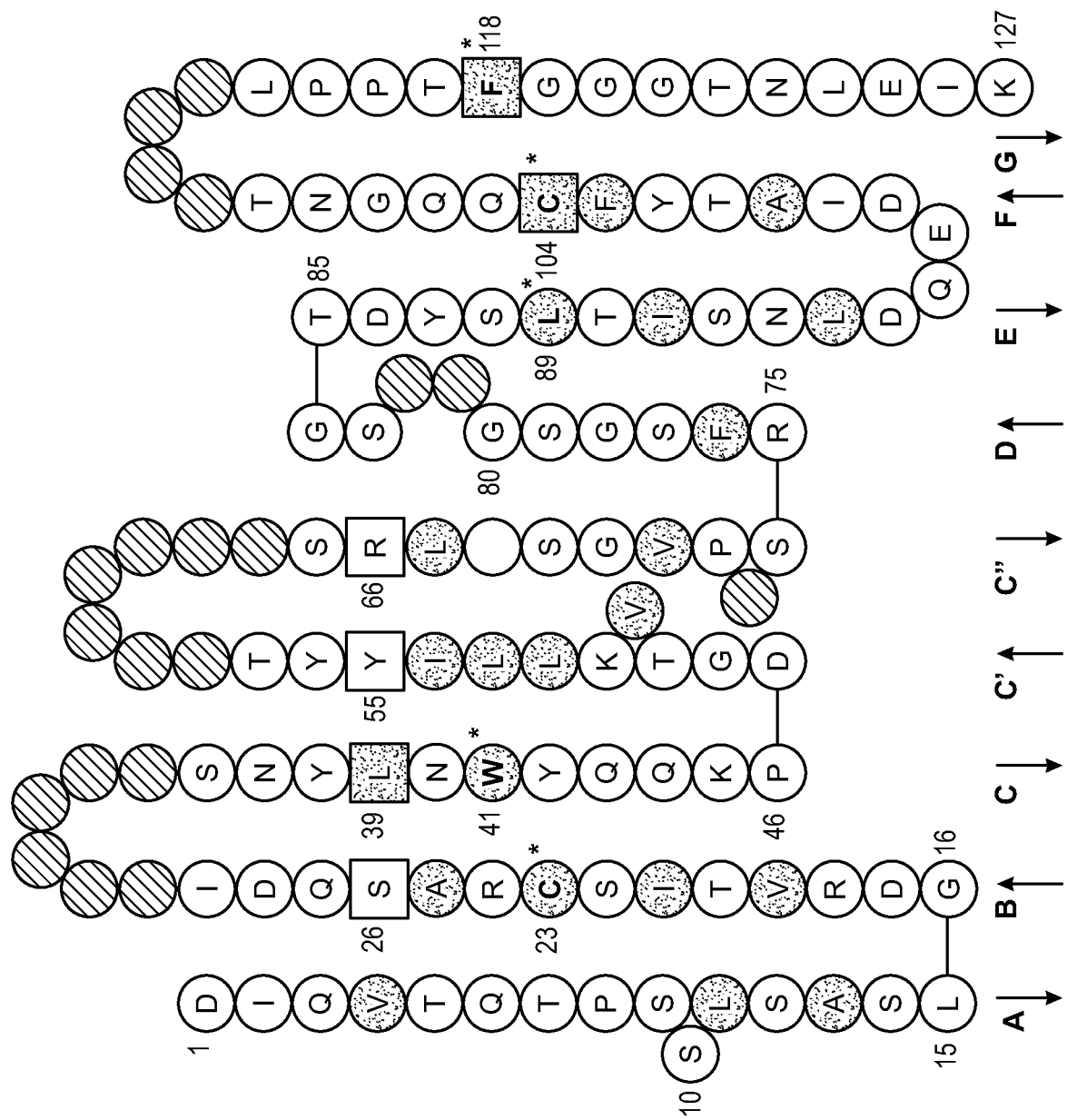
FIG. 5 shows a graphical representation of the CDR loops of the 2C12 clone variable light chain (SEQ ID NO: 2). Shaded circles are hydrophobic (non-polar) residues in frameworks 1-3 at sites that are hydrophobic in the majority of antibodies. Squares are key residues at the start and end of the CDR Amino acids in the framework with an asterisk are structurally conserved amino acids.
Figure 6:
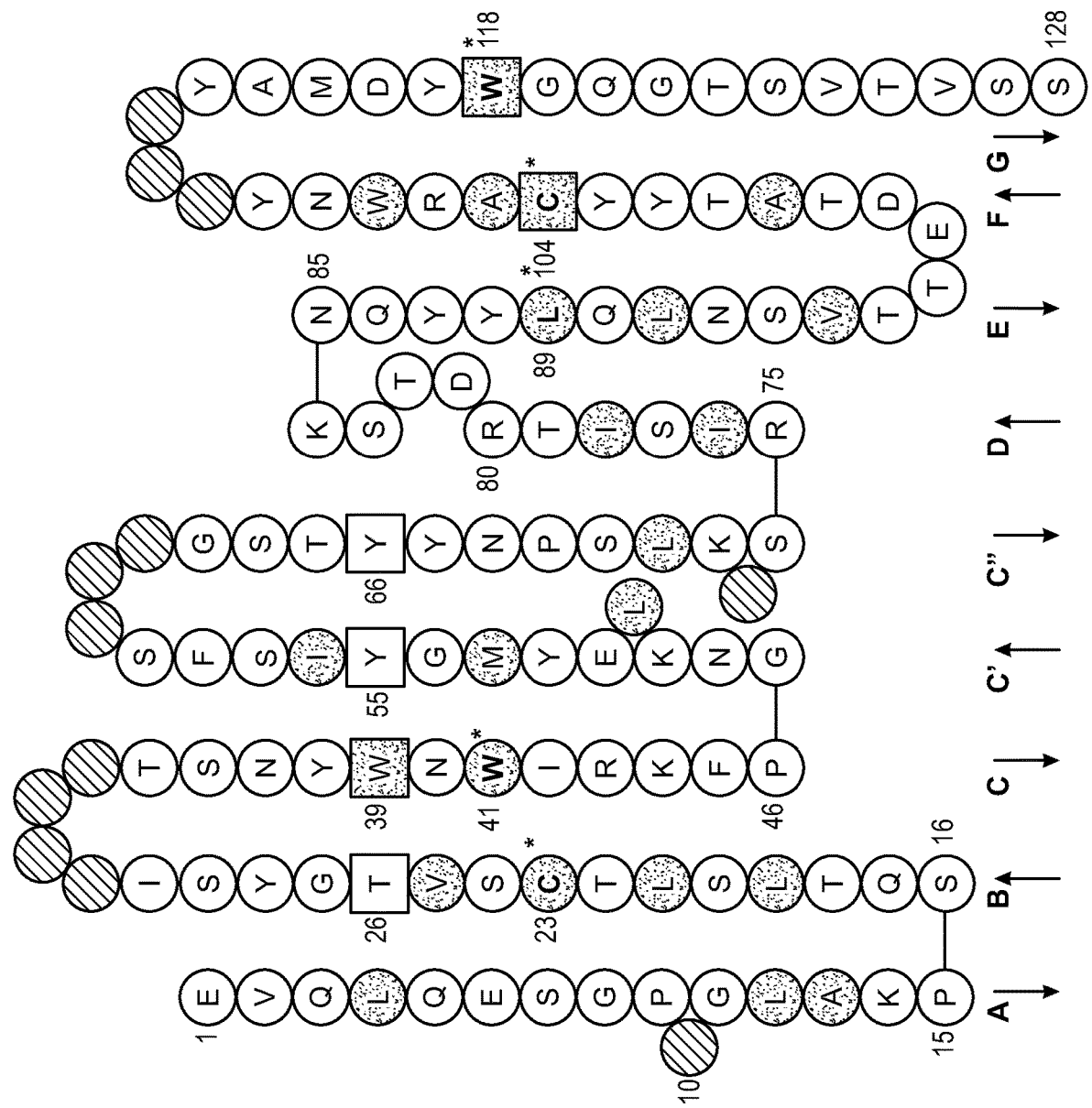
FIG. 6 shows a graphical representation of the CDR loops of the 3F4 clone variable heavy chain (SEQ ID NO: 3). Shaded circles are hydrophobic (non-polar) residues in frameworks 1-3 at sites that are hydrophobic in the majority of antibodies. Squares are key residues at the start and end of the CDR. Amino acids in the framework with an asterisk are structurally conserved amino acids.
Figure 7:
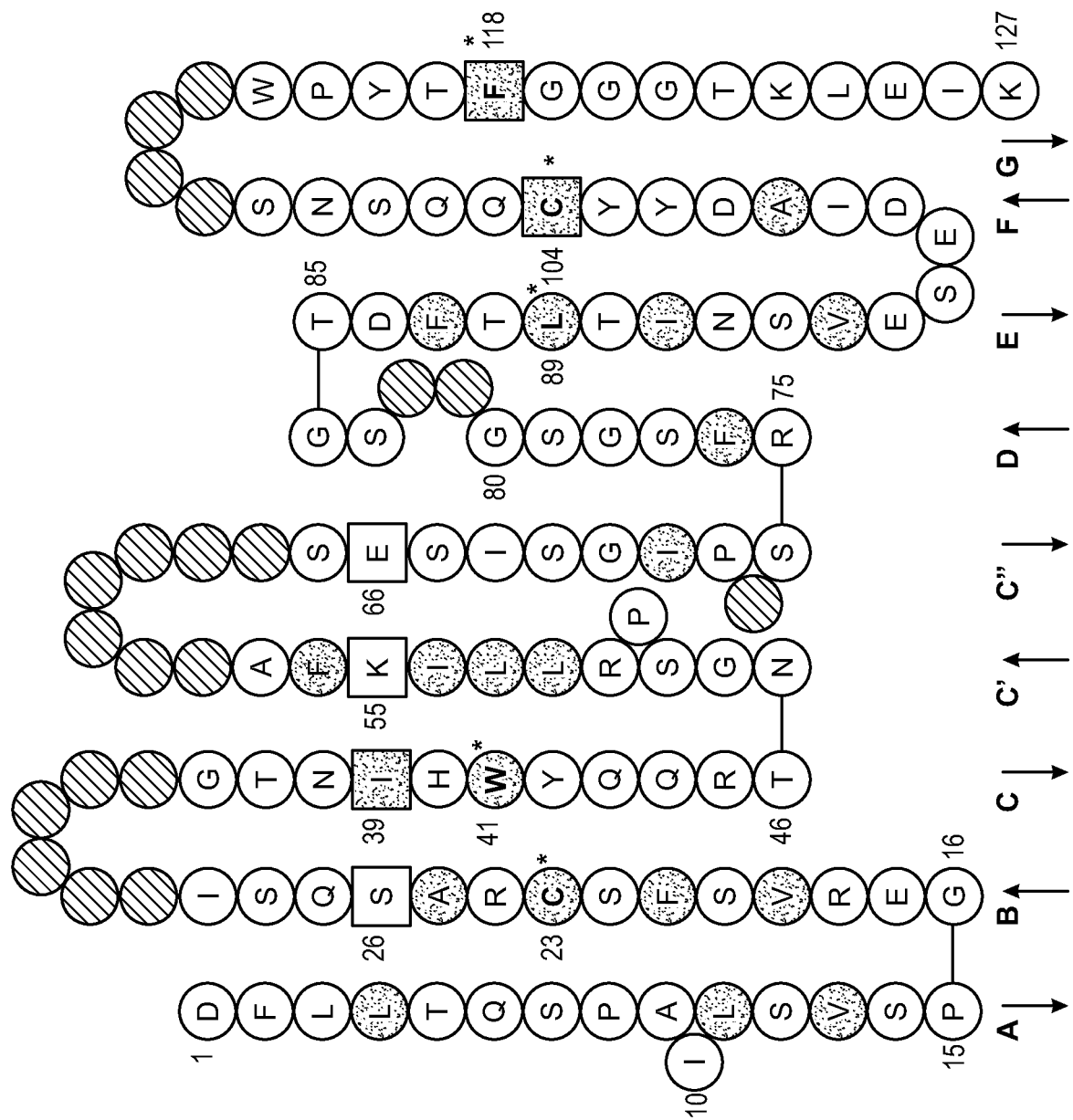
FIG. 7 shows a graphical representation of the CDR loops of the 3F4 clone variable light chain (SEQ ID NO: 4). Shaded circles are hydrophobic (non-polar) residues in frameworks 1-3 at sites that are hydrophobic in the majority of antibodies. Squares are key residues at the start and end of the CDR Amino acids in the framework with an asterisk are structurally conserved amino acids.
Figure 8:
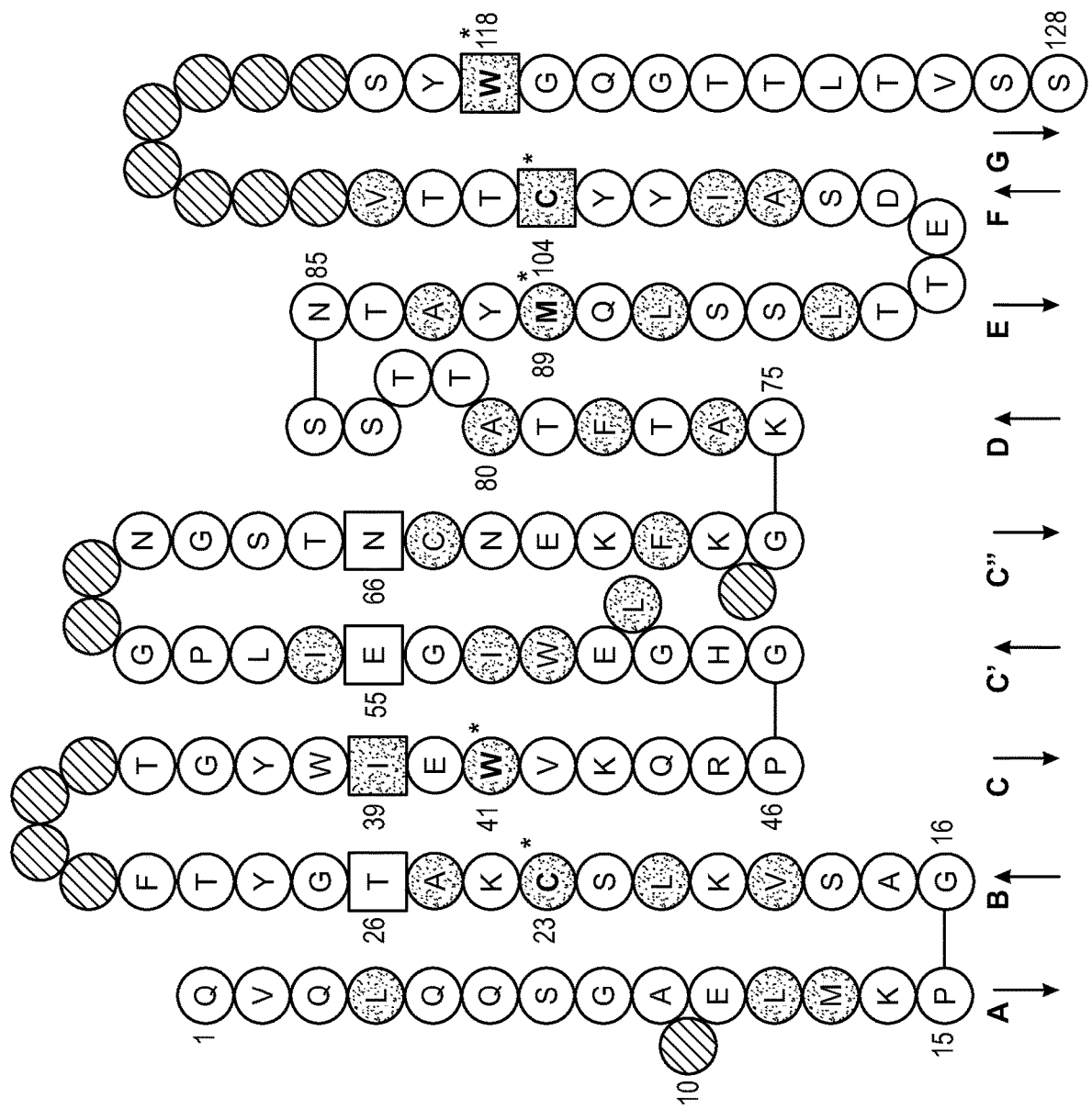
FIG. 8 shows a graphical representation of the CDR loops of the 6E3 clone variable heavy chain (SEQ ID NO: 5). Shaded circles are hydrophobic (non-polar) residues in frameworks 1-3 at sites that are hydrophobic in the majority of antibodies. Squares are key residues at the start and end of the CDR. Amino acids in the framework with an asterisk are structurally conserved amino acids.
Figure 9:
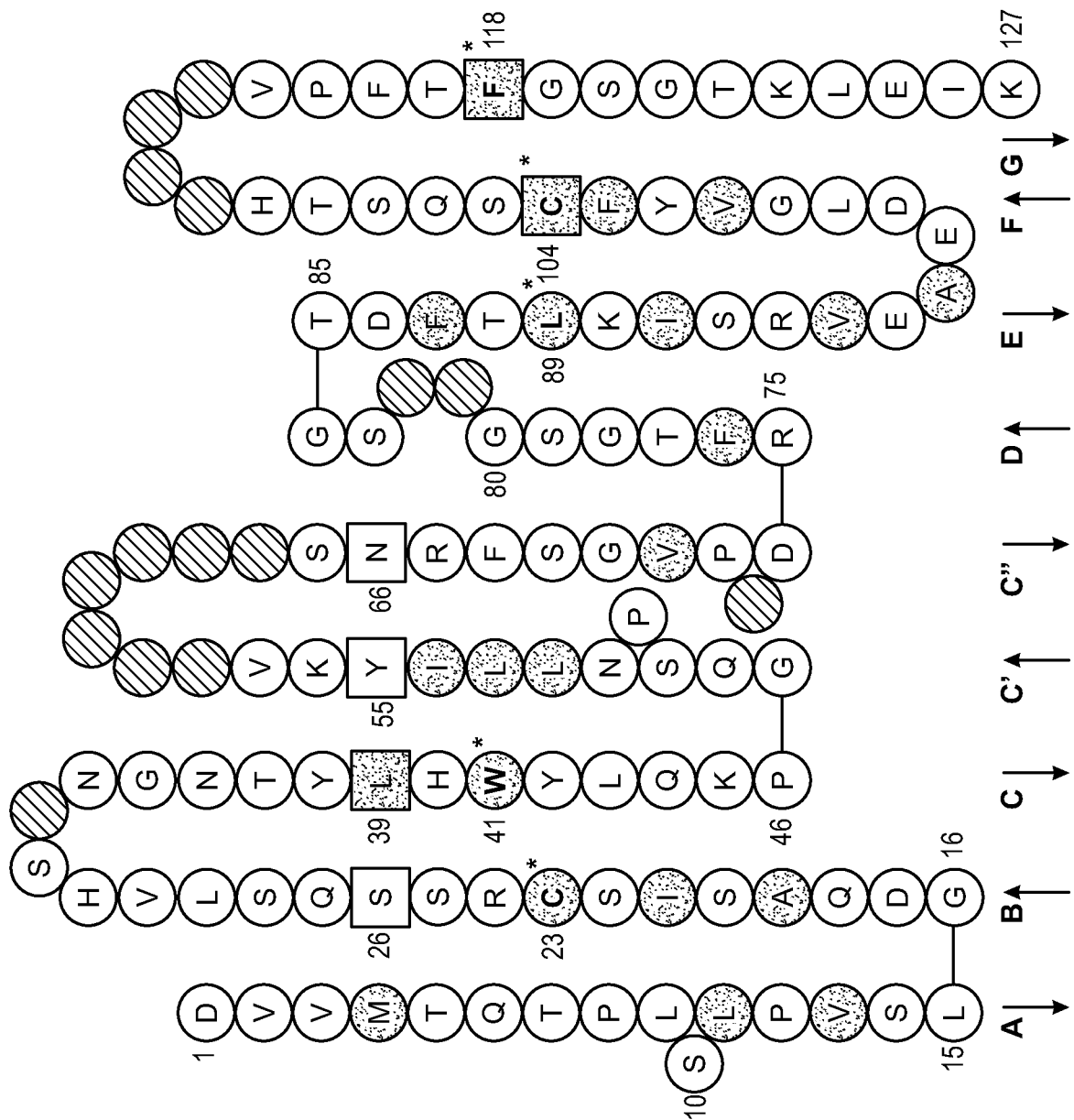
FIG. 9 shows a graphical representation of the CDR loops of the 6E3 clone variable light chain (SEQ ID NO: 6). Shaded circles are hydrophobic (non-polar) residues in frameworks 1-3 at sites that are hydrophobic in the majority of antibodies. Squares are key residues at the start and end of the CDR Amino acids in the framework with an asterisk are structurally conserved amino acids.

A HiSense linear array containing all linear 15 mer peptides with 13 residue overlap derived of the FLNA (aa 1443-2131) regions from the target proteins was constructed. The antibodies were probed on the array under different stringency conditions. Antibody 6E3 could be mapped to a linear motif ERPLVGV (SEQ ID NO: 42), corresponding to residue 1774-1780 in the hinge connecting Filamin domains 15 and 16 of the target protein. 2C12 and 3F4 failed this linear epitope mapping procedure, suggesting they may bind to conformational epitopes of the target instead of linear epitopes. The results from the epitope mapping studies are shown in FIGS. 3A and 3B.

In conclusion, C12 (IgG1/κ), 3F4 (IgG2b/κ), and 6E3 (IgG1/κ) murine monoclonal antibodies were developed that specifically recognize full length human FLNA protein with high affinity according to ELISA and Octet BLI analysis. The clones were nucleotide-sequenced for V region amino acid sequence with CDR regions determined by IMGT numbering system. All three antibodies were investigated for their binding epitopes by linear peptide library. 6E3 was determined to bind linear motif ERPLVGV (aa1774-1780) (SEQ ID NO: 42) in the hinge connecting Filamin domains 15 and 16 of the target protein, while 2C12 and 3F4 failed the specific binding to any sequence in the peptide library, suggesting conformational epitopes for these two antibodies.

Example 2: Stratification of Subjects with Prostate Cancer Using FLNA

Using the antibodies of the invention as described herein, FLNA levels can be used to distinguish subjects who are or are not suffering from prostate cancer.

A series of subject samples are obtained from an appropriate source, e.g., a commercial source, wherein the samples were obtained from subjects with different stages of prostate cancer, e.g., aggressive prostate cancer, androgen sensitive, androgen insensitive, metastatic; or from subjects not suffering from prostate cancer, e.g., subjects with normal prostate or subjects with BPH. The samples are analyzed for the expression level of FLNA and/or PSA. Optionally other markers, such as the expression level of keratin 19 and/or filamin B, the age of the subjects, or the prostate volume of the subjects, can also be analyzed in addition to filamin A and/or PSA. The level of FLNA and PSA correlate with the presence or absence of disease, and with the severity of prostate cancer.

Example 3: Monitoring of Prostate Cancer Treatment Using FLNA

At the time of diagnosis with prostate cancer, subjects are invited to participate in a trial. A subject sample, e.g., blood, is obtained. Periodically, throughout the monitoring, watchful waiting, or active treatment of the subject, e.g., chemotherapy, radiation therapy, e.g., radiation of the prostate, surgery, e.g., surgical prostate resection, hormone therapy, a new subject sample is obtained. At the end of the study, all subject samples are tested for the level of FLNA and/or PSA, and optionally other markers. The subject samples are matched to the medical records of the subjects to correlate FLNA and/or PSA levels, as appropriate, with prostate cancer status at the time of diagnosis, rate of progression of disease, response of subjects to one or more interventions, and transitions between androgen dependent and independent status. Other markers, such as the expression level of keratin 19 and/or filamin B, the age of the subjects, or the prostate volume of the subjects, can also be analyzed in addition to filamin A and/or PSA.

Example 4: Detection and Monitoring of Prostate Cancer Using FLNA

Despite its limitations, including a positive predictive value of only 25-40%, PSA remains the only generally accepted biomarker for prostate cancer. Moreover, as prostate cancer is most commonly a slow growing tumor in men of advanced age, treatment of the cancer may do more harm to the subject than the tumor itself would. Tests together to determine expression of FLNA and/or PSA, optionally in combination with other markers, in detection, including in routine, preventative, screening methods in men having an increased risk of prostate cancer (e.g., increased age, family history, race, etc.) or in monitoring of subjects diagnosed with prostate cancer prior to or during treatment may be useful to better identify subjects in need of further, potentially more invasive, diagnostic tests, e.g., prostate exam or biopsy, digital rectal exam; or more aggressive treatment. Detection of levels of expression of FLNA and/or PSA, may also be indicative of a good or poor response to a specific treatment regimen prior to changes in other signs or symptoms, e.g., loss of tumor response to hormone therapy.

In routine screening methods for prostate cancer, a serum sample from a subject is tested for the level of expression of FLNA and/or PSA, and optionally other markers, such as the expression level of keratin 19 and/or filamin B, the age of the subjects, or the prostate volume of the subjects. The levels are compared to one or more appropriate controls, e.g., other normal subjects, subjects with prostate cancer. Detection of an abnormal level of one or more of FLNA and/or PSA indicates that the subject should be considered for further tests for the presence of prostate cancer. Changes in the level of FLNA, optionally in combination with PSA in the subject may be more indicative of a change in prostate cancer status than comparison to a population control.

In embodiments where a diagnosis of prostate cancer is made, the invention also contemplates administering a therapeutic anti-cancer treatment, wherein the anti-cancer treatment is selected from the group consisting of (a) radiation therapy, (b) chemotherapy, (c) surgery, (d) hormone therapy, (e) antibody therapy, (f) immunotherapy, (g) cytokine therapy, (h) growth factor therapy, and (d) any combination of (a)-(h).

In determining a therapeutic regimen for a subject with prostate cancer not yet being actively treated for prostate cancer (i.e., watchful waiting) can be tested at regular intervals to determine if there is a change in the level of expression of FLNA and/or PSA. An increase in the level of FLNA and/or PSA indicates that the subject should be considered for further tests to monitor the prostate cancer and more active therapeutic interventions should be considered.

A subject undergoing treatment for prostate cancer (e.g., hormone therapy, chemotherapy, radiation therapy, e.g., radiation of the prostate, surgery, e.g., surgical prostate resection) is tested prior to the initiation of the treatment and during and/or after the treatment to determine if the treatment results in a change in the level of expression of one or more of FLNA and/or PSA. A decrease in the level of FLNA and/or PSA is indicative of response to treatment.

Example 5. Determination of Concentration of FLNA in Human Serum, EDTA and Lithium Heparin Plasma by Sandwich ELISA To quantify FLNA levels in human serum or plasma (EDTA plasma or lithium heparin plasma), the quantitative sandwich ELISA was performed using the antibodies of the invention as described herein.

Briefly, anti-FLNA antibody (6E3) was coated onto a microplate. The microplate was incubated overnight. Each well was then washed with Wash Buffer (0.05% Tween® 20 in PBS, pH 7.2-7.4; R and D Systems). Plates were blocked by adding Block Buffer (1% BSA in PBS, pH 7.2-7.4, 0.2 µm filtered; diluted 10 fold as per instructions; R and D Systems) to each well and removing the Block Buffer.

Serum or plasma samples as well as FLNA standards and controls were pipetted into the wells and any FLNA present was bound by the immobilized anti-FLNA antibody (6E3). For EDTA plasma samples, dilution was required due to high sample values. EDTA plasma samples was diluted 20-fold in Calibrator Diluent RD6E (1×) prior to assay. For serum and lithium heparin plasma samples, no extra preparation was necessary.

After washing away any unbound substances with Wash Buffer (four washes), a biotin-linked monoclonal antibody specific for FLNA (3F4) was added to the wells. Following incubation for two hours and four washes with Wash Buffer to remove any unbound biotinylated antibody, enzyme-linked streptavidin (Streptavidin-HRP, R and D Systems) was added and incubated for 30 minutes. Another four washes removed unbound enzyme-linked streptavidin, and a Substrate Solution (1:1 mixture of Color Reagent A ($H_2O_2$) and Color Reagent B (Tetramethylbenzidine; R and D Systems) was added to the wells, and incubated for 30 minutes.

Color developed in proportion to the amount of FLNA bound in the initial step. The color development was then stopped using Stop Solution (2N $H_2SO_4$; R and D Systems) and the intensity of the color was measured using a microplate reader set to 450 nm with a 540 or 570 nm correction wavelength, which corresponded to the concentration of FLNA in the sample. Alternate combinations of the three anti-FLNA antibodies, 2C12, 3F4 and 6E3, for use as a coating and detection antibody, to the one described currently in the example, can also be used for this assay.

This ELISA assay successfully detected FLNA levels in the range of 3.125-200 ng/ml, with no cross reactivity to FLNB. Table 4 shows the FLNA ELISA validation summary.

TABLE 4

FLNA ELISA Validation Summary

| Study | FLNA |
|---|---|
| Analytical Range | 3.13 ng/ml to 200 ng/ml |
| $R^2$ of calibration curves | ≥0.99 |
| Intra-day Precision | CV < 10% (n = 8) |
| Inter-day Precision | CV < 8.7% (n = 41) |
| Spike Recovery in serum | 124% |
| Dilutional Linearity in serum | % bias <20% for up to 1:8 dilution |
| Freeze-Thaw Stability in serum | Stable up to 3 freeze-thaw cycles |
| Short-term Stability in serum | Stable for 2 hours at room temperature and at 6 hours at 4° C. |
| Long-term Stability in serum | Stable for up to 1 year at −80° C. |
| Interfering Substances in serum | No interference for levels below 250 mg/dL Hemoglobin; 30 mg/dL Bilirubin; 1000 mg/dL Lipoproteins |
| Specificity in serum | No cross reactivity with FLNB protein at 10 pM |

Example 6. Determination of the Concentration of FLNA Peptides from Human Serum Using Overnight Immunoprecipitation and LC-MS/MS (MRM) Analysis Since FLNA is a low abundance protein in human serum and plasma matrices, development of quantitative mass spectrometry based assays was challenging. To improve sensitivity of the assay, an immunoaffinity enrichment approach (immunoprecipitation (IP)) coupled with multiple reaction monitoring (MRM) was developed using the antibodies described herein. The IPMRM approach, as described below, is feasible for FLNA in serum matrix.

IPMRM combines IP with mass spectrometry and allows the rapid quantitation of proteins with enhanced sensitivity and specificity. For biomarkers, this technique has shown to achieve low ng/mL quantitation by selective enrichment of target proteins in complex matrices (see Nicol G R, et al. (2008) Molecular & Cellular Proteomics 7 (10):1974-1982; Kulasingam V, et al. (2008) Journal of Proteome Research 7 (2):640-647; Berna M, Ackermann B (2009) Anal Chem 81 (10):3950-3956, the contents of which are incorporated herein by reference).

Antibody Immobilization:

Anti-FLNA monoclonal antibodies 2C12, 3F4 and 6E3 were immobilized onto an agarose support using the ThermoFisher Scientific Pierce Direct IP Kit (ThermoFisher Scientific) according to the manufacturer's protocol with a few modifications. 200 µg of each of the three antibodies were coupled individually to 200 µL of AminoLink Plus coupling resin and stored at 4° C. until needed.

Immunoprecipitation and Preparation of Calibration Standards:

Immunoprecipitation was performed using the Pierce Direct IP Kit (ThermoFisher Scientific) according to the manufacturer's protocol with few modifications. Immunoprecipitation tubes were prepared by aliquoting 15 µL of antibody-coupled resins into the IP tube (Pierce Direct IP Kit, ThermoFisher Scientific). The resin was washed twice with 200 µL of IP lysis/wash buffer. 100 µL of sample or 100 µL of water (surrogate matrix) was added to each IP tube along with 500 µL of prepared lysis buffer solution (IP lysis/wash buffer with 1.2×Halt protease cocktail inhibitor (ThermoFisher Scientific) and 0.5 M EDTA and incubated overnight at 4° C. with end-over-end mixing. The resin was washed five times with 200 µL of IP lysis/wash buffer and once with 100 µL of 1× conditioning buffer. The captured proteins were eluted with 50 µL of elution buffer with an incubation time of 15 minutes and neutralized with 5 µL of 1M Tris HCl, pH 9.0 (Teknova, Hollister, CA). The IP eluates from the surrogate matrix were used to prepare peptide 2 (P2) (AGVAPLQVK) (SEQ ID NO:40) and peptide 4 (P4) (YNEQHVPGSPFTAR) (SEQ ID NO:41) peptide calibration curves by spiking with a P2/P4 synthetic peptide (Genscript, Piscataway, NJ) stock solution (0.2/0.36 µg/mL) followed by serial dilution. P2 and P4 calibration standards ranged from 62.5 pg/mL to 1500 pg/mL and 563 pg/mL to 27000 pg/mL, respectively. All samples were then subjected to trypsin digestion.

Digestion of IP Extracted Samples:

Trypsin digestion was performed using the SMART Digest Kit (ThermoFisher Scientific) following the manufacturer's protocol with few modifications. 50 µL of samples or controls were transferred to labeled SMART Digest tubes Immediately before use, SMART Digestion buffer was combined in a glass vial with IS Sub-stock B in a 5:1 ratio to generate the Working IS solution. 30 µL of the Working IS solution was added to each tube using a repeater and dispensing over the tube without touching the tip. Samples were put in the ThermoMixer C and digestion occurred at approximately 70° C. for 20 minutes at 1000 rpm. After digestion was complete, the SMART Digest tubes were put in a 96 well-plate and centrifuged for 5 minutes at approximately 1500×g (rcf) and 5° C. using the plate centrifuge. 60 µL of the supernatant was then transferred to appropriately labeled LC-MS vials for LC-MS/MS for analysis.

LC-MS/MS (MRM) Analysis:

MRM analyses were performed on a 6500 QTRAP mass spectrometer (Sciex) equipped with an electrospray source, a 1290 Infinity UPLC system (Agilent Technologies, Santa Clara, CA) and a XBridge Peptide BEH300 C18 (3.5 µm, 2.1 mm×150 mm) column (Waters, Milford, MA). Liquid chromatography was carried out at a flow rate of 400 µL/min, and the sample injection volume was 25 µL. Mobile phase A consisted of 0.1% formic acid (Sigma Aldrich) in water (ThermoFisher Scientific) and mobile phase B consisted of 0.1% formic acid in acetonitrile (ThermoFisher Scientific). The gradient with respect to % B was as follows: 0 to 1.5 min, 5%; 1.5 to 2 min, 5% to 15%; 2 to 5 min, 15%; 5 to 7.1 min, 15% to 20%; 7.1 to 8.1 min, 20% to 80%; 8.1 to 9.0 min, 80%; and 9.0 to 9.1 min, 80% to 5%. 9.1 to 16 min, 5%. The instrument parameters for 6500 QTRAP mass spectrometer were as follows: Ion spray voltage of 5500 V, curtain gas of 20 psi, collision gas set to "medium", interface heater temperature of 400° C., nebulizer gas (GS1) of 80 psi and ion source gas (GS2) of 80 psi and unit resolution for both Q1 and Q3 quadrupoles.

Selection of Surrogate Peptides and MRM Transitions:

Two surrogate peptides, peptide 2 (AGVAPLQVK) (SEQ ID NO:40) and peptide 4 (YNEQHVPGSPFTAR) (SEQ ID NO:41) were selected based on surrogate peptide selection rules (see Halquist et al, 2011, *Biomed Chromatography* 25: 47-58, the contents of which are incorporated herein by reference) and signal intensities of the peptides in spiked and unspiked serum digests. The uniqueness of the surrogate peptides to the target protein was confirmed by running BLAST searches. Heavy labeled versions of the surrogate peptide 2 and 4, AGVAPLQV[K(13C6; 15N2)] (SEQ ID NO:40) and YNEQHVPGSPFTA[R(13C6; 15N4)] (SEQ ID NO:41) were used as internal standards. MRM transitions were optimized using synthetic surrogate peptides (GenScript) and their internal standards (ThermoFisher Scientific) and the following m/z transitions were monitored: P2, 441.7 $(M+2H)^{2+} \rightarrow 584.5$ $(y_5^{1+})$; P4 535 $(M+3H)^{3+} \rightarrow 832.4$ $(y_8^{1+})$; P2_IS 445.5 $(M+2H)^{2+} \rightarrow 592.1$ $(y_5^{1+})$; and P4_IS, 538.4 $(M+3H)^{3+} \rightarrow 842.5$ $(y_8^{1+})$.

IPMRM Data Analysis and Quantitation

Data analysis was performed using the Analyst® software (version 1.6.2, AB Sciex, Framingham, MA) and peak integrations were reviewed manually. The calibration curve for FLNA P2 and P4 peptides was constructed by plotting the peak area ratios (analyte/internal standard) versus concentration of the standard with $1/x^2$ linear least square regression. The regression equations from P2 and P4 calibration standards was used to back-calculate the measured P2 and P4 concentrations for each QC and unknown sample.

Based on the calculation, the FLNA IPMRM allowed detection of FLNA peptides from human serum in the range of 62.5 pg/ml to 1500 pg/ml for peptide 2, and 563 pg/ml to 27000 pg/ml for peptide 4.

FLNA IPMRM development involved optimization of several parameters including: selection of antibodies, immobilization, immunoaffinity capture, incubation, elution, trypsin digestion and other mass spectrometry parameters. The performance of the FLNA IPMRM was assessed using serum QCs and the assay met validation acceptance criteria.

Example 7. FLNA IPMRM Method Advancements

In order to improve the robustness of the IPMRM assay, several modifications were developed, in particular to optimize the conjugation process. First, the antibodies used in the assay were optimized. Instead of using all three anti-FLNA antibodies 2C12, 3F4 and 6E3, as described in Example 6, only antibodies 2C12 and 3F4 were used and 6E3 was no longer included. The amount of these two antibodies was varied and it was found that using a 1:2 ratio of 2C12:3F4 was optimal. Second, the volume of antibody conjugated resin for immunoprecipitation was increased from 15 μL to 45 μL. Third, the peptide curve (in water) that was employed in Example 6, which was only spiked after immunoprecipitation and thus could not track immunoprecipitation and digestion, was replaced with a protein curve (in 5% BSA) that undergoes immunoprecipitation and digestion, just as the samples do. Lastly, the time for liquid chromatography gradient was shortened from 16 minutes to 12 minutes without compromising assay integrity. These method improvements successfully increased the robustness of the assay.

Figure 10:
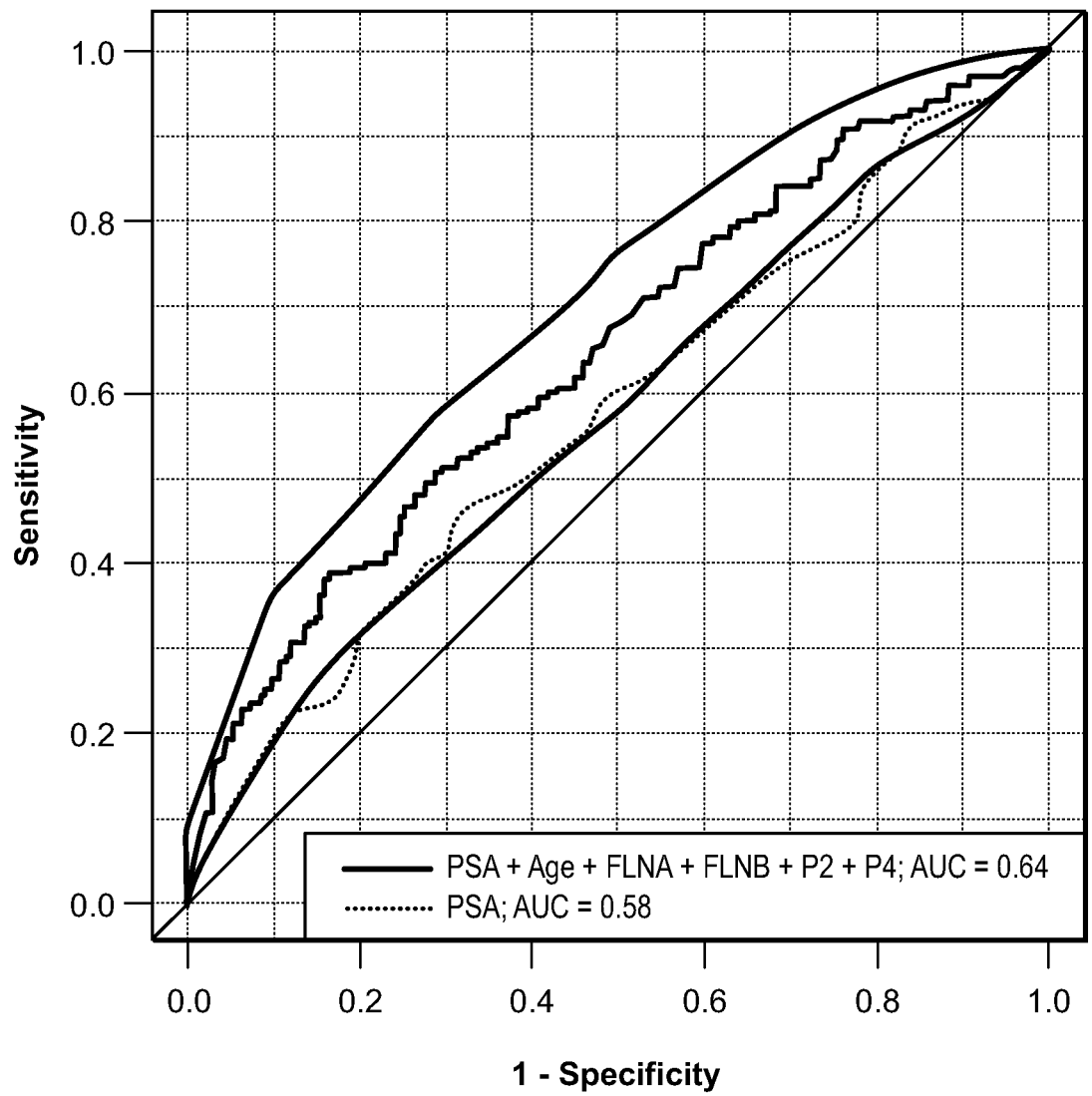
FIG. 10 shows a ROC curve of regression models using a prostate biomarker panel, age and PSA test compared to PSA alone. Specifically, the Prostate Biomarker Panel (FLNA, FLNB, age and PSA) predicts prostate cancer more accurately than PSA alone between patients with or without prostate cancer (Prostate Biomarker Panel (FLNA, FLNB, age and PSA) AUC, 0.64 (0.59, 0.69) (solid line), PSA alone AUC, 0.58 (dotted line)).

Example 8. Use of Anti-FLNA Antibodies and IPMRM for Analysis of Serum Samples from Patients Serum samples from patients were tested with the FLNA IPMRM, as described above, using the anti-FLNA monoclonal antibodies of the invention. The results were combined with data on age, PSA, and Gleason score and subjected to regression modelling. As shown in FIG. 10, a Prostate Cancer Biomarker Panel consisting of biomarkers FLNA, FLNB, age and PSA improved the classification of prediction of prostate cancer over PSA alone (AUC=0.64, [0.59, 0.69], vs 0.58).

Figure 11:
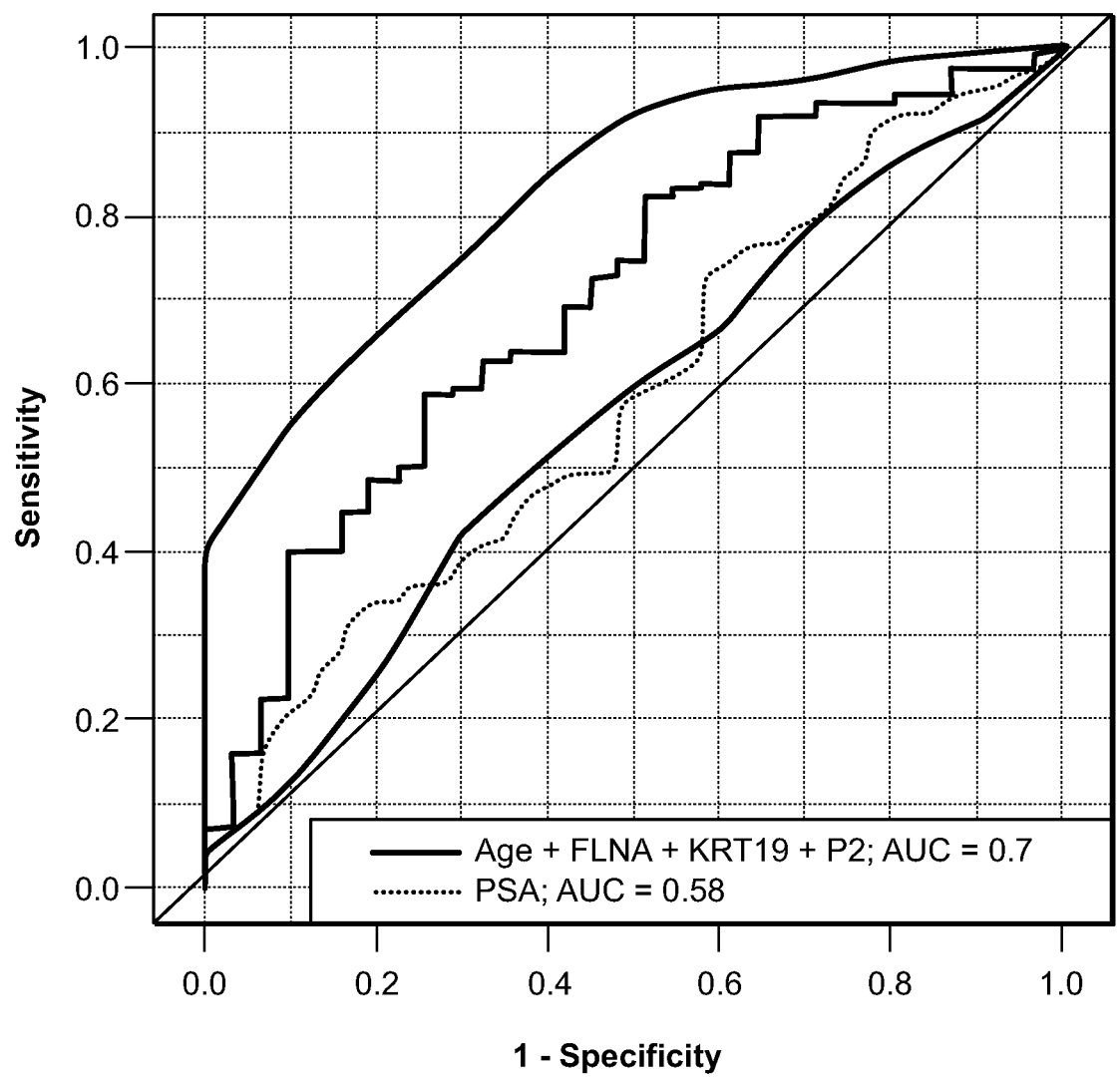
FIG. 11 shows a ROC curve of regression models using a prostate biomarker panel, age and PSA test compared to PSA alone. Specifically, the prostate biomarkers FLNA, KRT19 and age with PSA discriminates between prostate cancer and benign prostatic hyperplasia (BPH) over use of PSA alone (Prostate panel (FLNA, KRT19, PSA and age) (solid line) AUC, 0.70, (0.60, 0.80), PSA alone AUC, 0.58 (dotted line)).

Samples of patient serum were also analyzed for the biomarkers FLNA, keratin 19 (KRT19) and age combined, versus PSA alone. FIG. 11 shows that the biomarkers FLNA, KRT19 and age have improved classification of prediction between patients with benign prostatic hyperplasia versus prostate cancer over PSA alone (AUC=0.70 [0.60, 0.80], vs 0.58).

EQUIVALENTS

Those skilled in the art will recognize, or be able to ascertain using no more than routine experimentation, many equivalents to the specific embodiments and methods described herein. Such equivalents are intended to be encompassed by the scope of the following claims.

SEQUENCE LISTING

| Sequence Identifier | Protein or Nucleic Acid |
| --- | --- |
| SEQ ID NO: 1 | 2C12 variable heavy (VH) domain |
| SEQ ID NO: 2 | 2C12 variable light (VL) domain |
| SEQ ID NO: 3 | 3F4 variable heavy (VH) domain |
| SEQ ID NO: 4 | 3F4 variable light (VL) domain |
| SEQ ID NO: 5 | 6E3 variable heavy (VH) domain |
| SEQ ID NO: 6 | 6E3 variable light (VL) domain |
| SEQ ID NO: 7 | 2C12 VH CDR1 |
| SEQ ID NO: 8 | 2C12 VH CDR2 |
| SEQ ID NO: 9 | 2C12 VH CDR3 |
| SEQ ID NO: 10 | 2C12 VL CDR1 |
| SEQ ID NO: 11 | 2C12 VL CDR2 |
| SEQ ID NO: 12 | 2C12 VL CDR3 |
| SEQ ID NO: 13 | 3F4 VH CDR1 |
| SEQ ID NO: 14 | 3F4 VH CDR2 |
| SEQ ID NO: 15 | 3F4 VH CDR3 |
| SEQ ID NO: 16 | 3F4 VL CDR1 |
| SEQ ID NO: 17 | 3F4 VL CDR2 |
| SEQ ID NO: 18 | 3F4 VL CDR3 |
| SEQ ID NO: 19 | 6E3 VH CDR1 |
| SEQ ID NO: 20 | 6E3 VH CDR2 |
| SEQ ID NO: 21 | 6E3 VH CDR3 |
| SEQ ID NO: 22 | 6E3 VL CDR1 |
| SEQ ID NO: 23 | 6E3 VL CDR2 |
| SEQ ID NO: 24 | 6E3 VL CDR3 |
| SEQ ID NO: 25 | 2C12 hybridoma clone heavy chain consensus |
| SEQ ID NO: 26 | 2C12 hybridoma clone light chain consensus |
| SEQ ID NO: 27 | 3F4 hybridoma clone heavy chain consensus |
| SEQ ID NO: 28 | 3F4 hybridoma clone light chain consensus |
| SEQ ID NO: 29 | 6E3 hybridoma clone heavy chain consensus |
| SEQ ID NO: 30 | 6E3 hybridoma clone light chain consensus |
| SEQ ID NO: 31 | Filamin A, isoform 1 |
| SEQ ID NO: 32 | Filamin A, isoform 1 |
| SEQ ID NO: 33 | Filamin A, isoform 2 |
| SEQ ID NO: 34 | Filamin A, isoform 2 |
| SEQ ID NO: 35 | Filamin A immunogen |
| SEQ ID NO: 36 | Full length filamin A |
| SEQ ID NO: 37 | Partial filamin B (aa1416-2089) |
| SEQ ID NO: 38 | Partial filamin C (aa 1438-2128) |
| SEQ ID NO: 39 | Full length filamin B |
| SEQ ID NO: 40 | Peptide |
| SEQ ID NO: 41 | Peptide |

We claim:

1. A method for detecting and/or quantifying the level of FLNA in a sample, comprising contacting the sample with an antibody construct, or antigen-binding fragment thereof, capable of binding filamin A (FLNA) comprising (i) a heavy chain variable region comprising a CDR3 domain comprising the amino acid sequence set forth in SEQ ID NO: 9, a CDR2 domain comprising the amino acid sequence set forth in SEQ ID NO: 8, and a CDR1 domain comprising the amino acid sequence set forth in SEQ ID NO: 7, and a light chain variable region comprising a CDR3 domain comprising the amino acid sequence set forth in SEQ ID NO: 12, a CDR2 domain comprising the amino acid sequence set forth in SEQ ID NO: 11, and a CDR1 domain comprising the amino acid sequence set forth in SEQ ID NO: 10; or (ii) a heavy chain variable region comprising a CDR3 domain comprising the amino acid sequence set forth in SEQ ID NO: 15, a CDR2 domain comprising the amino acid sequence set forth in SEQ ID NO: 14, and a CDR1 domain comprising the amino acid sequence set forth in SEQ ID NO: 13, and a light chain variable region comprising a CDR3 domain comprising the amino acid sequence set forth in SEQ ID NO: 18, a CDR2 domain comprising the amino acid sequence set forth in SEQ ID NO: 17, and a CDR1 domain comprising the amino acid sequence set forth in SEQ ID NO: 16; or (iii) a heavy chain variable region comprising a CDR3 domain comprising the amino acid sequence set forth in SEQ ID NO: 21, a CDR2 domain comprising the amino acid sequence set forth in SEQ ID NO: 20, and a CDR1 domain comprising the amino acid sequence set forth in SEQ ID NO: 19, and a light chain variable region comprising a CDR3 domain comprising the amino acid sequence set forth in SEQ ID NO: 24, a CDR2 domain comprising the amino acid sequence set forth in SEQ ID NO: 23, and a CDR1 domain comprising the amino acid sequence set forth in SEQ ID NO: 22 under conditions such that the antibody construct or antigen-binding fragment thereof binds to FLNA in the sample, to thereby detect and/or quantify the level of FLNA in a sample.

2. The method of claim 1, comprising detecting and/or quantifying one or more surrogate peptides in a protein digest prepared from said sample using mass spectrometry, wherein the mass spectrometry is multiple reaction monitoring (MRM) mass spectrometry.

3. The method of claim 2, wherein the MRM is immunoprecipitation-multiple reaction monitoring (IPMRM) comprising a FLNA immunoprecipitation step.

4. The method of claim 2, wherein the one or more surrogate peptides comprise the amino acid sequence of SEQ ID NO:40 (P2) and/or SEQ ID NO:41 (P4).

5. The method of claim 4, wherein the range of detection for P2 is 62.5 pg/mL to 1500 pg/mL and the range of detection for P4 is 563 pg/mL to 27000 pg/mL.

6. The method of claim 4, wherein a P2 internal standard (P2_IS) and/or a P4 internal standard (P4_IS) is also detected.

7. The method of claim 6, wherein the MRM comprises monitoring one or more mass transitions m/z selected from the group consisting of: 441.7 $(M+2H)^{2+} \rightarrow 584.5$ $(y_5^{1+})$ for P2; 535 $(M+3H)^{3+} \rightarrow 832.4$ $(y_8^{1+})$ for P4, 445.5 $(M+2H)^{2+} \rightarrow 592.1$ $(y_5^{1+})$ for the P2 internal standard (P2_IS), and 538.4 $(M+3H)^{3+} \rightarrow 842.5$ $(y_8^{1+})$ for the P4 internal standard P4_IS.

8. A method for detecting and/or quantifying the level of FLNA in a sample, comprising detecting and/or quantifying one or more surrogate peptides, wherein the one or more surrogate peptides comprise the amino acid sequence of SEQ ID NO:40 (P2) and/or SEQ ID NO:41 (P4), in a protein digest prepared from said sample using mass spectrometry, wherein the mass spectrometry is multiple reaction monitoring (MRM) mass spectrometry, wherein the MRM is immunoprecipitation-multiple reaction monitoring (IP-MRM) comprising a FLNA immunoprecipitation step, and wherein the immunoprecipitation step is carried out using an antibody construct, or antigen-binding fragment thereof, capable of binding filamin A (FLNA) comprising
  (i) a heavy chain variable region comprising a CDR3 domain comprising the amino acid sequence set forth in SEQ ID NO: 9, a CDR2 domain comprising the amino acid sequence set forth in SEQ ID NO: 8, and a CDR1 domain comprising the amino acid sequence set forth in SEQ ID NO: 7, and a light chain variable region comprising a CDR3 domain comprising the amino acid sequence set forth in SEQ ID NO: 12, a CDR2 domain comprising the amino acid sequence set forth in SEQ ID NO: 11, and a CDR1 domain comprising the amino acid sequence set forth in SEQ ID NO: 10; or
  (ii) a heavy chain variable region comprising a CDR3 domain comprising the amino acid sequence set forth in SEQ ID NO: 15, a CDR2 domain comprising the amino acid sequence set forth in SEQ ID NO: 14, and a CDR1 domain comprising the amino acid sequence set forth in SEQ ID NO: 13, and a light chain variable region comprising a CDR3 domain comprising the amino acid sequence set forth in SEQ ID NO: 18, a CDR2 domain comprising the amino acid sequence set forth in SEQ ID NO: 17, and a CDR1 domain comprising the amino acid sequence set forth in SEQ ID NO: 16; or
  (iii) a heavy chain variable region comprising a CDR3 domain comprising the amino acid sequence set forth in SEQ ID NO: 21, a CDR2 domain comprising the amino acid sequence set forth in SEQ ID NO: 20, and a CDR1 domain comprising the amino acid sequence set forth in SEQ ID NO: 19, and a light chain variable region comprising a CDR3 domain comprising the amino acid sequence set forth in SEQ ID NO: 24, a CDR2 domain comprising the amino acid sequence set forth in SEQ ID NO: 23, and a CDR1 domain comprising the amino acid sequence set forth in SEQ ID NO: 22.

9. The method of claim 8, wherein the range of detection for P2 is 62.5 pg/mL to 1500 pg/mL and the range of detection for P4 is 563 pg/mL to 27000 pg/mL.

10. The method of claim 8, wherein a P2 internal standard (P2_IS) and/or a P4 internal standard (P4_IS) is also detected.

11. The method of claim 10, wherein the MRM comprises monitoring one or more mass transitions m/z selected from the group consisting of: 441.7 $(M+2H)^{2+} \rightarrow 584.5$ $(y_5^{1+})$ for P2; 535 $(M+3H)^{3+} \rightarrow 832.4$ $(y_8^{1+})$ for P4, 445.5 $(M+2H)^{2+} \rightarrow 592.1$ $(y_5^{1+})$ for the P2 internal standard (P2_IS), and 538.4 $(M+3H)^{3+} \rightarrow 842.5$ $(y_8^{1+})$ for the P4 internal standard P4_IS.

* * * * *

SEQUENCE LISTING

```
<160> NUMBER OF SEQ ID NOS: 42

<210> SEQ ID NO 1
<211> LENGTH: 120
<212> TYPE: PRT
<213> ORGANISM: Artificial Sequence
<220> FEATURE:
<223> OTHER INFORMATION: Synthetic: 2C12 variable heavy (VH) domain

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45
```

```
Gly Val Ile Trp Arg Gly Ser Thr Asp Tyr Asn Ala Ala Phe Met
 50                  55                  60

Ser Arg Leu Ser Ile Thr Lys Asp Asn Ser Lys Ser Gln Val Phe Phe
 65                  70                  75                  80

Lys Met Asn Ser Leu Gln Ala Asp Asp Thr Ala Ile Tyr Phe Cys Ala
                 85                  90                  95

Leu Arg Gly Asn Tyr Val His Tyr Tyr Leu Met Asp Tyr Trp Gly Gln
                100                 105                 110

Gly Thr Ser Val Thr Val Ser Ser
                115                 120

<210> SEQ ID NO 2
<211> LENGTH: 107
<212> TYPE: PRT
<213> ORGANISM: Artificial Sequence
<220> FEATURE:
<223> OTHER INFORMATION: Synthetic: 2C12 variable light (VL) domain

<400> SEQUENCE: 2

Asp Ile Gln Val Thr Gln Thr Pro Ser Ser Leu Ser Ala Ser Leu Gly
  1               5                  10                  15

Asp Arg Val Thr Ile Ser Cys Arg Ala Ser Gln Asp Ile Ser Asn Tyr
                 20                  25                  30

Leu Asn Trp Tyr Gln Gln Lys Pro Asp Gly Thr Val Lys Leu Leu Ile
                 35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Asp Gln
 65                  70                  75                  80

Glu Asp Ile Ala Thr Tyr Phe Cys Gln Gln Gly Asn Thr Leu Pro Pro
                 85                  90                  95

Thr Phe Gly Gly Gly Thr Asn Leu Glu Ile Lys
                100                 105

<210> SEQ ID NO 3
<211> LENGTH: 116
<212> TYPE: PRT
<213> ORGANISM: Artificial Sequence
<220> FEATURE:
<223> OTHER INFORMATION: Synthetic: 3F4 variable heavy (VH) domain

<400> SEQUENCE: 3

Glu Val Gln Leu Gln Glu Ser Gly Pro Gly Leu Ala Lys Pro Ser Gln
  1               5                  10                  15

Thr Leu Ser Leu Thr Cys Ser Val Thr Gly Tyr Ser Ile Thr Ser Asn
                 20                  25                  30

Tyr Trp Asn Trp Ile Arg Lys Phe Pro Gly Asn Lys Leu Glu Tyr Met
                 35                  40                  45

Gly Tyr Ile Ser Phe Ser Gly Ser Thr Tyr Tyr Asn Pro Ser Leu Lys
 50                  55                  60

Ser Arg Ile Ser Ile Thr Arg Asp Thr Ser Lys Asn Gln Tyr Tyr Leu
 65                  70                  75                  80

Gln Leu Asn Ser Val Thr Thr Glu Asp Thr Ala Thr Tyr Tyr Cys Ala
                 85                  90                  95

Arg Trp Asn Tyr Tyr Ala Met Asp Tyr Trp Gly Gln Gly Thr Ser Val
                100                 105                 110

Thr Val Ser Ser
```

115

<210> SEQ ID NO 4
<211> LENGTH: 107
<212> TYPE: PRT
<213> ORGANISM: Artificial Sequence
<220> FEATURE:
<223> OTHER INFORMATION: Synthetic: 3F4 variable light (VL) domain

<400> SEQUENCE: 4

```
Asp Phe Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Phe Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Ser Trp Pro Tyr
                85                  90                  95

Thr Phe Gly Gly Gly Thr Lys Leu Glu Ile Lys
            100                 105
```

<210> SEQ ID NO 5
<211> LENGTH: 112
<212> TYPE: PRT
<213> ORGANISM: Artificial Sequence
<220> FEATURE:
<223> OTHER INFORMATION: Synthetic: 6E3 variable heavy (VH) domain

<400> SEQUENCE: 5

```
Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Val Lys Gln Arg Pro Gly His Gly Leu Glu Trp Ile
        35                  40                  45

Gly Glu Ile Leu Pro Gly Asn Gly Ser Thr Asn Cys Asn Glu Lys Phe
    50                  55                  60

Lys Gly Lys Ala Thr Phe Thr Ala Thr Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Thr Thr Val Ser Tyr Trp Gly Gln Gly Thr Thr Leu Thr Val Ser Ser
            100                 105                 110
```

<210> SEQ ID NO 6
<211> LENGTH: 112
<212> TYPE: PRT
<213> ORGANISM: Artificial Sequence
<220> FEATURE:
<223> OTHER INFORMATION: Synthetic: 6E3 variable light (VL) domain

<400> SEQUENCE: 6

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30
```

```
Asn Gly Asn Thr Tyr Leu His Trp Tyr Leu Gln Lys Pro Gly Gln Ser
            35                  40                  45

Pro Asn Leu Leu Ile Tyr Lys Val Ser Asn Arg Phe Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
             100                 105                 110

<210> SEQ ID NO 7
<211> LENGTH: 8
<212> TYPE: PRT
<213> ORGANISM: Artificial Sequence
<220> FEATURE:
<223> OTHER INFORMATION: Synthetic: 2C12 VH CDR1

<400> SEQUENCE: 7

Gly Phe Ser Leu Thr Asn Tyr Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic: 2C12 VH CDR2

<400> SEQUENCE: 8

Ile Trp Arg Gly Gly Ser Thr
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic: 2C12 VH CDR3

<400> SEQUENCE: 9

Ala Leu Arg Gly Asn Tyr Val His Tyr Tyr Leu Met Asp Tyr
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Synthetic: 2C12 VL CDR1

<400> SEQUENCE: 10

Gln Asp Ile Ser Asn Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic: 2C12 VL CDR2

<400> SEQUENCE: 11

Tyr Thr Ser
```

-continued

```
<210> SEQ ID NO 12
<211> LENGTH: 9
<212> TYPE: PRT
<213> ORGANISM: Artificial Sequence
<220> FEATURE:
<223> OTHER INFORMATION: Synthetic: 2C12 VL CDR3

<400> SEQUENCE: 12

Gln Gln Gly Asn Thr Leu Pro Pro Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic: 3F4 VH CDR1

<400> SEQUENCE: 13

Gly Tyr Ser Ile Thr Ser Asn Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic: 3F4 VH CDR2

<400> SEQUENCE: 14

Ile Ser Phe Ser Gly Ser Thr
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic: 3F4 VH CDR3

<400> SEQUENCE: 15

Ala Arg Trp Asn Tyr Tyr Ala Met Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Synthetic: 3F4 VL CDR1

<400> SEQUENCE: 16

Gln Ser Ile Gly Thr Asn
1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic: 3F4 VL CDR2

<400> SEQUENCE: 17

Phe Ala Ser
1
```

<210> SEQ ID NO 18
<211> LENGTH: 9
<212> TYPE: PRT
<213> ORGANISM: Artificial Sequence
<220> FEATURE:
<223> OTHER INFORMATION: Synthetic: 3F4 VL CDR3

<400> SEQUENCE: 18

Gln Gln Ser Asn Ser Trp Pro Tyr Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic: 6E3 VH CDR1

<400> SEQUENCE: 19

Gly Tyr Thr Phe Thr Gly Tyr Trp
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic: 6E3 VH CDR2

<400> SEQUENCE: 20

Ile Leu Pro Gly Asn Gly Ser Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic: 6E3 VH CDR3

<400> SEQUENCE: 21

Thr Thr Val Ser Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic: 6E3 VL CDR1

<400> SEQUENCE: 22

Gln Ser Leu Val His Ser Asn Gly Asn Thr Tyr
1               5                   10

<210> SEQ ID NO 23
<211> LENGTH: 3
<212> TYPE: PRT
<213> ORGANISM: Artificial Sequence
<220> FEATURE:
<223> OTHER INFORMATION: Synthetic: 6E3 VL CDR2

<400> SEQUENCE: 23

Lys Val Ser
1

<210> SEQ ID NO 24
<211> LENGTH: 9
<212> TYPE: PRT
<213> ORGANISM: Artificial Sequence
<220> FEATURE:
<223> OTHER INFORMATION: Synthetic: 6E3 VL CDR3

<400> SEQUENCE: 24

Ser Gln Ser Thr His Val Pro Phe Thr
1               5

<210> SEQ ID NO 25
<211> LENGTH: 152
<212> TYPE: PRT
<213> ORGANISM: Artificial Sequence
<220> FEATURE:
<223> OTHER INFORMATION: Synthetic: 2C12 hybridoma clone heavy chain
      consensus

<400> SEQUENCE: 25

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Arg Gly Gly Ser Thr Asp Tyr Asn Ala
65                  70                  75                  80

Ala Phe Met Ser Arg Leu Ser Ile Thr Lys Asp Asn Ser Lys Ser Gln
                85                  90                  95

Val Phe Phe Lys Met Asn Ser Leu Gln Ala Asp Asp Thr Ala Ile Tyr
            100                 105                 110

Phe Cys Ala Leu Arg Gly Asn Tyr Val His Tyr Tyr Leu Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro
145                 150

<210> SEQ ID NO 26
<211> LENGTH: 162
<212> TYPE: PRT
<213> ORGANISM: Artificial Sequence
<220> FEATURE:
<223> OTHER INFORMATION: Synthetic: 2C12 hybridoma clone light chain
      consensus

<400> SEQUENCE: 26

Met Val Ser Thr Ala Gln Phe Leu Gly Leu Leu Leu Leu Cys Phe Gln
1               5                   10                  15

Gly Thr Arg Cys Asp Ile Gln Val Thr Gln Thr Pro Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

```
Arg Phe Ser Gly Ser Gly Ser Gly Thr Asp Tyr Ser Leu Thr Ile Ser
                85                  90                  95

Asn Leu Asp Gln Glu Asp Ile Ala Thr Tyr Phe Cys Gln Gln Gly Asn
            100                 105                 110

Thr Leu Pro Pro Thr Phe Gly Gly Gly Thr Asn Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys

<210> SEQ ID NO 27
<211> LENGTH: 146
<212> TYPE: PRT
<213> ORGANISM: Artificial Sequence
<220> FEATURE:
<223> OTHER INFORMATION: Synthetic: 3F4 hybridoma clone heavy chain
      consensus

<400> SEQUENCE: 27

Met Met Val Leu Ser Leu Leu Tyr Leu Leu Thr Ala Leu Pro Gly Ile
1               5                   10                  15

Leu Ser Glu Val Gln Leu Gln Glu Ser Gly Pro Gly Leu Ala Lys Pro
            20                  25                  30

Ser Gln Thr Leu Ser Leu Thr Cys Ser Val Thr Gly Tyr Ser Ile Thr
        35                  40                  45

Ser Asn Tyr Trp Asn Trp Ile Arg Lys Phe Pro Gly Asn Lys Leu Glu
    50                  55                  60

Tyr Met Gly Tyr Ile Ser Phe Ser Gly Ser Thr Tyr Tyr Asn Pro Ser
65                  70                  75                  80

Leu Lys Ser Arg Ile Ser Ile Thr Arg Asp Thr Ser Lys Asn Gln Tyr
                85                  90                  95

Tyr Leu Gln Leu Asn Ser Val Thr Thr Glu Asp Thr Ala Thr Tyr Tyr
            100                 105                 110

Cys Ala Arg Trp Asn Tyr Tyr Ala Met Asp Tyr Trp Gly Gln Gly Thr
        115                 120                 125

Ser Val Thr Val Ser Ser Ala Lys Thr Thr Pro Pro Ser Val Phe Pro
    130                 135                 140

Leu Ala
145

<210> SEQ ID NO 28
<211> LENGTH: 162
<212> TYPE: PRT
<213> ORGANISM: Artificial Sequence
<220> FEATURE:
<223> OTHER INFORMATION: Synthetic: 3F4 hybridoma clone light chain
      consensus

<400> SEQUENCE: 28

Met Val Ser Thr Ala Gln Phe Leu Val Phe Leu Leu Phe Trp Ile Pro
1               5                   10                  15

Ala Ser Arg Gly Asp Phe Leu Leu Thr Gln Ser Pro Ala Ile Leu Ser
            20                  25                  30

Val Ser Pro Gly Glu Arg Val Ser Phe Ser Cys Arg Ala Ser Gln Ser
        35                  40                  45
```

```
Ile Gly Thr Asn Ile His Trp Tyr Gln Gln Arg Thr Asn Gly Ser Pro
    50                  55                  60

Arg Leu Leu Ile Lys Phe Ala Ser Glu Ser Ile Ser Gly Ile Pro Ser
 65                  70                  75                  80

Arg Phe Ser Gly Ser Gly Ser Gly Thr Asp Phe Thr Leu Thr Ile Asn
                 85                  90                  95

Ser Val Glu Ser Glu Asp Ile Ala Asp Tyr Tyr Cys Gln Gln Ser Asn
            100                 105                 110

Ser Trp Pro Tyr Thr Phe Gly Gly Thr Lys Leu Glu Ile Lys Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Arg

<210> SEQ ID NO 29
<211> LENGTH: 143
<212> TYPE: PRT
<213> ORGANISM: Artificial Sequence
<220> FEATURE:
<223> OTHER INFORMATION: Synthetic: 6E3 hybridoma clone heavy chain
      consensus

<400> SEQUENCE: 29

Met Gly Trp Ser Trp Val Met Leu Phe Leu Leu Ser Val Thr Ala Gly
 1               5                  10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Thr Gly Tyr Thr Phe
        35                  40                  45

Thr Gly Tyr Trp Ile Glu Trp Val Lys Gln Arg Pro Gly His Gly Leu
    50                  55                  60

Glu Trp Ile Gly Glu Ile Leu Pro Gly Asn Gly Ser Thr Asn Cys Asn
 65                  70                  75                  80

Glu Lys Phe Lys Gly Lys Ala Thr Phe Thr Ala Thr Ser Ser Asn
                 85                  90                  95

Thr Ala Tyr Met Gln Leu Ser Ser Leu Thr Thr Glu Asp Ser Ala Ile
            100                 105                 110

Tyr Tyr Cys Thr Thr Val Ser Tyr Trp Gly Gln Gly Thr Thr Leu Thr
            115                 120                 125

Val Ser Ser Ala Lys Thr Thr Pro Pro Ser Val Phe Pro Leu Ala
            130                 135                 140

<210> SEQ ID NO 30
<211> LENGTH: 166
<212> TYPE: PRT
<213> ORGANISM: Artificial Sequence
<220> FEATURE:
<223> OTHER INFORMATION: Synthetic: 6E3 hybridoma clone light chain
      consensus

<400> SEQUENCE: 30

Met Lys Leu Pro Val Arg Leu Leu Val Leu Met Phe Trp Ile Pro Ala
 1               5                  10                  15

Ser Thr Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
```

```
                35                  40                  45
Val His Ser Asn Gly Asn Thr Tyr Leu His Trp Tyr Leu Gln Lys Pro
         50                  55                  60
Gly Gln Ser Pro Asn Leu Leu Ile Tyr Lys Val Ser Asn Arg Phe Ser
 65                  70                  75                  80
Gly Val Pro Asp Arg Phe Thr Gly Ser Gly Ser Gly Thr Asp Phe Thr
                 85                  90                  95
Leu Lys Ile Ser Arg Val Glu Ala Glu Asp Leu Gly Val Tyr Phe Cys
            100                 105                 110
Ser Gln Ser Thr His Val Pro Phe Thr Phe Gly Ser Gly Thr Lys Leu
        115                 120                 125
Glu Ile Lys Arg Ala Asp Ala Ala Pro Thr Val Ser Ile Phe Pro Pro
    130                 135                 140
Ser Ser Glu Gln Leu Thr Ser Gly Gly Ala Ser Val Val Cys Phe Leu
145                 150                 155                 160
Asn Asn Phe Tyr Pro Lys
            165

<210> SEQ ID NO 31
<211> LENGTH: 8533
<212> TYPE: DNA
<213> ORGANISM: Homo sapiens
<220> FEATURE:
<221> NAME/KEY: misc_feature
<222> LOCATION: (1)..(8533)
<223> OTHER INFORMATION: Filamin A, isoform 1

<400> SEQUENCE: 31
attcgcgtgg aggcgcgtcg cgcgcagcgg acgccgacag aatccccgag gcgcctggcg      60
cgggcgcggg cgcgaaggcg atccgggcgc caccccgcgg tcatcggtca ccggtcgctc     120
tcaggaacag cagcgcaacc tctgctccct gcctcgcctc ccgcgcgcct aggtgcctgc     180
gactttaatt aaagggccgt ccctcgccg aggctgcagc accgccccc cggcttctcg       240 cgcctcaaaa tgagtagctc ccactctcgg gcgggccaga gcgcagcagg gcgcggctccg    300 ggcggcggcg tcgacacgcg ggacgccgag atgccggcca ccgagaagga cctggcggag     360
gacgcgccgt ggaagaagat ccagcagaac actttcacgc gctggtgcaa cgagcacctg     420
aagtgcgtga gcaagcgcat cgccaacctg cagacggacc tgagcgacgg gctgcggctt     480
atcgcgctgt tggaggtgct cagccagaag aagatgcacc gcaagcacaa ccagcggccc     540
actttccgcc aaatgcagct tgagaacgtg tcggtggcgc tcgagttcct ggaccgcgag     600
agcatcaaac tggtgtccat cgacagcaag gccatcgtgg acgggaacct gaagctgatc     660
ctgggcctca tctggaccct gatcctgcac tactccatct ccatgcccat gtgggacgag     720
gaggaggatg aggaggccaa gaagcagacc cccaagcaga ggctcctggg ctggatccag     780
aacaagctgc cgcagctgcc catcaccaac ttcagccggg actggcagag cggccgggcc     840
ctgggcgccc tggtggacag ctgtgccccg ggcctgtgtc ctgactggga ctcttggac     900 gccagcaagc ccgttaccaa tgcgcgagag gccatgcagc aggcggatga ctggctgggc     960
atccccaggg tgatcacccc cgaggagatt gtgaccccca acgtgacga gcactctgtc    1020 atgacctacc tgtcccagtt ccccaaggcc aagctgaagc caggggctcc cttgcggccc    1080
aaactgaacc cgaagaaagc ccgtgcctac gggccaggca tcgagcccac aggcaacatg    1140
gtgaagaagg ggcagagtt cactgtggag accagaagtg ctggccaggg agaggtgctg    1200
gtgtacgtgg aggacccggc cggacaccag gaggaggcaa aagtgaccgc caataacgac    1260
```

```
aagaaccgca ccttctccgt ctggtacgtc cccgaggtga cggggactca taaggttact    1320
gtgctctttg ctggccagca catcgccaag agcccttcg aggtgtacgt ggataagtca    1380
cagggtgacg ccagcaaagt gacagcccaa ggtcccggcc tggagcccag tggcaacatc    1440
gccaacaaga ccacctactt tgagatcttt acggcaggag ctggcacggg cgaggtcgag    1500
gttgtgatcc aggaccccat gggacagaag ggcacggtag agcctcagct ggaggcccgg    1560
ggcgacagca cataccgctg cagctaccag cccaccatgg agggcgtcca caccgtgcac    1620
gtcacgtttg ccggcgtgcc catccctcgc agcccctaca ctgtcactgt tggccaagcc    1680
tgtaacccga gtgcctgccg ggcggttggc cggggcctcc agcccaaggg tgtgcgggtg    1740
aaggagacag ctgacttcaa ggtgtacaca aagggcgctg gcagtgggga gctgaaggtc    1800
accgtgaagg gccccaaggg agaggagcgc gtgaagcaga aggacctggg ggatggcgtg    1860
tatggcttcg agtattaccc catggtccct ggaacctata tcgtcaccat cacgtggggt    1920
ggtcagaaca tcgggcgcag tcccttcgaa gtgaaggtgg gcaccgagtg tggcaatcag    1980
aaggtacggg cctggggccc tgggctggag ggcggcgtcg ttggcaagtc agcagacttt    2040
gtggtggagg ctatcgggga cgacgtggc acgctgggct tctcggtgga agggccatcg    2100
caggctaaga tcgaatgtga cgacaagggc gacggctcct gtgatgtgcg ctactggccg    2160
caggaggctg gcgagtatgc cgttcacgtg ctgtgcaaca gcgaagacat ccgcctcagc    2220
cccttcatgg ctgacatccg tgacgcgccc caggacttcc acccagacag ggtgaaggca    2280
cgtgggcctg gattggagaa gacaggtgtg gccgtcaaca gccagcaga gttcacagtg    2340 gatgccaagc acggtggcaa ggccccactt cgggtccaag tccaggacaa tgaaggctgc    2400
cctgtggagg cgttggtcaa ggacaacggc aatggcactt acagctgctc ctacgtgccc    2460
aggaagccgg tgaagcacac agccatggtg tcctggggag gcgtcagcat ccccaacagc    2520
cccttcaggg tgaatgtggg agctggcagc caccccaaca aggtcaaagt atacggcccc    2580
ggagtagcca agacagggct caaggcccac gagcccacct acttcactgt ggactgcgcc    2640
gaggctggcc aggggacgt cagcatcggc atcaagtgtg ccctggagt ggtaggcccc    2700 gccgaagctg acatcgactt cgacatcatc cgcaatgaca atgacaccatt cacggtcaag    2760 tacacgcccc ggggggctgg cagctacacc attatggtcc tctttgctga ccaggccacg    2820
cccaccagcc ccatccgagt caaggtggag ccctctcatg acgccagtaa ggtgaaggcc    2880
gagggccctg gcctcagtcg cactggtgtc gagcttggca agcccaccca cttcacagta    2940
aatgccaaag ctgctggcaa aggcaagctg gacgtccagt tctcaggact caccaagggg    3000
gatgcagtgc gagatgtgga catcatcgac accatgaca acacctacac agtcaagtac    3060
acgcctgtcc agcagggtcc agtaggcgtc aatgtcactt atggagggga tcccatccct    3120
aagagccctt tctcagtggc agtatctcca agcctggacc tcagcaagat caaggtgtct    3180
ggcctgggag agaaggtgga cgttggcaaa gaccaggagt tcacagtcaa atcaaagggt    3240
gctggtggtc aaggcaaagt ggcatccaag attgtgggcc cctcgggtgc agcggtgccc    3300
tgcaaggtgg agccaggcct gggggctgac aacagtgtgg tgcgcttcct gccccgtgag    3360
gaagggccct atgaggtgga ggtgacctat gacggcgtgc ccgtgcctgg cagccccttt    3420
cctctggaag ctgtggcccc caccaagcct agcaaggtga aggcgtttgg gccggggctg    3480
cagggaggca gtgcgggctc cccgccgcgc ttcaccatcg acaccaaggg cgccggcaca    3540
ggtggcctgg gcctgacggt ggagggcccc tgtgaggcgc agctcgagtg cttggacaat    3600
```

```
ggggatggca catgttccgt gtcctacgtg cccaccgagc ccggggacta caacatcaac    3660
atcctcttcg ctgacaccca catccctggc tccccattca aggcccacgt ggttccctgc    3720
tttgacgcat ccaaagtcaa gtgctcaggc cccgggctgg agcgggccac cgctggggag    3780
gtgggccaat ccaagtggac tgctcgagcg cgggcagcg cggagctgac cattgagatc    3840
tgctcggagg cggggcttcc ggccgaggtg tacatccagg accacggtga tggcacgcac    3900
accattacct acattcccct ctgcccggg gcctacaccg tcaccatcaa gtacggcggc    3960
cagcccgtgc ccaacttccc cagcaagctg caggtggaac ctgcggtgga cacttccggt    4020
gtccagtgct atgggcctgg tattgagggc cagggtgtct tccgtgaggc caccactgag    4080
ttcagtgtgg acgcccgggc tctgacacag accggagggc cgcacgtcaa ggcccgtgtg    4140 gccaaccccct caggcaacct gacggagacc tacgttcagg accgtggcga tggcatgtac    4200
aaagtggagt acacgcctta cgaggaggga ctgcactccg tggacgtgac ctatgacggc    4260
agtcccgtgc ccagcagccc cttccaggtg cccgtgaccg agggctgcga cccctcccgg    4320
gtgcgtgtcc acgggccagg catccaaagt ggcaccacca caagcccaa caagttcact    4380 gtggagacca ggggagctgg cacgggcggc ctgggcctgg ctgtagaggg ccctccgag     4440 gccaagatgt cctgcatgga taacaaggac ggcagctgct cggtcgagta catcccttat    4500
gaggctggca cctacagcct caacgtcacc tatggtggcc atcaagtgcc aggcagtcct    4560
ttcaaggtcc ctgtgcatga tgtgacagat gcgtccaagg tcaagtgctc tgggcccggc    4620
ctgagcccag gcatggttcg tgccaacctc cctcagtcct tccaggtgga cacaagcaag    4680
gctggtgtgc cccattgca ggtcaaagtg caagggccca aaggcctggt ggagccagtg     4740
gacgtggtag acaacgctga tggcacccag accgtcaatt atgtgcccag ccgagaaggg    4800
ccctacagca tctcagtact gtatggagat gaagaggtac cccggagccc cttcaaggtc    4860
aaggtgctgc ctactcatga tgccagcaag gtgaaggcca gtggccccgg gctcaacacc    4920 actgcgtgc ctgccagcct gcccgtggag ttcaccatcg atgcaaagga cgccggggag    4980
ggcctgctgg ctgtccagat cacggatccc gaaggcaagc cgaagaagac acacatccaa    5040
gacaaccatg acggcacgta tacagtggcc tacgtgccag acgtgacagg tcgctacacc    5100
atcctcatca agtacggtgg tgacgagatc cccttctccc cgtaccgcgt gcgtgccgtg    5160
cccaccgggg acgccagcaa gtgcactgtc acaggtgctg gcatcggccc caccattcag    5220
attggggagg agacggtgat cactgtggac actaaggcgg caggcaaagg caaagtgacg    5280
tgcaccgtgt gcacgcctga tggctcagag gtggatgtgg acgtggtgga gaatgaggac    5340
ggcactttcg acatcttcta cacggccccc cagccgggca atacgtcat ctgtgtgcgc    5400 tttggtggcg agcacgtgcc caacagcccc ttccaagtga cggctctggc tgggaccag    5460 ccctcggtgc agccccctct acggtctcag cagctggccc cacagtacac ctacgcccag    5520
ggcggccagc agacttgggc cccggagagg cccctggtgg tgtcaatgg ctgatgatgtg   5580 accagcctga ggccctttga ccttgtcatc cccttcacca tcaagaaggg cgagatcaca    5640
ggggaggttc ggatgccctc aggcaaggtg gcgcagccca ccatcactga caacaaagac    5700
ggcaccgtga ccgtgcggta tgcacccagc gaggctggcc tgcacgagat ggacatccgc    5760
tatgacaaca tgcacatccc aggaagcccc ttgcagttct atgtggatta cgtcaactgt    5820
ggccatgtca ctgcctatgg gcctggcctc acccatggag tagtgaacaa gcctgccacc    5880
ttcaccgtca acaccaagga tgcaggagag ggggcctgt ctctggccat tgagggcccg    5940
tccaaagcag aaatcagctg cactgacaac caggatggga catgcagcgt gtcctacctg    6000
```

```
cctgtgctgc cgggggacta cagcattcta gtcaagtaca atgaacagca cgtcccaggc    6060
agccccttca ctgctcgggt cacaggtgac gactccatgc gtatgtccca cctaaaggtc    6120
ggctctgctg ccgacatccc catcaacatc tcagagacgg atctcagcct gctgacggcc    6180
actgtggtcc cgccctcggg ccgggaggag ccctgtttgc tgaagcggct gcgtaatggc    6240
cacgtgggga tttcattcgt gcccaaggag acggggagc acctggtgca tgtgaagaaa     6300
aatggccagc acgtggccag cagccccatc ccggtggtga tcagccagtc ggaaattggg    6360
gatgccagtc gtgttcgggt ctctggtcag ggccttcacg aaggccacac ctttgagcct    6420
gcagagttta tcattgatac ccgcgatgca ggctatggtg ggctcagcct gtccattgag    6480
ggccccagca aggtggacat caacacagag gacctggagg acgggacgtg cagggtcacc    6540
tactgcccca cagagccagg caactacatc atcaacatca gtttgccga ccagcacgtg     6600 cctggcagcc ccttctctgt gaaggtgaca ggcgagggcc gggtgaaaga gagcatcacc    6660
cgcaggcgtc gggctccttc agtgccaac gttggtagtc attgtgacct cagcctgaaa     6720
atccctgaaa ttagcatcca ggatatgaca gcccaggtga ccagcccatc gggcaagacc    6780
catgaggccg agatcgtgga aggggagaac cacacctact gcatccgctt tgttcccgct    6840
gagatgggca cacacacagt cagcgtgaag tacaagggcc agcacgtgcc tgggagcccc    6900
ttccagttca ccgtgggggcc cctaggggaa ggggagccc acaaggtccg agctgggggc    6960
cctggcctgg agagagctga agctggagtg ccagccgaat tcagtatctg gacccgggaa    7020
gctggtgctg gaggcctggc cattgctgtc gagggcccca gcaaggctga gatctctttt    7080
gaggaccgca aggacggctc ctgtggtgtg gcttatgtgg tccaggagcc aggtgactac    7140
gaagtctcag tcaagttcaa cgaggaacac attcccgaca gcccttcgt ggtgcctgtg     7200 gcttctccgt ctggcgacgc ccgccgcctc actgtttcta gccttcagga gtcagggcta    7260
aaggtcaacc agccagcctc ttttgcagtc agcctgaacg gggccaaggg ggcgatcgat    7320
gccaaggtgc acagcccctc aggagccctg gaggagtgct atgtcacaga aattgaccaa    7380
gataagtatg ctgtgcgctt catccctcgg gagaatggcg tttacctgat tgacgtcaag    7440
ttcaacggca cccacatccc tggaagcccc ttcaagatcc gagttgggga gcctgggcat    7500
ggaggggacc caggcttggt gtctgcttac ggagcaggtc tggaaggcgg tgtcacaggg    7560
aacccagctg agttcgtcgt gaacacgagc aatgcgggag ctggtgccct gtcggtgacc    7620
attgacggcc cctccaaggt gaagatggat tgccaggagt gccctgaggg ctaccgcgtc    7680
acctataccc ccatggcacc tggcagctac ctcatctcca tcaagtacgg cggccctac     7740 cacattgggg gcagcccctt caaggccaaa gtcacaggcc ccgtctcgt cagcaaccac     7800 agcctccacg agacatcatc agtgtttgta gactctctga ccaaggccac ctgtgccccc    7860
cagcatgggg ccccgggtcc tgggcctgct gacgccagca aggtggtggc caagggcctg    7920
gggctgagca aggcctacgt aggccagaag agcagcttca cagtagactg cagcaaagca    7980
ggcaacaaca tgctgctggt gggggttcat ggcccaagga cccctgcga ggagatcctg      8040 gtgaagcacg tgggcagccg gctctacagc gtgtcctacc tgctcaagga caaggggag     8100 tacacactgg tggtcaaatg gggggacgag cacatcccag gcagcccta ccgcgttgtg     8160 gtgcctgag tctgggggcc gtgccagccg gcagccccca agcctgcccc gctacccaag     8220 cagcccgcc ctcttcccct caaccccggc ccaggccgcc ctggccgccc gcctgtcact     8280
gcagccgccc ctgccctgtg ccgtgctgcg ctcacctgcc tccccagcca gccgctgacc    8340
```

```
tctcggctttt cacttgggca gagggagcca tttggtggcg ctgcttgtct tctttggttc    8400
tgggaggggt gagggatggg ggtcctgtac acaaccaccc actagttctc ttctccagcc    8460
aagaggaata aagttttgct tccattaaaa aaaaaaaaaa aaaaaaaaaa aaaaaaaaaa    8520
aaaaaaaaaa aaa                                                       8533

<210> SEQ ID NO 32
<211> LENGTH: 2639
<212> TYPE: PRT
<213> ORGANISM: Homo sapiens
<220> FEATURE:
<221> NAME/KEY: misc_feature
<222> LOCATION: (1)..(2639)
<223> OTHER INFORMATION: Filamin A, isoform 1

<400> SEQUENCE: 32

Met Ser Ser Ser His Ser Arg Ala Gly Gln Ser Ala Ala Gly Ala Ala
1               5                   10                  15

Pro Gly Gly Gly Val Asp Thr Arg Asp Ala Glu Met Pro Ala Thr Glu
            20                  25                  30

Lys Asp Leu Ala Glu Asp Ala Pro Trp Lys Lys Ile Gln Gln Asn Thr
        35                  40                  45

Phe Thr Arg Trp Cys Asn Glu His Leu Lys Cys Val Ser Lys Arg Ile
    50                  55                  60

Ala Asn Leu Gln Thr Asp Leu Ser Asp Gly Leu Arg Leu Ile Ala Leu
65                  70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125

Ile Val Asp Gly Asn Leu Lys Leu Ile Leu Gly Leu Ile Trp Thr Leu
    130                 135                 140

Ile Leu His Tyr Ser Ile Ser Met Pro Met Trp Asp Glu Glu Glu Asp
145                 150                 155                 160

Glu Glu Ala Lys Lys Gln Thr Pro Lys Gln Arg Leu Leu Gly Trp Ile
                165                 170                 175

Gln Asn Lys Leu Pro Gln Leu Pro Ile Thr Asn Phe Ser Arg Asp Trp
            180                 185                 190

Gln Ser Gly Arg Ala Leu Gly Ala Leu Val Asp Ser Cys Ala Pro Gly
        195                 200                 205

Leu Cys Pro Asp Trp Asp Ser Trp Asp Ala Ser Lys Pro Val Thr Asn
    210                 215                 220

Ala Arg Glu Ala Met Gln Gln Ala Asp Asp Trp Leu Gly Ile Pro Gln
225                 230                 235                 240

Val Ile Thr Pro Glu Glu Ile Val Asp Pro Asn Val Asp Glu His Ser
                245                 250                 255

Val Met Thr Tyr Leu Ser Gln Phe Pro Lys Ala Lys Leu Lys Pro Gly
            260                 265                 270

Ala Pro Leu Arg Pro Lys Leu Asn Pro Lys Lys Ala Arg Ala Tyr Gly
        275                 280                 285

Pro Gly Ile Glu Pro Thr Gly Asn Met Val Lys Lys Arg Ala Glu Phe
    290                 295                 300

Thr Val Glu Thr Arg Ser Ala Gly Gln Gly Glu Val Leu Val Tyr Val
305                 310                 315                 320
```

```
Glu Asp Pro Ala Gly His Gln Glu Ala Lys Val Thr Ala Asn Asn
                325                 330                 335

Asp Lys Asn Arg Thr Phe Ser Val Trp Tyr Val Pro Glu Val Thr Gly
            340                 345                 350

Thr His Lys Val Thr Val Leu Phe Ala Gly Gln His Ile Ala Lys Ser
                355                 360                 365

Pro Phe Glu Val Tyr Val Asp Lys Ser Gln Gly Asp Ala Ser Lys Val
            370                 375                 380

Thr Ala Gln Gly Pro Gly Leu Glu Pro Ser Gly Asn Ile Ala Asn Lys
385                 390                 395                 400

Thr Thr Tyr Phe Glu Ile Phe Thr Ala Gly Ala Gly Thr Gly Glu Val
                405                 410                 415

Glu Val Val Ile Gln Asp Pro Met Gly Gln Lys Gly Thr Val Glu Pro
                420                 425                 430

Gln Leu Glu Ala Arg Gly Asp Ser Thr Tyr Arg Cys Ser Tyr Gln Pro
            435                 440                 445

Thr Met Glu Gly Val His Thr Val His Val Thr Phe Ala Gly Val Pro
            450                 455                 460

Ile Pro Arg Ser Pro Tyr Thr Val Thr Val Gly Gln Ala Cys Asn Pro
465                 470                 475                 480

Ser Ala Cys Arg Ala Val Gly Arg Gly Leu Gln Pro Lys Gly Val Arg
                485                 490                 495

Val Lys Glu Thr Ala Asp Phe Lys Val Tyr Thr Lys Gly Ala Gly Ser
            500                 505                 510

Gly Glu Leu Lys Val Thr Val Lys Gly Pro Lys Gly Glu Glu Arg Val
            515                 520                 525

Lys Gln Lys Asp Leu Gly Asp Gly Val Tyr Gly Phe Glu Tyr Tyr Pro
            530                 535                 540

Met Val Pro Gly Thr Tyr Ile Val Thr Ile Thr Trp Gly Gly Gln Asn
545                 550                 555                 560

Ile Gly Arg Ser Pro Phe Glu Val Lys Val Gly Thr Glu Cys Gly Asn
                565                 570                 575

Gln Lys Val Arg Ala Trp Gly Pro Gly Leu Glu Gly Gly Val Val Gly
            580                 585                 590

Lys Ser Ala Asp Phe Val Val Glu Ala Ile Gly Asp Asp Val Gly Thr
            595                 600                 605

Leu Gly Phe Ser Val Glu Gly Pro Ser Gln Ala Lys Ile Glu Cys Asp
            610                 615                 620

Asp Lys Gly Asp Gly Ser Cys Asp Val Arg Tyr Trp Pro Gln Glu Ala
625                 630                 635                 640

Gly Glu Tyr Ala Val His Val Leu Cys Asn Ser Glu Asp Ile Arg Leu
                645                 650                 655

Ser Pro Phe Met Ala Asp Ile Arg Asp Ala Pro Gln Asp Phe His Pro
            660                 665                 670

Asp Arg Val Lys Ala Arg Gly Pro Gly Leu Glu Lys Thr Gly Val Ala
            675                 680                 685

Val Asn Lys Pro Ala Glu Phe Thr Val Asp Ala Lys His Gly Gly Lys
            690                 695                 700

Ala Pro Leu Arg Val Gln Val Gln Asp Asn Glu Gly Cys Pro Val Glu
705                 710                 715                 720

Ala Leu Val Lys Asp Asn Gly Asn Gly Thr Tyr Ser Cys Ser Tyr Val
                725                 730                 735
```

```
Pro Arg Lys Pro Val Lys His Thr Ala Met Val Ser Trp Gly Gly Val
            740                 745                 750

Ser Ile Pro Asn Ser Pro Phe Arg Val Asn Val Gly Ala Gly Ser His
        755                 760                 765

Pro Asn Lys Val Lys Val Tyr Gly Pro Gly Val Ala Lys Thr Gly Leu
    770                 775                 780

Lys Ala His Glu Pro Thr Tyr Phe Thr Val Asp Cys Ala Glu Ala Gly
785                 790                 795                 800

Gln Gly Asp Val Ser Ile Gly Ile Lys Cys Ala Pro Gly Val Val Gly
                805                 810                 815

Pro Ala Glu Ala Asp Ile Asp Phe Asp Ile Ile Arg Asn Asp Asn Asp
            820                 825                 830

Thr Phe Thr Val Lys Tyr Thr Pro Arg Gly Ala Gly Ser Tyr Thr Ile
        835                 840                 845

Met Val Leu Phe Ala Asp Gln Ala Thr Pro Thr Ser Pro Ile Arg Val
    850                 855                 860

Lys Val Glu Pro Ser His Asp Ala Ser Lys Val Lys Ala Glu Gly Pro
865                 870                 875                 880

Gly Leu Ser Arg Thr Gly Val Glu Leu Gly Lys Pro Thr His Phe Thr
                885                 890                 895

Val Asn Ala Lys Ala Ala Gly Lys Gly Lys Leu Asp Val Gln Phe Ser
            900                 905                 910

Gly Leu Thr Lys Gly Asp Ala Val Arg Asp Val Asp Ile Asp His
        915                 920                 925

His Asp Asn Thr Tyr Thr Val Lys Tyr Thr Pro Val Gln Gln Gly Pro
    930                 935                 940

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
                965                 970                 975

Ser Gly Leu Gly Glu Lys Val Asp Val Gly Lys Asp Gln Glu Phe Thr
            980                 985                 990

Val Lys Ser Lys Gly Ala Gly Gly Gln Gly Lys Val Ala Ser Lys Ile
        995                 1000                1005

Val Gly Pro Ser Gly Ala Ala Val Pro Cys Lys Val Glu Pro Gly
    1010                1015                1020

Leu Gly Ala Asp Asn Ser Val Val Arg Phe Leu Pro Arg Glu Glu
    1025                1030                1035

Gly Pro Tyr Glu Val Glu Val Thr Tyr Asp Gly Val Pro Val Pro
    1040                1045                1050

Gly Ser Pro Phe Pro Leu Glu Ala Val Ala Pro Thr Lys Pro Ser
    1055                1060                1065

Lys Val Lys Ala Phe Gly Pro Gly Leu Gln Gly Ser Ala Gly
    1070                1075                1080

Ser Pro Ala Arg Phe Thr Ile Asp Thr Lys Gly Ala Gly Thr Gly
    1085                1090                1095

Gly Leu Gly Leu Thr Val Glu Gly Pro Cys Glu Ala Gln Leu Glu
    1100                1105                1110

Cys Leu Asp Asn Gly Asp Gly Thr Cys Ser Val Ser Tyr Val Pro
    1115                1120                1125

Thr Glu Pro Gly Asp Tyr Asn Ile Asn Ile Leu Phe Ala Asp Thr
    1130                1135                1140

His Ile Pro Gly Ser Pro Phe Lys Ala His Val Val Pro Cys Phe
```

```
            1145                1150                1155

Asp Ala Ser Lys Val Lys Cys Ser Gly Pro Gly Leu Glu Arg Ala
            1160                1165                1170

Thr Ala Gly Glu Val Gly Gln Phe Gln Val Asp Cys Ser Ser Ala
            1175                1180                1185

Gly Ser Ala Glu Leu Thr Ile Glu Ile Cys Ser Glu Ala Gly Leu
            1190                1195                1200

Pro Ala Glu Val Tyr Ile Gln Asp His Gly Asp Gly Thr His Thr
            1205                1210                1215

Ile Thr Tyr Ile Pro Leu Cys Pro Gly Ala Tyr Thr Val Thr Ile
            1220                1225                1230

Lys Tyr Gly Gly Gln Pro Val Pro Asn Phe Pro Ser Lys Leu Gln
            1235                1240                1245

Val Glu Pro Ala Val Asp Thr Ser Gly Val Gln Cys Tyr Gly Pro
            1250                1255                1260

Gly Ile Glu Gly Gln Gly Val Phe Arg Glu Ala Thr Thr Glu Phe
            1265                1270                1275

Ser Val Asp Ala Arg Ala Leu Thr Gln Thr Gly Gly Pro His Val
            1280                1285                1290

Lys Ala Arg Val Ala Asn Pro Ser Gly Asn Leu Thr Glu Thr Tyr
            1295                1300                1305

Val Gln Asp Arg Gly Asp Gly Met Tyr Lys Val Glu Tyr Thr Pro
            1310                1315                1320

Tyr Glu Glu Gly Leu His Ser Val Asp Val Thr Tyr Asp Gly Ser
            1325                1330                1335

Pro Val Pro Ser Ser Pro Phe Gln Val Pro Val Thr Glu Gly Cys
            1340                1345                1350

Asp Pro Ser Arg Val Arg Val His Gly Pro Gly Ile Gln Ser Gly
            1355                1360                1365

Thr Thr Asn Lys Pro Asn Lys Phe Thr Val Glu Thr Arg Gly Ala
            1370                1375                1380

Gly Thr Gly Gly Leu Gly Leu Ala Val Glu Gly Pro Ser Glu Ala
            1385                1390                1395

Lys Met Ser Cys Met Asp Asn Lys Asp Gly Ser Cys Ser Val Glu
            1400                1405                1410

Tyr Ile Pro Tyr Glu Ala Gly Thr Tyr Ser Leu Asn Val Thr Tyr
            1415                1420                1425

Gly Gly His Gln Val Pro Gly Ser Pro Phe Lys Val Pro Val His
            1430                1435                1440

Asp Val Thr Asp Ala Ser Lys Val Lys Cys Ser Gly Pro Gly Leu
            1445                1450                1455

Ser Pro Gly Met Val Arg Ala Asn Leu Pro Gln Ser Phe Gln Val
            1460                1465                1470

Asp Thr Ser Lys Ala Gly Val Ala Pro Leu Gln Val Lys Val Gln
            1475                1480                1485

Gly Pro Lys Gly Leu Val Glu Pro Val Asp Val Asp Asn Ala
            1490                1495                1500

Asp Gly Thr Gln Thr Val Asn Tyr Val Pro Ser Arg Glu Gly Pro
            1505                1510                1515

Tyr Ser Ile Ser Val Leu Tyr Gly Asp Glu Glu Val Pro Arg Ser
            1520                1525                1530

Pro Phe Lys Val Lys Val Leu Pro Thr His Asp Ala Ser Lys Val
            1535                1540                1545
```

```
Lys Ala Ser Gly Pro Gly Leu Asn Thr Thr Gly Val Pro Ala Ser
1550                1555                1560

Leu Pro Val Glu Phe Thr Ile Asp Ala Lys Asp Ala Gly Glu Gly
1565                1570                1575

Leu Leu Ala Val Gln Ile Thr Asp Pro Glu Gly Lys Pro Lys Lys
1580                1585                1590

Thr His Ile Gln Asp Asn His Asp Gly Thr Tyr Thr Val Ala Tyr
1595                1600                1605

Val Pro Asp Val Thr Gly Arg Tyr Thr Ile Leu Ile Lys Tyr Gly
1610                1615                1620

Gly Asp Glu Ile Pro Phe Ser Pro Tyr Arg Val Arg Ala Val Pro
1625                1630                1635

Thr Gly Asp Ala Ser Lys Cys Thr Val Thr Gly Ala Gly Ile Gly
1640                1645                1650

Pro Thr Ile Gln Ile Gly Glu Glu Thr Val Ile Thr Val Asp Thr
1655                1660                1665

Lys Ala Ala Gly Lys Gly Lys Val Thr Cys Thr Val Cys Thr Pro
1670                1675                1680

Asp Gly Ser Glu Val Asp Val Asp Val Val Glu Asn Glu Asp Gly
1685                1690                1695

Thr Phe Asp Ile Phe Tyr Thr Ala Pro Gln Pro Gly Lys Tyr Val
1700                1705                1710

Ile Cys Val Arg Phe Gly Gly Glu His Val Pro Asn Ser Pro Phe
1715                1720                1725

Gln Val Thr Ala Leu Ala Gly Asp Gln Pro Ser Val Gln Pro Pro
1730                1735                1740

Leu Arg Ser Gln Gln Leu Ala Pro Gln Tyr Thr Tyr Ala Gln Gly
1745                1750                1755

Gly Gln Gln Thr Trp Ala Pro Glu Arg Pro Leu Val Gly Val Asn
1760                1765                1770

Gly Leu Asp Val Thr Ser Leu Arg Pro Phe Asp Leu Val Ile Pro
1775                1780                1785

Phe Thr Ile Lys Lys Gly Glu Ile Thr Gly Glu Val Arg Met Pro
1790                1795                1800

Ser Gly Lys Val Ala Gln Pro Thr Ile Thr Asp Asn Lys Asp Gly
1805                1810                1815

Thr Val Thr Val Arg Tyr Ala Pro Ser Glu Ala Gly Leu His Glu
1820                1825                1830

Met Asp Ile Arg Tyr Asp Asn Met His Ile Pro Gly Ser Pro Leu
1835                1840                1845

Gln Phe Tyr Val Asp Tyr Val Asn Cys Gly His Val Thr Ala Tyr
1850                1855                1860

Gly Pro Gly Leu Thr His Gly Val Val Asn Lys Pro Ala Thr Phe
1865                1870                1875

Thr Val Asn Thr Lys Asp Ala Gly Glu Gly Gly Leu Ser Leu Ala
1880                1885                1890

Ile Glu Gly Pro Ser Lys Ala Glu Ile Ser Cys Thr Asp Asn Gln
1895                1900                1905

Asp Gly Thr Cys Ser Val Ser Tyr Leu Pro Val Leu Pro Gly Asp
1910                1915                1920

Tyr Ser Ile Leu Val Lys Tyr Asn Glu Gln His Val Pro Gly Ser
1925                1930                1935
```

-continued

Pro Phe Thr Ala Arg Val Thr Gly Asp Asp Ser Met Arg Met Ser
1940            1945                1950

His Leu Lys Val Gly Ser Ala Ala Asp Ile Pro Ile Asn Ile Ser
1955            1960                1965

Glu Thr Asp Leu Ser Leu Leu Thr Ala Thr Val Val Pro Pro Ser
1970            1975                1980

Gly Arg Glu Glu Pro Cys Leu Leu Lys Arg Leu Arg Asn Gly His
1985            1990                1995

Val Gly Ile Ser Phe Val Pro Lys Glu Thr Gly Glu His Leu Val
2000            2005                2010

His Val Lys Lys Asn Gly Gln His Val Ala Ser Ser Pro Ile Pro
2015            2020                2025

Val Val Ile Ser Gln Ser Glu Ile Gly Asp Ala Ser Arg Val Arg
2030            2035                2040

Val Ser Gly Gln Gly Leu His Glu Gly His Thr Phe Glu Pro Ala
2045            2050                2055

Glu Phe Ile Ile Asp Thr Arg Asp Ala Gly Tyr Gly Gly Leu Ser
2060            2065                2070

Leu Ser Ile Glu Gly Pro Ser Lys Val Asp Ile Asn Thr Glu Asp
2075            2080                2085

Leu Glu Asp Gly Thr Cys Arg Val Thr Tyr Cys Pro Thr Glu Pro
2090            2095                2100

Gly Asn Tyr Ile Ile Asn Ile Lys Phe Ala Asp Gln His Val Pro
2105            2110                2115

Gly Ser Pro Phe Ser Val Lys Val Thr Gly Glu Gly Arg Val Lys
2120            2125                2130

Glu Ser Ile Thr Arg Arg Arg Arg Ala Pro Ser Val Ala Asn Val
2135            2140                2145

Gly Ser His Cys Asp Leu Ser Leu Lys Ile Pro Glu Ile Ser Ile
2150            2155                2160

Gln Asp Met Thr Ala Gln Val Thr Ser Pro Ser Gly Lys Thr His
2165            2170                2175

Glu Ala Glu Ile Val Glu Gly Glu Asn His Thr Tyr Cys Ile Arg
2180            2185                2190

Phe Val Pro Ala Glu Met Gly Thr His Thr Val Ser Val Lys Tyr
2195            2200                2205

Lys Gly Gln His Val Pro Gly Ser Pro Phe Gln Phe Thr Val Gly
2210            2215                2220

Pro Leu Gly Glu Gly Gly Ala His Lys Val Arg Ala Gly Gly Pro
2225            2230                2235

Gly Leu Glu Arg Ala Glu Ala Gly Val Pro Ala Glu Phe Ser Ile
2240            2245                2250

Trp Thr Arg Glu Ala Gly Ala Gly Gly Leu Ala Ile Ala Val Glu
2255            2260                2265

Gly Pro Ser Lys Ala Glu Ile Ser Phe Glu Asp Arg Lys Asp Gly
2270            2275                2280

Ser Cys Gly Val Ala Tyr Val Gln Glu Pro Gly Asp Tyr Glu
2285            2290                2295

Val Ser Val Lys Phe Asn Glu Glu His Ile Pro Asp Ser Pro Phe
2300            2305                2310

Val Val Pro Val Ala Ser Pro Ser Gly Asp Ala Arg Arg Leu Thr
2315            2320                2325

Val Ser Ser Leu Gln Glu Ser Gly Leu Lys Val Asn Gln Pro Ala

```
            2330               2335                2340
Ser Phe Ala Val Ser Leu Asn Gly Ala Lys Gly Ala Ile Asp Ala
            2345               2350                2355

Lys Val His Ser Pro Ser Gly Ala Leu Glu Cys Tyr Val Thr
        2360               2365                2370

Glu Ile Asp Gln Asp Lys Tyr Ala Val Arg Phe Ile Pro Arg Glu
        2375               2380                2385

Asn Gly Val Tyr Leu Ile Asp Val Lys Phe Asn Gly Thr His Ile
        2390               2395                2400

Pro Gly Ser Pro Phe Lys Ile Arg Val Gly Glu Pro Gly His Gly
        2405               2410                2415

Gly Asp Pro Gly Leu Val Ser Ala Tyr Gly Ala Gly Leu Glu Gly
        2420               2425                2430

Gly Val Thr Gly Asn Pro Ala Glu Phe Val Val Asn Thr Ser Asn
        2435               2440                2445

Ala Gly Ala Gly Ala Leu Ser Val Thr Ile Asp Gly Pro Ser Lys
        2450               2455                2460

Val Lys Met Asp Cys Gln Glu Cys Pro Glu Gly Tyr Arg Val Thr
        2465               2470                2475

Tyr Thr Pro Met Ala Pro Gly Ser Tyr Leu Ile Ser Ile Lys Tyr
        2480               2485                2490

Gly Gly Pro Tyr His Ile Gly Gly Ser Pro Phe Lys Ala Lys Val
        2495               2500                2505

Thr Gly Pro Arg Leu Val Ser Asn His Ser Leu His Glu Thr Ser
        2510               2515                2520

Ser Val Phe Val Asp Ser Leu Thr Lys Ala Thr Cys Ala Pro Gln
        2525               2530                2535

His Gly Ala Pro Gly Pro Gly Pro Ala Asp Ala Ser Lys Val Val
        2540               2545                2550

Ala Lys Gly Leu Gly Leu Ser Lys Ala Tyr Val Gly Gln Lys Ser
        2555               2560                2565

Ser Phe Thr Val Asp Cys Ser Lys Ala Gly Asn Asn Met Leu Leu
        2570               2575                2580

Val Gly Val His Gly Pro Arg Thr Pro Cys Glu Glu Ile Leu Val
        2585               2590                2595

Lys His Val Gly Ser Arg Leu Tyr Ser Val Ser Tyr Leu Leu Lys
        2600               2605                2610

Asp Lys Gly Glu Tyr Thr Leu Val Val Lys Trp Gly Asp Glu His
        2615               2620                2625

Ile Pro Gly Ser Pro Tyr Arg Val Val Val Pro
        2630               2635

<210> SEQ ID NO 33
<211> LENGTH: 8557
<212> TYPE: DNA
<213> ORGANISM: Homo sapiens
<220> FEATURE:
<221> NAME/KEY: misc_feature
<222> LOCATION: (1)..(8557)
<223> OTHER INFORMATION: Filamin A, isoform 2

<400> SEQUENCE: 33
attcgcgtgg aggcgcgtcg cgcgcagcgg acgccgacag aatccccgag gcgcctggcg      60
cgggcgcggg cgcgaaggcg atccgggcgc caccccgcgg tcatcggtca ccggtcgctc     120
tcaggaacag cagcgcaacc tctgctccct gcctcgcctc ccgcgcgcct aggtgcctgc     180
```

```
gactttaatt aaagggccgt ccctcgccg aggctgcagc accgcccccc cggcttctcg    240
cgcctcaaaa tgagtagctc ccactctcgg gcgggccaga gcgcagcagg cgcggctccg    300
ggcggcggcg tcgacacgcg ggacgccgag atgccggcca ccgagaagga cctggcggag    360
gacgcgccgt ggaagaagat ccagcagaac actttcacgc gctggtgcaa cgagcacctg    420
aagtgcgtga gcaagcgcat cgccaacctg cagacggacc tgagcgacgg gctgcggctt    480
atcgcgctgt tggaggtgct cagccagaag aagatgcacc gcaagcacaa ccagcggccc    540
actttccgcc aaatgcagct gagaacgtg tcggtggcgc tcgagttcct ggaccgcgag    600
agcatcaaac tggtgtccat cgacagcaag gccatcgtgg acgggaacct gaagctgatc    660
ctgggcctca tctggaccct gatcctgcac tactccatct ccatgcccat gtgggacgag    720
gaggaggatg aggaggccaa gaagcagacc cccaagcaga ggctcctggg ctggatccag    780
aacaagctgc cgcagctgcc catcaccaac ttcagccggg actggcagag cggccgggcc    840
ctgggcgccc tggtggacag ctgtgccccg ggcctgtgtc ctgactggga ctcttgggac    900
gccagcaagc ccgttaccaa tgcgcgagag gccatgcagc aggcggatga ctggctgggc    960 atccccagg tgatcacccc cgaggagatt gtggacccca cgtgacga gcactctgtc   1020 atgacctacc tgtcccagtt ccccaaggcc aagctgaagc caggggctcc cttgcggccc   1080
aaactgaacc cgaagaaagc ccgtgcctac gggccaggca tcgagcccac aggcaacatg   1140
gtgaagaagc gggcagagtt cactgtggag accagaagtg ctggccaggg agaggtgctg   1200
gtgtacgtgg aggacccggc cggacaccag gaggaggcaa aagtgaccgc caataacgac   1260
aagaaccgca ccttctccgt ctggtacgtc cccgaggtga cggggactca taaggttact   1320
gtgctctttg ctggccagca catcgccaag agccccttcg aggtgtacgt ggataagtca   1380
cagggtgacg ccagcaaagt gacagcccaa ggtcccggcc tggagcccag tggcaacatc   1440
gccaacaaga ccacctactt tgagatcttt acggcaggag ctggcacggg cgaggtcgag   1500
gttgtgatcc aggaccccat gggacagaag ggcacggtag agcctcagct ggaggcccgg   1560
ggcgacagca cataccgctg cagctaccag cccaccatgg agggcgtcca caccgtgcac   1620
gtcacgtttg ccggcgtgcc catccctcgc agcccctaca ctgtcactgt tggccaagcc   1680
tgtaacccga gtgcctgccg ggcggttggc cggggcctcc agcccaaggg tgtgcgggtg   1740
aaggagacag ctgacttcaa ggtgtacaca aagggcgctg gcagtgggga gctgaaggtc   1800
accgtgaagg gccccaaggg agaggagcgc gtgaagcaga aggacctggg ggatggcgtg   1860 tatgcttcg agtattaccc catggtccct ggaacctata tcgtcaccat cacgtggggt   1920
ggtcagaaca tcgggcgcag tcccttcgaa gtgaaggtgg gcaccgagtg tggcaatcag   1980
aaggtacggg cctggggccc tggctggag gcggcgtc ttggcaagtc agcagacttt   2040
gtggtggagg ctatcgggga cgacgtgggc acgctgggct tctcggtgga agggccatcg   2100
caggctaaga tcgaatgtga cgacaagggc gacggctcct gtgatgtgcg ctactggccg   2160
caggaggctg gcgagtatgc cgttcacgtg ctgtgcaaca gcgaagacat ccgcctcagc   2220
cccttcatgg ctgacatccg tgacgcgccc caggacttcc acccagacag ggtgaaggca   2280
cgtgggcctg gattggagaa gacaggtgtg ccgtcaaca gccagcagga gttcacagtg   2340
gatgccaagc acgtggcaa ggccccactt cgggtccaag tccaggacaa tgaaggctgc   2400
cctgtggagg cgttggtcaa ggacaacggc aatggcactt acagctgctc ctacgtgccc   2460
aggaagccgg tgaagcacac agccatggtg tcctggggag gcgtcagcat ccccaacagc   2520
```

```
cccttcaggg tgaatgtggg agctggcagc caccccaaca aggtcaaagt atacggcccc    2580
ggagtagcca agacagggct caaggcccac gagcccacct acttcactgt ggactgcgcc    2640
gaggctggcc agggggacgt cagcatcggc atcaagtgtg ccctggagt ggtaggcccc    2700 gccgaagctg acatcgactt cgacatcatc cgcaatgaca atgacacctt cacggtcaag    2760
tacacgcccc gggggctgg cagctacacc attatggtcc tctttgctga ccaggccacg    2820
cccaccagcc ccatccgagt caaggtggag ccctctcatg acgccagtaa ggtgaaggcc    2880
gagggccctg gcctcagtcg cactggtgtc gagcttggca gcccacccca cttcacagta    2940
aatgccaaag ctgctggcaa aggcaagctg acgtccagt tctcaggact caccaagggg    3000
gatgcagtgc gagatgtgga catcatcgac caccatgaca acacctacac agtcaagtac    3060
acgcctgtcc agcagggtcc agtaggcgtc aatgtcactt atggagggga tcccatccct    3120
aagagccctt tctcagtggc agtatctcca agcctggacc tcagcaagat caaggtgtct    3180
ggcctgggag agaaggtgga cgttggcaaa gaccaggagt tcacagtcaa atcaaagggt    3240
gctggtggtc aaggcaaagt ggcatccaag attgtgggcc cctcgggtgc agcggtgccc    3300
tgcaaggtgg agccaggcct gggggctgac aacagtgtgg tgcgcttcct gccccgtgag    3360
gaagggccct atgaggtgga ggtgacctat gacgcgtgc ccgtgcctgg cagcccctt    3420 cctctggaag ctgtggcccc caccaagcct agcaaggtga aggcgtttgg gccggggctg    3480
cagggaggca gtgcgggctc ccccgcccgc ttcaccatcg acaccaaggg cgccggcaca    3540
ggtggcctgg gcctgacggt ggagggcccc tgtgaggcgc agctcgagtg cttggacaat    3600
ggggatggca catgttccgt gtcctacgtg cccaccgagc ccggggacta caacatcaac    3660
atcctcttcg ctgacaccca catccctggc tccccattca aggcccacgt ggttccctgc    3720
tttgacgcat ccaaagtcaa gtgctcaggc cccgggctgg agcgggccac cgctggggag    3780
gtgggccaat tccaagtgga ctgctcgagc gcgggcagcg cggagctgac cattgagatc    3840
tgctcggagg cggggcttcc ggccgaggtg tacatccagg accacggtga tggcacgcac    3900
accattacct acattcccct ctgcccgggg gcctacaccg tcaccatcaa gtacggcggc    3960
cagcccgtgc ccaacttccc cagcaagctg caggtggaac ctgcggtgga cacttccggt    4020
gtccagtgct atgggcctgg tattgagggc cagggtgtct tccgtgaggc caccactgag    4080
ttcagtgtgg acgcccgggc tctgacacag accgagggc cgcacgtcaa ggcccgtgtg    4140
gccaacccct caggcaacct gacggagacc tacgttcagg accgtggcga tggcatgtac    4200
aaagtggagt acacgcctta cgaggaggga ctgcactccg tggacgtgac ctatgacggc    4260
agtcccgtgc ccagcagccc cttccaggtg cccgtgaccg agggctgcga cccctcccgg    4320
gtgcgtgtcc acgggccagg catccaaagt ggcaccacca acaagcccaa caagttcact    4380
gtggagacca ggggagctgg cacgggcggc ctgggcctgg ctgtagaggg cccctccgag    4440
gccaagatgt cctgcatgga taacaaggac ggcagctgct cggtcgagta catccccttat    4500 gaggctggca cctacagcct caacgtcacc tatggtggcc atcaagtgcc aggcagtcct    4560
ttcaaggtcc ctgtgcatga tgtgacagat gcgtccaagg tcaagtgctc tgggcccggc    4620
ctgagcccag gcatggttcg tgccaacctc cctcagtcct tccaggtgga cacaagcaag    4680
gctggtgtgg ccccattgca ggtcaaagtg caagggccca aaggcctggt ggagccagtg    4740
gacgtggtag acaacgctga tggcacccag accgtcaatt atgtgccag ccgagaaggg    4800 ccctacagca tctcagtact gtatggagat gaagaggtac cccggagccc cttcaaggtc    4860
aaggtgctgc ctactcatga tgccagcaag gtgaaggcca gtggccccgg gctcaacacc    4920
```

```
actggcgtgc ctgccagcct gcccgtggag ttcaccatcg atgcaaagga cgccggggag   4980
ggcctgctgg ctgtccagat cacggatccc gaaggcaagc cgaagaagac acacatccaa   5040
gacaaccatg acggcacgta tacagtggcc tacgtgccag acgtgacagg tcgctacacc   5100
atcctcatca agtacggtgg tgacgagatc cccttctccc cgtaccgcgt gcgtgccgtg   5160
cccaccgggg acgccagcaa gtgcactgtc acagtgtcaa tcggaggtca cgggctaggt   5220
gctggcatcg gccccaccat tcagattggg gaggagacgg tgatcactgt ggacactaag   5280
gcggcaggca aaggcaaagt gacgtgcacc gtgtgcacgc ctgatggctc agaggtggat   5340
gtggacgtgg tggagaatga ggacggcact ttcgacatct tctacacggc cccccagccg   5400
ggcaaatacg tcatctgtgt gcgctttggt ggcgagcacg tgcccaacag ccccttccaa   5460
gtgacggctc tggctgggga ccagccctcg gtgcagcccc ctctacggtc tcagcagctg   5520
gccccacagt acacctacgc ccagggcggc cagcagactt gggccccgga gaggcccctg   5580
gtgggtgtca atgggctgga tgtgaccagc ctgaggccct ttgaccttgt catcccttc   5640 accatcaaga agggcgagat cacaggggag gttcggatgc cctcaggcaa ggtggcgcag   5700
cccaccatca ctgacaacaa agacggcacc gtgaccgtgc ggtatgcacc cagcgaggct   5760
ggcctgcacg agatggacat ccgctatgac aacatgcaca tcccaggaag ccccttgcag   5820
ttctatgtgg attacgtcaa ctgtggccat gtcactgcct atgggcctgg cctcacccat   5880
ggagtagtga acaagcctgc caccttcacc gtcaacacca aggatgcagg agagggggc   5940 ctgtctctgg ccattgaggg cccgtccaaa gcagaaatca gctgcactga caaccaggat   6000
gggacatgca gcgtgtccta cctgcctgtg ctgccggggg actacagcat tctagtcaag   6060
tacaatgaac agcacgtccc aggcagcccc ttcactgctc gggtcacagg tgacgactcc   6120
atgcgtatgt cccacctaaa ggtcggctct gctgccgaca tccccatcaa catctcagag   6180
acggatctca gcctgctgac ggccactgtg gtcccgccct cgggccggga ggagccctgt   6240
ttgctgaagc ggctgcgtaa tggccacgtg gggatttcat tcgtgcccaa ggagacgggg   6300
gagcacctgg tgcatgtgaa gaaaaatggc cagcacgtgg ccagcagccc catcccggtg   6360
gtgatcagcc agtcggaaat tggggatgcc agtcgtgttc gggtctctgg tcagggcctt   6420
cacgaaggcc acacctttga gcctgcagag tttatcattg atacccgcga tgcaggctat   6480
ggtgggctca gcctgtccat tgagggcccc agcaaggtgg acatcaacac agaggacctg   6540
gaggacggga cgtgcagggt cacctactgc cccacagagc caggcaacta catcatcaac   6600
atcaagtttg ccgaccagca cgtgcctggc agccccttct ctgtgaaggt gacaggcgag   6660
ggccgggtga agagagcat cacccgcagg cgtcgggctc cttcagtggc caacgttggt   6720
agtcattgtg acctcagcct gaaaatccct gaaattagca tccaggatat gacagcccag   6780
gtgaccagcc catcgggcaa gacccatgag gccgagatcg tggaagggga gaaccacacc   6840
tactgcatcc gctttgttcc cgctgagatg ggcacacaca cagtcagcgt gaagtacaag   6900
ggccagcacg tgcctgggag ccccttccag ttcaccgtgg ggcccctagg ggaaggggga   6960
gcccacaagg tccgagctgg gggccctggc ctggagagag ctgaagctgg agtgccagcc   7020
gaattcagta tctggacccg ggaagctggt gctggaggcc tggccattgc tgtcgagggc   7080
cccagcaagg ctgagatctc ttttgaggac cgcaaggacg gctcctgtgg tgtggcttat   7140
gtggtccagg agccaggtga ctacgaagtc tcagtcaagt tcaacgagga acacattccc   7200
gacagcccct tcgtggtgcc tgtggcttct ccgtctggcg acgcccgccg cctcactgtt   7260
```

```
tctagccttc aggagtcagg gctaaaggtc aaccagccag cctcttttgc agtcagcctg    7320
aacgggccca aggggcgat cgatgccaag gtgcacagcc cctcaggagc cctggaggag     7380
tgctatgtca cagaaattga ccaagataag tatgctgtgc gcttcatccc tcgggagaat    7440
ggcgtttacc tgattgacgt caagttcaac ggcacccaca tccctggaag cccttcaag    7500 atccgagttg gggagcctgg gcatggaggg gacccaggct tggtgtctgc ttacggagca    7560
ggtctggaag gcggtgtcac agggaaccca gctgagttcg tcgtgaacac gagcaatgcg    7620
ggagctggtg ccctgtcggt gaccattgac ggcccctcca aggtgaagat ggattgccag    7680
gagtgccctg agggctaccg cgtcacctat accccatgg cacctggcag ctacctcatc     7740
tccatcaagt acggcggccc ctaccacatt ggggcagcc ccttcaaggc caaagtcaca     7800 ggccccgtc tcgtcagcaa ccacagcctc cacgagacat catcagtgtt tgtagactct     7860
ctgaccaagg ccacctgtgc ccccagcat ggggccccgg gtcctgggcc tgctgacgcc    7920
agcaaggtgg tggccaaggg cctggggctg agcaaggcct acgtaggcca gaagagcagc    7980
ttcacagtag actgcagcaa agcaggcaac aacatgctgc tggtgggggt tcatggccca    8040 aggacccct gcgaggagat cctggtgaag cacgtgggca gccggctcta cagcgtgtcc     8100
tacctgctca aggacaaggg ggagtacaca ctggtggtca atgggggga cgagcacatc    8160 ccaggcagcc cctaccgcgt tgtggtgccc tgagtctggg gcccgtgcca gccggcagcc    8220
cccaagcctg ccccgctacc caagcagccc cgccctcttc ccctcaaccc cggcccaggc    8280
cgccctggcc gcccgcctgt cactgcagcc gccctgccc tgtgccgtgc tgcgctcacc    8340
tgcctcccca gccagccgct gacctctcgg ctttcacttg ggcagaggga gccatttggt    8400
ggcgctgctt gtcttctttg gttctgggag gggtgaggga tgggggtcct gtacacaacc    8460
acccactagt tctcttctcc agccaagagg aataaagttt tgcttccatt aaaaaaaaaa    8520
aaaaaaaaaa aaaaaaaaaa aaaaaaaaaa aaaaaaa                             8557
```

<210> SEQ ID NO 34
<211> LENGTH: 2647
<212> TYPE: PRT
<213> ORGANISM: Homo sapiens
<220> FEATURE:
<221> NAME/KEY: misc_feature
<222> LOCATION: (1)..(2647)
<223> OTHER INFORMATION: Filamin A, isoform 2

<400> SEQUENCE: 34

```
Met Ser Ser Ser His Ser Arg Ala Gly Gln Ser Ala Ala Gly Ala Ala
1               5                   10                  15

Pro Gly Gly Gly Val Asp Thr Arg Asp Ala Glu Met Pro Ala Thr Glu
            20                  25                  30

Lys Asp Leu Ala Glu Asp Ala Pro Trp Lys Lys Ile Gln Gln Asn Thr
        35                  40                  45

Phe Thr Arg Trp Cys Asn Glu His Leu Lys Cys Val Ser Lys Arg Ile
    50                  55                  60

Ala Asn Leu Gln Thr Asp Leu Ser Asp Gly Leu Arg Leu Ile Ala Leu
65                  70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125
```

```
Ile Val Asp Gly Asn Leu Lys Leu Ile Leu Gly Leu Ile Trp Thr Leu
    130                 135                 140
Ile Leu His Tyr Ser Ile Ser Met Pro Met Trp Asp Glu Glu Glu Asp
145                 150                 155                 160
Glu Glu Ala Lys Lys Gln Thr Pro Lys Gln Arg Leu Leu Gly Trp Ile
                165                 170                 175
Gln Asn Lys Leu Pro Gln Leu Pro Ile Thr Asn Phe Ser Arg Asp Trp
            180                 185                 190
Gln Ser Gly Arg Ala Leu Gly Ala Leu Val Asp Ser Cys Ala Pro Gly
        195                 200                 205
Leu Cys Pro Asp Trp Asp Ser Trp Asp Ala Ser Lys Pro Val Thr Asn
    210                 215                 220
Ala Arg Glu Ala Met Gln Gln Ala Asp Asp Trp Leu Gly Ile Pro Gln
225                 230                 235                 240
Val Ile Thr Pro Glu Glu Ile Val Asp Pro Asn Val Asp Glu His Ser
                245                 250                 255
Val Met Thr Tyr Leu Ser Gln Phe Pro Lys Ala Lys Leu Lys Pro Gly
            260                 265                 270
Ala Pro Leu Arg Pro Lys Leu Asn Pro Lys Lys Ala Arg Ala Tyr Gly
        275                 280                 285
Pro Gly Ile Glu Pro Thr Gly Asn Met Val Lys Lys Arg Ala Glu Phe
    290                 295                 300
Thr Val Glu Thr Arg Ser Ala Gly Gln Gly Glu Val Leu Val Tyr Val
305                 310                 315                 320
Glu Asp Pro Ala Gly His Gln Glu Glu Ala Lys Val Thr Ala Asn Asn
                325                 330                 335
Asp Lys Asn Arg Thr Phe Ser Val Trp Tyr Val Pro Glu Val Thr Gly
            340                 345                 350
Thr His Lys Val Thr Val Leu Phe Ala Gly Gln His Ile Ala Lys Ser
        355                 360                 365
Pro Phe Glu Val Tyr Val Asp Lys Ser Gln Gly Asp Ala Ser Lys Val
    370                 375                 380
Thr Ala Gln Gly Pro Gly Leu Glu Pro Ser Gly Asn Ile Ala Asn Lys
385                 390                 395                 400
Thr Thr Tyr Phe Glu Ile Phe Thr Ala Gly Ala Gly Thr Gly Glu Val
                405                 410                 415
Glu Val Val Ile Gln Asp Pro Met Gly Gln Lys Gly Thr Val Glu Pro
            420                 425                 430
Gln Leu Glu Ala Arg Gly Asp Ser Thr Tyr Arg Cys Ser Tyr Gln Pro
        435                 440                 445
Thr Met Glu Gly Val His Thr Val His Val Thr Phe Ala Gly Val Pro
    450                 455                 460
Ile Pro Arg Ser Pro Tyr Thr Val Thr Val Gly Gln Ala Cys Asn Pro
465                 470                 475                 480
Ser Ala Cys Arg Ala Val Gly Arg Gly Leu Gln Pro Lys Gly Val Arg
                485                 490                 495
Val Lys Glu Thr Ala Asp Phe Lys Val Tyr Thr Lys Gly Ala Gly Ser
            500                 505                 510
Gly Glu Leu Lys Val Thr Val Lys Gly Pro Lys Gly Glu Glu Arg Val
        515                 520                 525
Lys Gln Lys Asp Leu Gly Asp Gly Val Tyr Gly Phe Glu Tyr Tyr Pro
    530                 535                 540
```

```
Met Val Pro Gly Thr Tyr Ile Val Thr Ile Thr Trp Gly Gly Gln Asn
545                 550                 555                 560

Ile Gly Arg Ser Pro Phe Glu Val Lys Val Gly Thr Glu Cys Gly Asn
                565                 570                 575

Gln Lys Val Arg Ala Trp Gly Pro Gly Leu Glu Gly Gly Val Val Gly
            580                 585                 590

Lys Ser Ala Asp Phe Val Val Glu Ala Ile Gly Asp Val Gly Thr
        595                 600                 605

Leu Gly Phe Ser Val Glu Gly Pro Ser Gln Ala Lys Ile Glu Cys Asp
    610                 615                 620

Asp Lys Gly Asp Gly Ser Cys Asp Val Arg Tyr Trp Pro Gln Glu Ala
625                 630                 635                 640

Gly Glu Tyr Ala Val His Val Leu Cys Asn Ser Glu Asp Ile Arg Leu
                645                 650                 655

Ser Pro Phe Met Ala Asp Ile Arg Asp Ala Pro Gln Asp Phe His Pro
            660                 665                 670

Asp Arg Val Lys Ala Arg Gly Pro Gly Leu Glu Lys Thr Gly Val Ala
        675                 680                 685

Val Asn Lys Pro Ala Glu Phe Thr Val Asp Ala Lys His Gly Gly Lys
    690                 695                 700

Ala Pro Leu Arg Val Gln Val Gln Asp Asn Glu Gly Cys Pro Val Glu
705                 710                 715                 720

Ala Leu Val Lys Asp Asn Gly Asn Gly Thr Tyr Ser Cys Ser Tyr Val
                725                 730                 735

Pro Arg Lys Pro Val Lys His Thr Ala Met Val Ser Trp Gly Gly Val
            740                 745                 750

Ser Ile Pro Asn Ser Pro Phe Arg Val Asn Val Gly Ala Gly Ser His
        755                 760                 765

Pro Asn Lys Val Lys Val Tyr Gly Pro Gly Val Ala Lys Thr Gly Leu
    770                 775                 780

Lys Ala His Glu Pro Thr Tyr Phe Thr Val Asp Cys Ala Glu Ala Gly
785                 790                 795                 800

Gln Gly Asp Val Ser Ile Gly Ile Lys Cys Ala Pro Gly Val Val Gly
                805                 810                 815

Pro Ala Glu Ala Asp Ile Asp Phe Asp Ile Ile Arg Asn Asp Asn Asp
            820                 825                 830

Thr Phe Thr Val Lys Tyr Thr Pro Arg Gly Ala Gly Ser Tyr Thr Ile
        835                 840                 845

Met Val Leu Phe Ala Asp Gln Ala Thr Pro Thr Ser Pro Ile Arg Val
850                 855                 860

Lys Val Glu Pro Ser His Asp Ala Ser Lys Val Lys Ala Glu Gly Pro
865                 870                 875                 880

Gly Leu Ser Arg Thr Gly Val Glu Leu Gly Lys Pro Thr His Phe Thr
                885                 890                 895

Val Asn Ala Lys Ala Ala Gly Lys Gly Lys Leu Asp Val Gln Phe Ser
            900                 905                 910

Gly Leu Thr Lys Gly Asp Ala Val Arg Asp Val Asp Ile Ile Asp His
        915                 920                 925

His Asp Asn Thr Tyr Thr Val Lys Tyr Thr Pro Val Gln Gln Gly Pro
    930                 935                 940

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
```

965                 970                 975
Ser Gly Leu Gly Glu Lys Val Asp Val Gly Lys Asp Gln Glu Phe Thr
                980                 985                 990

Val Lys Ser Lys Gly Ala Gly Gly Gln Gly Lys Val Ala Ser Lys Ile
        995                 1000                1005

Val Gly Pro Ser Gly Ala Ala Val Pro Cys Lys Val Glu Pro Gly
    1010                1015                1020

Leu Gly Ala Asp Asn Ser Val Val Arg Phe Leu Pro Arg Glu Glu
    1025                1030                1035

Gly Pro Tyr Glu Val Glu Val Thr Tyr Asp Gly Val Pro Val Pro
    1040                1045                1050

Gly Ser Pro Phe Pro Leu Glu Ala Val Ala Pro Thr Lys Pro Ser
    1055                1060                1065

Lys Val Lys Ala Phe Gly Pro Gly Leu Gln Gly Gly Ser Ala Gly
    1070                1075                1080

Ser Pro Ala Arg Phe Thr Ile Asp Thr Lys Gly Ala Gly Thr Gly
    1085                1090                1095

Gly Leu Gly Leu Thr Val Glu Gly Pro Cys Glu Ala Gln Leu Glu
    1100                1105                1110

Cys Leu Asp Asn Gly Asp Gly Thr Cys Ser Val Ser Tyr Val Pro
    1115                1120                1125

Thr Glu Pro Gly Asp Tyr Asn Ile Asn Ile Leu Phe Ala Asp Thr
    1130                1135                1140

His Ile Pro Gly Ser Pro Phe Lys Ala His Val Val Pro Cys Phe
    1145                1150                1155

Asp Ala Ser Lys Val Lys Cys Ser Gly Pro Gly Leu Glu Arg Ala
    1160                1165                1170

Thr Ala Gly Glu Val Gly Gln Phe Gln Val Asp Cys Ser Ser Ala
    1175                1180                1185

Gly Ser Ala Glu Leu Thr Ile Glu Ile Cys Ser Glu Ala Gly Leu
    1190                1195                1200

Pro Ala Glu Val Tyr Ile Gln Asp His Gly Asp Gly Thr His Thr
    1205                1210                1215

Ile Thr Tyr Ile Pro Leu Cys Pro Gly Ala Tyr Thr Val Thr Ile
    1220                1225                1230

Lys Tyr Gly Gly Gln Pro Val Pro Asn Phe Pro Ser Lys Leu Gln
    1235                1240                1245

Val Glu Pro Ala Val Asp Thr Ser Gly Val Gln Cys Tyr Gly Pro
    1250                1255                1260

Gly Ile Glu Gly Gln Gly Val Phe Arg Glu Ala Thr Thr Glu Phe
    1265                1270                1275

Ser Val Asp Ala Arg Ala Leu Thr Gln Thr Gly Gly Pro His Val
    1280                1285                1290

Lys Ala Arg Val Ala Asn Pro Ser Gly Asn Leu Thr Glu Thr Tyr
    1295                1300                1305

Val Gln Asp Arg Gly Asp Gly Met Tyr Lys Val Glu Tyr Thr Pro
    1310                1315                1320

Tyr Glu Glu Gly Leu His Ser Val Asp Val Thr Tyr Asp Gly Ser
    1325                1330                1335

Pro Val Pro Ser Ser Pro Phe Gln Val Pro Val Thr Glu Gly Cys
    1340                1345                1350

Asp Pro Ser Arg Val Arg Val His Gly Pro Gly Ile Gln Ser Gly
    1355                1360                1365

```
Thr Thr Asn Lys Pro Asn Lys Phe Thr Val Glu Thr Arg Gly Ala
1370            1375                1380

Gly Thr Gly Gly Leu Gly Leu Ala Val Glu Gly Pro Ser Glu Ala
    1385            1390                1395

Lys Met Ser Cys Met Asp Asn Lys Asp Gly Ser Cys Ser Val Glu
1400                1405                1410

Tyr Ile Pro Tyr Glu Ala Gly Thr Tyr Ser Leu Asn Val Thr Tyr
    1415            1420                1425

Gly Gly His Gln Val Pro Gly Ser Pro Phe Lys Val Pro Val His
1430                1435                1440

Asp Val Thr Asp Ala Ser Lys Val Lys Cys Ser Gly Pro Gly Leu
    1445            1450                1455

Ser Pro Gly Met Val Arg Ala Asn Leu Pro Gln Ser Phe Gln Val
1460                1465                1470

Asp Thr Ser Lys Ala Gly Val Ala Pro Leu Gln Val Lys Val Gln
    1475            1480                1485

Gly Pro Lys Gly Leu Val Glu Pro Val Asp Val Asp Asn Ala
1490                1495                1500

Asp Gly Thr Gln Thr Val Asn Tyr Val Pro Ser Arg Glu Gly Pro
    1505            1510                1515

Tyr Ser Ile Ser Val Leu Tyr Gly Asp Glu Glu Val Pro Arg Ser
1520                1525                1530

Pro Phe Lys Val Lys Val Leu Pro Thr His Asp Ala Ser Lys Val
    1535            1540                1545

Lys Ala Ser Gly Pro Gly Leu Asn Thr Thr Gly Val Pro Ala Ser
1550                1555                1560

Leu Pro Val Glu Phe Thr Ile Asp Ala Lys Asp Ala Gly Glu Gly
    1565            1570                1575

Leu Leu Ala Val Gln Ile Thr Asp Pro Glu Gly Lys Pro Lys Lys
1580                1585                1590

Thr His Ile Gln Asp Asn His Asp Gly Thr Tyr Thr Val Ala Tyr
    1595            1600                1605

Val Pro Asp Val Thr Gly Arg Tyr Thr Ile Leu Ile Lys Tyr Gly
1610                1615                1620

Gly Asp Glu Ile Pro Phe Ser Pro Tyr Arg Val Arg Ala Val Pro
    1625            1630                1635

Thr Gly Asp Ala Ser Lys Cys Thr Val Thr Val Ser Ile Gly Gly
1640                1645                1650

His Gly Leu Gly Ala Gly Ile Gly Pro Thr Ile Gln Ile Gly Glu
    1655            1660                1665

Glu Thr Val Ile Thr Val Asp Thr Lys Ala Ala Gly Lys Gly Lys
1670                1675                1680

Val Thr Cys Thr Val Cys Thr Pro Asp Gly Ser Glu Val Asp Val
    1685            1690                1695

Asp Val Val Glu Asn Glu Asp Gly Thr Phe Asp Ile Phe Tyr Thr
1700                1705                1710

Ala Pro Gln Pro Gly Lys Tyr Val Ile Cys Val Arg Phe Gly Gly
    1715            1720                1725

Glu His Val Pro Asn Ser Pro Phe Gln Val Thr Ala Leu Ala Gly
1730                1735                1740

Asp Gln Pro Ser Val Gln Pro Pro Leu Arg Ser Gln Gln Leu Ala
    1745            1750                1755
```

```
Pro Gln Tyr Thr Tyr Ala Gln Gly Gly Gln Gln Thr Trp Ala Pro
    1760                1765                1770

Glu Arg Pro Leu Val Gly Val Asn Gly Leu Asp Val Thr Ser Leu
    1775                1780                1785

Arg Pro Phe Asp Leu Val Ile Pro Phe Thr Ile Lys Lys Gly Glu
    1790                1795                1800

Ile Thr Gly Glu Val Arg Met Pro Ser Gly Lys Val Ala Gln Pro
    1805                1810                1815

Thr Ile Thr Asp Asn Lys Asp Gly Thr Val Thr Val Arg Tyr Ala
    1820                1825                1830

Pro Ser Glu Ala Gly Leu His Glu Met Asp Ile Arg Tyr Asp Asn
    1835                1840                1845

Met His Ile Pro Gly Ser Pro Leu Gln Phe Tyr Val Asp Tyr Val
    1850                1855                1860

Asn Cys Gly His Val Thr Ala Tyr Gly Pro Gly Leu Thr His Gly
    1865                1870                1875

Val Val Asn Lys Pro Ala Thr Phe Thr Val Asn Thr Lys Asp Ala
    1880                1885                1890

Gly Glu Gly Gly Leu Ser Leu Ala Ile Glu Gly Pro Ser Lys Ala
    1895                1900                1905

Glu Ile Ser Cys Thr Asp Asn Gln Asp Gly Thr Cys Ser Val Ser
    1910                1915                1920

Tyr Leu Pro Val Leu Pro Gly Asp Tyr Ser Ile Leu Val Lys Tyr
    1925                1930                1935

Asn Glu Gln His Val Pro Gly Ser Pro Phe Thr Ala Arg Val Thr
    1940                1945                1950

Gly Asp Asp Ser Met Arg Met Ser His Leu Lys Val Gly Ser Ala
    1955                1960                1965

Ala Asp Ile Pro Ile Asn Ile Ser Glu Thr Asp Leu Ser Leu Leu
    1970                1975                1980

Thr Ala Thr Val Val Pro Pro Ser Gly Arg Glu Glu Pro Cys Leu
    1985                1990                1995

Leu Lys Arg Leu Arg Asn Gly His Val Gly Ile Ser Phe Val Pro
    2000                2005                2010

Lys Glu Thr Gly Glu His Leu Val His Val Lys Lys Asn Gly Gln
    2015                2020                2025

His Val Ala Ser Ser Pro Ile Pro Val Val Ile Ser Gln Ser Glu
    2030                2035                2040

Ile Gly Asp Ala Ser Arg Val Arg Val Ser Gly Gln Gly Leu His
    2045                2050                2055

Glu Gly His Thr Phe Glu Pro Ala Glu Phe Ile Ile Asp Thr Arg
    2060                2065                2070

Asp Ala Gly Tyr Gly Gly Leu Ser Leu Ser Ile Glu Gly Pro Ser
    2075                2080                2085

Lys Val Asp Ile Asn Thr Glu Asp Leu Glu Asp Gly Thr Cys Arg
    2090                2095                2100

Val Thr Tyr Cys Pro Thr Glu Pro Gly Asn Tyr Ile Ile Asn Ile
    2105                2110                2115

Lys Phe Ala Asp Gln His Val Pro Gly Ser Pro Phe Ser Val Lys
    2120                2125                2130

Val Thr Gly Glu Gly Arg Val Lys Glu Ser Ile Thr Arg Arg Arg
    2135                2140                2145

Arg Ala Pro Ser Val Ala Asn Val Gly Ser His Cys Asp Leu Ser
```

```
                         2150                     2155                    2160

Leu Lys Ile Pro Glu Ile Ser Ile Gln Asp Met Thr Ala Gln Val
        2165                    2170                    2175

Thr Ser Pro Ser Gly Lys Thr His Glu Ala Glu Ile Val Glu Gly
        2180                    2185                    2190

Glu Asn His Thr Tyr Cys Ile Arg Phe Val Pro Ala Glu Met Gly
        2195                    2200                    2205

Thr His Thr Val Ser Val Lys Tyr Lys Gly Gln His Val Pro Gly
        2210                    2215                    2220

Ser Pro Phe Gln Phe Thr Val Gly Pro Leu Gly Glu Gly Gly Ala
        2225                    2230                    2235

His Lys Val Arg Ala Gly Gly Pro Gly Leu Glu Arg Ala Glu Ala
        2240                    2245                    2250

Gly Val Pro Ala Glu Phe Ser Ile Trp Thr Arg Glu Ala Gly Ala
        2255                    2260                    2265

Gly Gly Leu Ala Ile Ala Val Glu Gly Pro Ser Lys Ala Glu Ile
        2270                    2275                    2280

Ser Phe Glu Asp Arg Lys Asp Gly Ser Cys Gly Val Ala Tyr Val
        2285                    2290                    2295

Val Gln Glu Pro Gly Asp Tyr Glu Val Ser Val Lys Phe Asn Glu
        2300                    2305                    2310

Glu His Ile Pro Asp Ser Pro Phe Val Val Pro Val Ala Ser Pro
        2315                    2320                    2325

Ser Gly Asp Ala Arg Arg Leu Thr Val Ser Ser Leu Gln Glu Ser
        2330                    2335                    2340

Gly Leu Lys Val Asn Gln Pro Ala Ser Phe Ala Val Ser Leu Asn
        2345                    2350                    2355

Gly Ala Lys Gly Ala Ile Asp Ala Lys Val His Ser Pro Ser Gly
        2360                    2365                    2370

Ala Leu Glu Glu Cys Tyr Val Thr Glu Ile Asp Gln Asp Lys Tyr
        2375                    2380                    2385

Ala Val Arg Phe Ile Pro Arg Glu Asn Gly Val Tyr Leu Ile Asp
        2390                    2395                    2400

Val Lys Phe Asn Gly Thr His Ile Pro Gly Ser Pro Phe Lys Ile
        2405                    2410                    2415

Arg Val Gly Glu Pro Gly His Gly Gly Asp Pro Gly Leu Val Ser
        2420                    2425                    2430

Ala Tyr Gly Ala Gly Leu Glu Gly Gly Val Thr Gly Asn Pro Ala
        2435                    2440                    2445

Glu Phe Val Val Asn Thr Ser Asn Ala Gly Ala Gly Ala Leu Ser
        2450                    2455                    2460

Val Thr Ile Asp Gly Pro Ser Lys Val Lys Met Asp Cys Gln Glu
        2465                    2470                    2475

Cys Pro Glu Gly Tyr Arg Val Thr Tyr Thr Pro Met Ala Pro Gly
        2480                    2485                    2490

Ser Tyr Leu Ile Ser Ile Lys Tyr Gly Gly Pro Tyr His Ile Gly
        2495                    2500                    2505

Gly Ser Pro Phe Lys Ala Lys Val Thr Gly Pro Arg Leu Val Ser
        2510                    2515                    2520

Asn His Ser Leu His Glu Thr Ser Ser Val Phe Val Asp Ser Leu
        2525                    2530                    2535

Thr Lys Ala Thr Cys Ala Pro Gln His Gly Ala Pro Gly Pro Gly
        2540                    2545                    2550
```

```
Pro Ala Asp Ala Ser Lys Val Val Ala Lys Gly Leu Gly Leu Ser
    2555            2560                2565

Lys Ala Tyr Val Gly Gln Lys Ser Ser Phe Thr Val Asp Cys Ser
    2570            2575                2580

Lys Ala Gly Asn Asn Met Leu Leu Val Gly Val His Gly Pro Arg
    2585            2590                2595

Thr Pro Cys Glu Glu Ile Leu Val Lys His Val Gly Ser Arg Leu
    2600            2605                2610

Tyr Ser Val Ser Tyr Leu Leu Lys Asp Lys Gly Glu Tyr Thr Leu
    2615            2620                2625

Val Val Lys Trp Gly Asp Glu His Ile Pro Gly Ser Pro Tyr Arg
    2630            2635                2640

Val Val Val Pro
    2645

<210> SEQ ID NO 35
<211> LENGTH: 696
<212> TYPE: PRT
<213> ORGANISM: Homo sapiens
<220> FEATURE:
<221> NAME/KEY: misc_feature
<222> LOCATION: (1)..(696)
<223> OTHER INFORMATION: Filamin A immunogen

<400> SEQUENCE: 35

Met His His His His His His Asp Val Thr Asp Ala Ser Lys Val
1               5                   10                  15

Lys Cys Ser Gly Pro Gly Leu Ser Pro Gly Met Val Arg Ala Asn Leu
                20                  25                  30

Pro Gln Ser Phe Gln Val Asp Thr Ser Lys Ala Gly Val Ala Pro Leu
        35                  40                  45

Gln Val Lys Val Gln Gly Pro Lys Gly Leu Val Glu Pro Val Asp Val
        50                  55                  60

Val Asp Asn Ala Asp Gly Thr Gln Thr Val Asn Tyr Val Pro Ser Arg
65                  70                  75                  80

Glu Gly Pro Tyr Ser Ile Ser Val Leu Tyr Gly Asp Glu Glu Val Pro
                85                  90                  95

Arg Ser Pro Phe Lys Val Lys Val Leu Pro Thr His Asp Ala Ser Lys
            100                 105                 110

Val Lys Ala Ser Gly Pro Gly Leu Asn Thr Thr Gly Val Pro Ala Ser
        115                 120                 125

Leu Pro Val Glu Phe Thr Ile Asp Ala Lys Asp Ala Gly Glu Gly Leu
    130                 135                 140

Leu Ala Val Gln Ile Thr Asp Pro Glu Gly Lys Pro Lys Lys Thr His
145                 150                 155                 160

Ile Gln Asp Asn His Asp Gly Thr Tyr Thr Val Ala Tyr Val Pro Asp
                165                 170                 175

Val Thr Gly Arg Tyr Thr Ile Leu Ile Lys Tyr Gly Gly Asp Glu Ile
            180                 185                 190

Pro Phe Ser Pro Tyr Arg Val Arg Ala Val Pro Thr Gly Asp Ala Ser
        195                 200                 205

Lys Cys Thr Val Thr Val Ser Ile Gly Gly His Gly Leu Gly Ala Gly
        210                 215                 220

Ile Gly Pro Thr Ile Gln Ile Gly Glu Glu Thr Val Ile Thr Val Asp
225                 230                 235                 240
```

```
Thr Lys Ala Ala Gly Lys Gly Lys Val Thr Cys Thr Val Cys Thr Pro
                245                 250                 255

Asp Gly Ser Glu Val Asp Val Val Glu Asn Glu Asp Gly Thr
            260                 265                 270

Phe Asp Ile Phe Tyr Thr Ala Pro Gln Pro Gly Lys Tyr Val Ile Cys
        275                 280                 285

Val Arg Phe Gly Gly Glu His Val Pro Asn Ser Pro Phe Gln Val Thr
    290                 295                 300

Ala Leu Ala Gly Asp Gln Pro Ser Val Gln Pro Leu Arg Ser Gln
305                 310                 315                 320

Gln Leu Ala Pro Gln Tyr Thr Tyr Ala Gln Gly Gly Gln Gln Thr Trp
                325                 330                 335

Ala Pro Glu Arg Pro Leu Val Gly Val Asn Gly Leu Asp Val Thr Ser
            340                 345                 350

Leu Arg Pro Phe Asp Leu Val Ile Pro Phe Thr Ile Lys Lys Gly Glu
        355                 360                 365

Ile Thr Gly Glu Val Arg Met Pro Ser Gly Lys Val Ala Gln Pro Thr
    370                 375                 380

Ile Thr Asp Asn Lys Asp Gly Thr Val Thr Val Arg Tyr Ala Pro Ser
385                 390                 395                 400

Glu Ala Gly Leu His Glu Met Asp Ile Arg Tyr Asp Asn Met His Ile
                405                 410                 415

Pro Gly Ser Pro Leu Gln Phe Tyr Val Asp Tyr Val Asn Cys Gly His
            420                 425                 430

Val Thr Ala Tyr Gly Pro Gly Leu Thr His Gly Val Val Asn Lys Pro
        435                 440                 445

Ala Thr Phe Thr Val Asn Thr Lys Asp Ala Gly Glu Gly Gly Leu Ser
    450                 455                 460

Leu Ala Ile Glu Gly Pro Ser Lys Ala Glu Ile Ser Cys Thr Asp Asn
465                 470                 475                 480

Gln Asp Gly Thr Cys Ser Val Ser Tyr Leu Pro Val Leu Pro Gly Asp
                485                 490                 495

Tyr Ser Ile Leu Val Lys Tyr Asn Glu Gln His Val Pro Gly Ser Pro
            500                 505                 510

Phe Thr Ala Arg Val Thr Gly Asp Asp Ser Met Arg Met Ser His Leu
        515                 520                 525

Lys Val Gly Ser Ala Ala Asp Ile Pro Ile Asn Ile Ser Glu Thr Asp
    530                 535                 540

Leu Ser Leu Leu Thr Ala Thr Val Val Pro Pro Ser Gly Arg Glu Glu
545                 550                 555                 560

Pro Cys Leu Leu Lys Arg Leu Arg Asn Gly His Val Gly Ile Ser Phe
                565                 570                 575

Val Pro Lys Glu Thr Gly Glu His Leu Val His Val Lys Lys Asn Gly
            580                 585                 590

Gln His Val Ala Ser Ser Pro Ile Pro Val Val Ile Ser Gln Ser Glu
        595                 600                 605

Ile Gly Asp Ala Ser Arg Val Arg Val Ser Gly Gln Gly Leu His Glu
    610                 615                 620

Gly His Thr Phe Glu Pro Ala Glu Phe Ile Ile Asp Thr Arg Asp Ala
625                 630                 635                 640

Gly Tyr Gly Gly Leu Ser Leu Ser Ile Glu Gly Pro Ser Lys Val Asp
                645                 650                 655

Ile Asn Thr Glu Asp Leu Glu Asp Gly Thr Cys Arg Val Thr Tyr Cys
```

```
                    660                 665                 670
Pro Thr Glu Pro Gly Asn Tyr Ile Ile Asn Ile Lys Phe Ala Asp Gln
            675                 680                 685
His Val Pro Gly Ser Pro Phe Ser
        690                 695

<210> SEQ ID NO 36
<211> LENGTH: 2655
<212> TYPE: PRT
<213> ORGANISM: Homo sapiens
<220> FEATURE:
<221> NAME/KEY: misc_feature
<222> LOCATION: (1)..(2655)
<223> OTHER INFORMATION: Full length filamin A

<400> SEQUENCE: 36

Met Asp Tyr Lys Asp Asp Asp Lys Ser Ser His Ser Arg Ala
1               5                   10                  15

Gly Gln Ser Ala Ala Gly Ala Ala Pro Gly Gly Gly Val Asp Thr Arg
            20                  25                  30

Asp Ala Glu Met Pro Ala Thr Glu Lys Asp Leu Ala Glu Asp Ala Pro
        35                  40                  45

Trp Lys Lys Ile Gln Gln Asn Thr Phe Thr Arg Trp Cys Asn Glu His
    50                  55                  60

Leu Lys Cys Val Ser Lys Arg Ile Ala Asn Leu Gln Thr Asp Leu Ser
65                  70                  75                  80

Asp Gly Leu Arg Leu Ile Ala Leu Leu Glu Val Leu Ser Gln Lys Lys
                85                  90                  95

Met His Arg Lys His Asn Gln Arg Pro Thr Phe Arg Gln Met Gln Leu
            100                 105                 110

Glu Asn Val Ser Val Ala Leu Glu Phe Leu Asp Arg Glu Ser Ile Lys
        115                 120                 125

Leu Val Ser Ile Asp Ser Lys Ala Ile Val Asp Gly Asn Leu Lys Leu
    130                 135                 140

Ile Leu Gly Leu Ile Trp Thr Leu Ile Leu His Tyr Ser Ile Ser Met
145                 150                 155                 160

Pro Met Trp Asp Glu Glu Asp Glu Glu Ala Lys Lys Gln Thr Pro
                165                 170                 175

Lys Gln Arg Leu Leu Gly Trp Ile Gln Asn Lys Leu Pro Gln Leu Pro
            180                 185                 190

Ile Thr Asn Phe Ser Arg Asp Trp Gln Ser Gly Arg Ala Leu Gly Ala
        195                 200                 205

Leu Val Asp Ser Cys Ala Pro Gly Leu Cys Pro Asp Trp Asp Ser Trp
    210                 215                 220

Asp Ala Ser Lys Pro Val Thr Asn Ala Arg Glu Ala Met Gln Gln Ala
225                 230                 235                 240

Asp Asp Trp Leu Gly Ile Pro Gln Val Ile Thr Pro Glu Glu Ile Val
                245                 250                 255

Asp Pro Asn Val Asp Glu His Ser Val Met Thr Tyr Leu Ser Gln Phe
            260                 265                 270

Pro Lys Ala Lys Leu Lys Pro Gly Ala Pro Leu Arg Pro Lys Leu Asn
        275                 280                 285

Pro Lys Lys Ala Arg Ala Tyr Gly Pro Gly Ile Glu Pro Thr Gly Asn
    290                 295                 300

Met Val Lys Lys Arg Ala Glu Phe Thr Val Glu Thr Arg Ser Ala Gly
305                 310                 315                 320
```

```
Gln Gly Glu Val Leu Val Tyr Val Glu Asp Pro Ala Gly His Gln Glu
                325                 330                 335

Glu Ala Lys Val Thr Ala Asn Asn Asp Lys Asn Arg Thr Phe Ser Val
            340                 345                 350

Trp Tyr Val Pro Glu Val Thr Gly Thr His Lys Val Thr Val Leu Phe
        355                 360                 365

Ala Gly Gln His Ile Ala Lys Ser Pro Phe Glu Val Tyr Val Asp Lys
    370                 375                 380

Ser Gln Gly Asp Ala Ser Lys Val Thr Ala Gln Gly Pro Gly Leu Glu
385                 390                 395                 400

Pro Ser Gly Asn Ile Ala Asn Lys Thr Thr Tyr Phe Glu Ile Phe Thr
                405                 410                 415

Ala Gly Ala Gly Thr Gly Glu Val Glu Val Ile Gln Asp Pro Met
            420                 425                 430

Gly Gln Lys Gly Thr Val Glu Pro Gln Leu Glu Ala Arg Gly Asp Ser
        435                 440                 445

Thr Tyr Arg Cys Ser Tyr Gln Pro Thr Met Glu Gly Val His Thr Val
    450                 455                 460

His Val Thr Phe Ala Gly Val Pro Ile Pro Arg Ser Pro Tyr Thr Val
465                 470                 475                 480

Thr Val Gly Gln Ala Cys Asn Pro Ser Ala Cys Arg Ala Val Gly Arg
                485                 490                 495

Gly Leu Gln Pro Lys Gly Val Arg Val Lys Glu Thr Ala Asp Phe Lys
            500                 505                 510

Val Tyr Thr Lys Gly Ala Gly Ser Gly Glu Leu Lys Val Thr Val Lys
        515                 520                 525

Gly Pro Lys Gly Glu Glu Arg Val Lys Gln Lys Asp Leu Gly Asp Gly
    530                 535                 540

Val Tyr Gly Phe Glu Tyr Tyr Pro Met Val Pro Gly Thr Tyr Ile Val
545                 550                 555                 560

Thr Ile Thr Trp Gly Gly Gln Asn Ile Gly Arg Ser Pro Phe Glu Val
                565                 570                 575

Lys Val Gly Thr Glu Cys Gly Asn Gln Lys Val Arg Ala Trp Gly Pro
            580                 585                 590

Gly Leu Glu Gly Gly Val Val Gly Lys Ser Ala Asp Phe Val Val Glu
        595                 600                 605

Ala Ile Gly Asp Asp Val Gly Thr Leu Gly Phe Ser Val Glu Gly Pro
    610                 615                 620

Ser Gln Ala Lys Ile Glu Cys Asp Asp Lys Gly Asp Gly Ser Cys Asp
625                 630                 635                 640

Val Arg Tyr Trp Pro Gln Glu Ala Gly Glu Tyr Ala Val His Val Leu
                645                 650                 655

Cys Asn Ser Glu Asp Ile Arg Leu Ser Pro Phe Met Ala Asp Ile Arg
            660                 665                 670

Asp Ala Pro Gln Asp Phe His Pro Asp Arg Val Lys Ala Arg Gly Pro
        675                 680                 685

Gly Leu Glu Lys Thr Gly Val Ala Val Asn Lys Pro Ala Glu Phe Thr
    690                 695                 700

Val Asp Ala Lys His Gly Gly Lys Ala Pro Leu Arg Val Gln Val Gln
705                 710                 715                 720

Asp Asn Glu Gly Cys Pro Val Glu Ala Leu Val Lys Asp Asn Gly Asn
                725                 730                 735
```

```
Gly Thr Tyr Ser Cys Ser Tyr Val Pro Arg Lys Pro Val Lys His Thr
                740                 745                 750

Ala Met Val Ser Trp Gly Gly Val Ser Ile Pro Asn Ser Pro Phe Arg
                755                 760                 765

Val Asn Val Gly Ala Gly Ser His Pro Asn Lys Val Lys Val Tyr Gly
                770                 775                 780

Pro Gly Val Ala Lys Thr Gly Leu Lys Ala His Glu Pro Thr Tyr Phe
785                 790                 795                 800

Thr Val Asp Cys Ala Glu Ala Gly Gln Gly Asp Val Ser Ile Gly Ile
                    805                 810                 815

Lys Cys Ala Pro Gly Val Val Gly Pro Ala Glu Ala Asp Ile Asp Phe
                820                 825                 830

Asp Ile Ile Arg Asn Asp Asn Asp Thr Phe Thr Val Lys Tyr Thr Pro
                835                 840                 845

Arg Gly Ala Gly Ser Tyr Thr Ile Met Val Leu Phe Ala Asp Gln Ala
                850                 855                 860

Thr Pro Thr Ser Pro Ile Arg Val Lys Val Glu Pro Ser His Asp Ala
865                 870                 875                 880

Ser Lys Val Lys Ala Glu Gly Pro Gly Leu Ser Arg Thr Gly Val Glu
                    885                 890                 895

Leu Gly Lys Pro Thr His Phe Thr Val Asn Ala Lys Ala Ala Gly Lys
                    900                 905                 910

Gly Lys Leu Asp Val Gln Phe Ser Gly Leu Thr Lys Gly Asp Ala Val
                915                 920                 925

Arg Asp Val Asp Ile Ile Asp His His Asp Asn Thr Tyr Thr Val Lys
930                 935                 940

Tyr Thr Pro Val Gln Gln Gly Pro Val Gly Val Asn Val Thr Tyr Gly
945                 950                 955                 960

Gly Asp Pro Ile Pro Lys Ser Pro Phe Ser Val Ala Val Ser Pro Ser
                965                 970                 975

Leu Asp Leu Ser Lys Ile Lys Val Ser Gly Leu Gly Glu Lys Val Asp
                980                 985                 990

Val Gly Lys Asp Gln Glu Phe Thr  Val Lys Ser Lys Gly Ala Gly Gly
                995                 1000                1005

Gln Gly Lys Val Ala Ser Lys Ile Val Gly Pro Ser  Gly Ala Ala
    1010                1015                1020

Val Pro Cys Lys Val Glu Pro Gly Leu Gly Ala Asp  Asn Ser Val
    1025                1030                1035

Val Arg Phe Leu Pro Arg Glu Glu Gly Pro Tyr Glu  Val Glu Val
    1040                1045                1050

Thr Tyr Asp Gly Val Pro Val Pro Gly Ser Pro Phe  Pro Leu Glu
    1055                1060                1065

Ala Val Ala Pro Thr Lys Pro Ser Lys Val Lys Ala Phe Gly Pro
    1070                1075                1080

Gly Leu Gln Gly Gly Ser Ala Gly Ser Pro Ala Arg  Phe Thr Ile
    1085                1090                1095

Asp Thr Lys Gly Ala Gly Thr Gly Gly Leu Gly Leu  Thr Val Glu
    1100                1105                1110

Gly Pro Cys Glu Ala Gln Leu Glu Cys Leu Asp Asn  Gly Asp Gly
    1115                1120                1125

Thr Cys Ser Val Ser Tyr Val Pro Thr Glu Pro Gly  Asp Tyr Asn
    1130                1135                1140

Ile Asn Ile Leu Phe Ala Asp Thr His Ile Pro Gly  Ser Pro Phe
```

```
                    1145                1150                1155

Lys Ala His Val Val Pro Cys Phe Asp Ala Ser Lys Val Lys Cys
                1160                1165                1170

Ser Gly Pro Gly Leu Glu Arg Ala Thr Ala Gly Glu Val Gly Gln
                1175                1180                1185

Phe Gln Val Asp Cys Ser Ser Ala Gly Ser Ala Glu Leu Thr Ile
                1190                1195                1200

Glu Ile Cys Ser Glu Ala Gly Leu Pro Ala Glu Val Tyr Ile Gln
                1205                1210                1215

Asp His Gly Asp Gly Thr His Thr Ile Thr Tyr Ile Pro Leu Cys
                1220                1225                1230

Pro Gly Ala Tyr Thr Val Thr Ile Lys Tyr Gly Gly Gln Pro Val
                1235                1240                1245

Pro Asn Phe Pro Ser Lys Leu Gln Val Glu Pro Ala Val Asp Thr
                1250                1255                1260

Ser Gly Val Gln Cys Tyr Gly Pro Gly Ile Glu Gly Gln Gly Val
                1265                1270                1275

Phe Arg Glu Ala Thr Thr Glu Phe Ser Val Asp Ala Arg Ala Leu
                1280                1285                1290

Thr Gln Thr Gly Gly Pro His Val Lys Ala Arg Val Ala Asn Pro
                1295                1300                1305

Ser Gly Asn Leu Thr Glu Thr Tyr Val Gln Asp Arg Gly Asp Gly
                1310                1315                1320

Met Tyr Lys Val Glu Tyr Thr Pro Tyr Glu Glu Gly Leu His Ser
                1325                1330                1335

Val Asp Val Thr Tyr Asp Gly Ser Pro Val Pro Ser Ser Pro Phe
                1340                1345                1350

Gln Val Pro Val Thr Glu Gly Cys Asp Pro Ser Arg Val Arg Val
                1355                1360                1365

His Gly Pro Gly Ile Gln Ser Gly Thr Thr Asn Lys Pro Asn Lys
                1370                1375                1380

Phe Thr Val Glu Thr Arg Gly Ala Gly Thr Gly Gly Leu Gly Leu
                1385                1390                1395

Ala Val Glu Gly Pro Ser Glu Ala Lys Met Ser Cys Met Asp Asn
                1400                1405                1410

Lys Asp Gly Ser Cys Ser Val Glu Tyr Ile Pro Tyr Glu Ala Gly
                1415                1420                1425

Thr Tyr Ser Leu Asn Val Thr Tyr Gly Gly His Gln Val Pro Gly
                1430                1435                1440

Ser Pro Phe Lys Val Pro Val His Asp Val Thr Asp Ala Ser Lys
                1445                1450                1455

Val Lys Cys Ser Gly Pro Gly Leu Ser Pro Gly Met Val Arg Ala
                1460                1465                1470

Asn Leu Pro Gln Ser Phe Gln Val Asp Thr Ser Lys Ala Gly Val
                1475                1480                1485

Ala Pro Leu Gln Val Lys Val Gln Gly Pro Lys Gly Leu Val Glu
                1490                1495                1500

Pro Val Asp Val Val Asp Asn Ala Asp Gly Thr Gln Thr Val Asn
                1505                1510                1515

Tyr Val Pro Ser Arg Glu Gly Pro Tyr Ser Ile Ser Val Leu Tyr
                1520                1525                1530

Gly Asp Glu Glu Val Pro Arg Ser Pro Phe Lys Val Lys Val Leu
                1535                1540                1545
```

```
Pro Thr His Asp Ala Ser Lys Val Lys Ala Ser Gly Pro Gly Leu
    1550                1555                1560

Asn Thr Thr Gly Val Pro Ala Ser Leu Pro Val Glu Phe Thr Ile
    1565                1570                1575

Asp Ala Lys Asp Ala Gly Glu Gly Leu Leu Ala Val Gln Ile Thr
    1580                1585                1590

Asp Pro Glu Gly Lys Pro Lys Lys Thr His Ile Gln Asp Asn His
    1595                1600                1605

Asp Gly Thr Tyr Thr Val Ala Tyr Val Pro Asp Val Thr Gly Arg
    1610                1615                1620

Tyr Thr Ile Leu Ile Lys Tyr Gly Gly Asp Glu Ile Pro Phe Ser
    1625                1630                1635

Pro Tyr Arg Val Arg Ala Val Pro Thr Gly Asp Ala Ser Lys Cys
    1640                1645                1650

Thr Val Thr Val Ser Ile Gly Gly His Gly Leu Gly Ala Gly Ile
    1655                1660                1665

Gly Pro Thr Ile Gln Ile Gly Glu Glu Thr Val Ile Thr Val Asp
    1670                1675                1680

Thr Lys Ala Ala Gly Lys Gly Lys Val Thr Cys Thr Val Cys Thr
    1685                1690                1695

Pro Asp Gly Ser Glu Val Asp Val Asp Val Val Glu Asn Glu Asp
    1700                1705                1710

Gly Thr Phe Asp Ile Phe Tyr Thr Ala Pro Gln Pro Gly Lys Tyr
    1715                1720                1725

Val Ile Cys Val Arg Phe Gly Gly Glu His Val Pro Asn Ser Pro
    1730                1735                1740

Phe Gln Val Thr Ala Leu Ala Gly Asp Gln Pro Ser Val Gln Pro
    1745                1750                1755

Pro Leu Arg Ser Gln Gln Leu Ala Pro Gln Tyr Thr Tyr Ala Gln
    1760                1765                1770

Gly Gly Gln Gln Thr Trp Ala Pro Glu Arg Pro Leu Val Gly Val
    1775                1780                1785

Asn Gly Leu Asp Val Thr Ser Leu Arg Pro Phe Asp Leu Val Ile
    1790                1795                1800

Pro Phe Thr Ile Lys Lys Gly Glu Ile Thr Gly Glu Val Arg Met
    1805                1810                1815

Pro Ser Gly Lys Val Ala Gln Pro Thr Ile Thr Asp Asn Lys Asp
    1820                1825                1830

Gly Thr Val Thr Val Arg Tyr Ala Pro Ser Glu Ala Gly Leu His
    1835                1840                1845

Glu Met Asp Ile Arg Tyr Asp Asn Met His Ile Pro Gly Ser Pro
    1850                1855                1860

Leu Gln Phe Tyr Val Asp Tyr Val Asn Cys Gly His Val Thr Ala
    1865                1870                1875

Tyr Gly Pro Gly Leu Thr His Gly Val Val Asn Lys Pro Ala Thr
    1880                1885                1890

Phe Thr Val Asn Thr Lys Asp Ala Gly Glu Gly Gly Leu Ser Leu
    1895                1900                1905

Ala Ile Glu Gly Pro Ser Lys Ala Glu Ile Ser Cys Thr Asp Asn
    1910                1915                1920

Gln Asp Gly Thr Cys Ser Val Ser Tyr Leu Pro Val Leu Pro Gly
    1925                1930                1935
```

```
Asp Tyr Ser Ile Leu Val Lys Tyr Asn Glu Gln His Val Pro Gly
1940                1945                1950

Ser Pro Phe Thr Ala Arg Val Thr Gly Asp Asp Ser Met Arg Met
1955                1960                1965

Ser His Leu Lys Val Gly Ser Ala Ala Asp Ile Pro Ile Asn Ile
1970                1975                1980

Ser Glu Thr Asp Leu Ser Leu Leu Thr Ala Thr Val Val Pro Pro
1985                1990                1995

Ser Gly Arg Glu Glu Pro Cys Leu Leu Lys Arg Leu Arg Asn Gly
2000                2005                2010

His Val Gly Ile Ser Phe Val Pro Lys Glu Thr Gly Glu His Leu
2015                2020                2025

Val His Val Lys Lys Asn Gly Gln His Val Ala Ser Ser Pro Ile
2030                2035                2040

Pro Val Val Ile Ser Gln Ser Glu Ile Gly Asp Ala Ser Arg Val
2045                2050                2055

Arg Val Ser Gly Gln Gly Leu His Glu Gly His Thr Phe Glu Pro
2060                2065                2070

Ala Glu Phe Ile Ile Asp Thr Arg Asp Ala Gly Tyr Gly Gly Leu
2075                2080                2085

Ser Leu Ser Ile Glu Gly Pro Ser Lys Val Asp Ile Asn Thr Glu
2090                2095                2100

Asp Leu Glu Asp Gly Thr Cys Arg Val Thr Tyr Cys Pro Thr Glu
2105                2110                2115

Pro Gly Asn Tyr Ile Ile Asn Ile Lys Phe Ala Asp Gln His Val
2120                2125                2130

Pro Gly Ser Pro Phe Ser Val Lys Val Thr Gly Glu Gly Arg Val
2135                2140                2145

Lys Glu Ser Ile Thr Arg Arg Arg Arg Ala Pro Ser Val Ala Asn
2150                2155                2160

Val Gly Ser His Cys Asp Leu Ser Leu Lys Ile Pro Glu Ile Ser
2165                2170                2175

Ile Gln Asp Met Thr Ala Gln Val Thr Ser Pro Ser Gly Lys Thr
2180                2185                2190

His Glu Ala Glu Ile Val Glu Gly Glu Asn His Thr Tyr Cys Ile
2195                2200                2205

Arg Phe Val Pro Ala Glu Met Gly Thr His Thr Val Ser Val Lys
2210                2215                2220

Tyr Lys Gly Gln His Val Pro Gly Ser Pro Phe Gln Phe Thr Val
2225                2230                2235

Gly Pro Leu Gly Glu Gly Gly Ala His Lys Val Arg Ala Gly Gly
2240                2245                2250

Pro Gly Leu Glu Arg Ala Glu Ala Gly Val Pro Ala Glu Phe Ser
2255                2260                2265

Ile Trp Thr Arg Glu Ala Gly Ala Gly Gly Leu Ala Ile Ala Val
2270                2275                2280

Glu Gly Pro Ser Lys Ala Glu Ile Ser Phe Glu Asp Arg Lys Asp
2285                2290                2295

Gly Ser Cys Gly Val Ala Tyr Val Val Gln Glu Pro Gly Asp Tyr
2300                2305                2310

Glu Val Ser Val Lys Phe Asn Glu Glu His Ile Pro Asp Ser Pro
2315                2320                2325

Phe Val Val Pro Val Ala Ser Pro Ser Gly Asp Ala Arg Arg Leu
```

```
              2330                2335                2340

Thr Val Ser Ser Leu Gln Glu Ser Gly Leu Lys Val Asn Gln Pro
        2345                2350                2355

Ala Ser Phe Ala Val Ser Leu Asn Gly Ala Lys Gly Ala Ile Asp
        2360                2365                2370

Ala Lys Val His Ser Pro Ser Gly Ala Leu Glu Glu Cys Tyr Val
        2375                2380                2385

Thr Glu Ile Asp Gln Asp Lys Tyr Ala Val Arg Phe Ile Pro Arg
        2390                2395                2400

Glu Asn Gly Val Tyr Leu Ile Asp Val Lys Phe Asn Gly Thr His
        2405                2410                2415

Ile Pro Gly Ser Pro Phe Lys Ile Arg Val Gly Glu Pro Gly His
        2420                2425                2430

Gly Gly Asp Pro Gly Leu Val Ser Ala Tyr Gly Ala Gly Leu Glu
        2435                2440                2445

Gly Gly Val Thr Gly Asn Pro Ala Glu Phe Val Val Asn Thr Ser
        2450                2455                2460

Asn Ala Gly Ala Gly Ala Leu Ser Val Thr Ile Asp Gly Pro Ser
        2465                2470                2475

Lys Val Lys Met Asp Cys Gln Glu Cys Pro Glu Gly Tyr Arg Val
        2480                2485                2490

Thr Tyr Thr Pro Met Ala Pro Gly Ser Tyr Leu Ile Ser Ile Lys
        2495                2500                2505

Tyr Gly Gly Pro Tyr His Ile Gly Gly Ser Pro Phe Lys Ala Lys
        2510                2515                2520

Val Thr Gly Pro Arg Leu Val Ser Asn His Ser Leu His Glu Thr
        2525                2530                2535

Ser Ser Val Phe Val Asp Ser Leu Thr Lys Ala Thr Cys Ala Pro
        2540                2545                2550

Gln His Gly Ala Pro Gly Pro Gly Pro Ala Asp Ala Ser Lys Val
        2555                2560                2565

Val Ala Lys Gly Leu Gly Leu Ser Lys Ala Tyr Val Gly Gln Lys
        2570                2575                2580

Ser Ser Phe Thr Val Asp Cys Ser Lys Ala Gly Asn Asn Met Leu
        2585                2590                2595

Leu Val Gly Val His Gly Pro Arg Thr Pro Cys Glu Glu Ile Leu
        2600                2605                2610

Val Lys His Val Gly Ser Arg Leu Tyr Ser Val Ser Tyr Leu Leu
        2615                2620                2625

Lys Asp Lys Gly Glu Tyr Thr Leu Val Val Lys Trp Gly Asp Glu
        2630                2635                2640

His Ile Pro Gly Ser Pro Tyr Arg Val Val Val Pro
        2645                2650                2655

<210> SEQ ID NO 37
<211> LENGTH: 681
<212> TYPE: PRT
<213> ORGANISM: Homo sapiens
<220> FEATURE:
<221> NAME/KEY: misc_feature
<222> LOCATION: (1)..(681)
<223> OTHER INFORMATION: Partial filamin B (aa1416-2089)

<400> SEQUENCE: 37

Met His His His His His Lys Asp Val Val Asp Pro Ser Lys Val
1               5                   10                  15
```

```
Lys Ile Ala Gly Pro Gly Leu Gly Ser Gly Val Arg Ala Arg Val Leu
             20                  25                  30

Gln Ser Phe Thr Val Asp Ser Lys Ala Gly Leu Ala Pro Leu Glu
         35                  40                  45

Val Arg Val Leu Gly Pro Arg Gly Leu Val Glu Pro Val Asn Val Val
 50                  55                  60

Asp Asn Gly Asp Gly Thr His Thr Val Thr Tyr Thr Pro Ser Gln Glu
 65                  70                  75                  80

Gly Pro Tyr Met Val Ser Val Lys Tyr Ala Asp Glu Glu Ile Pro Arg
                 85                  90                  95

Ser Pro Phe Lys Val Lys Val Leu Pro Thr Tyr Asp Ala Ser Lys Val
             100                 105                 110

Thr Ala Ser Gly Pro Gly Leu Ser Ser Tyr Gly Val Pro Ala Ser Leu
         115                 120                 125

Pro Val Asp Phe Ala Ile Asp Ala Arg Asp Ala Gly Glu Gly Leu Leu
130                 135                 140

Ala Val Gln Ile Thr Asp Gln Glu Gly Lys Pro Lys Arg Ala Ile Val
145                 150                 155                 160

His Asp Asn Lys Asp Gly Thr Tyr Ala Val Thr Tyr Ile Pro Asp Lys
                 165                 170                 175

Thr Gly Arg Tyr Met Ile Gly Val Thr Tyr Gly Gly Asp Asp Ile Pro
             180                 185                 190

Leu Ser Pro Tyr Arg Ile Arg Ala Thr Gln Thr Gly Asp Ala Ser Lys
         195                 200                 205

Cys Leu Ala Thr Gly Pro Gly Ile Ala Ser Thr Val Lys Thr Gly Glu
         210                 215                 220

Glu Val Gly Phe Val Val Asp Ala Lys Thr Ala Gly Lys Gly Lys Val
225                 230                 235                 240

Thr Cys Thr Val Leu Thr Pro Asp Gly Thr Glu Ala Glu Ala Asp Val
                 245                 250                 255

Ile Glu Asn Glu Asp Gly Thr Tyr Asp Ile Phe Tyr Thr Ala Ala Lys
             260                 265                 270

Pro Gly Thr Tyr Val Ile Tyr Val Arg Phe Gly Gly Val Asp Ile Pro
         275                 280                 285

Asn Ser Pro Phe Thr Val Met Ala Thr Asp Gly Glu Val Thr Ala Val
290                 295                 300

Glu Glu Ala Pro Val Asn Ala Cys Pro Pro Gly Phe Arg Pro Trp Val
305                 310                 315                 320

Thr Glu Glu Ala Tyr Val Pro Val Ser Asp Met Asn Gly Leu Gly Phe
                 325                 330                 335

Lys Pro Phe Asp Leu Val Ile Pro Phe Ala Val Arg Lys Gly Glu Ile
             340                 345                 350

Thr Gly Glu Val His Met Pro Ser Gly Lys Thr Ala Thr Pro Glu Ile
         355                 360                 365

Val Asp Asn Lys Asp Gly Thr Val Thr Val Arg Tyr Ala Pro Thr Glu
370                 375                 380

Val Gly Leu His Glu Met His Ile Lys Tyr Met Gly Ser His Ile Pro
385                 390                 395                 400

Glu Ser Pro Leu Gln Phe Tyr Val Asn Tyr Pro Asn Ser Gly Ser Val
                 405                 410                 415

Ser Ala Tyr Gly Pro Gly Leu Val Tyr Gly Val Ala Asn Lys Thr Ala
             420                 425                 430
```

```
Thr Phe Thr Ile Val Thr Glu Asp Ala Gly Glu Gly Leu Asp Leu
            435                 440                 445

Ala Ile Glu Gly Pro Ser Lys Ala Glu Ile Ser Cys Ile Asp Asn Lys
450                 455                 460

Asp Gly Thr Cys Thr Val Thr Tyr Leu Pro Thr Leu Pro Gly Asp Tyr
465                 470                 475                 480

Ser Ile Leu Val Lys Tyr Asn Asp Lys His Ile Pro Gly Ser Pro Phe
                485                 490                 495

Thr Ala Lys Ile Thr Asp Asp Ser Arg Arg Cys Ser Gln Val Lys Leu
                500                 505                 510

Gly Ser Ala Ala Asp Phe Leu Leu Asp Ile Ser Glu Thr Asp Leu Ser
            515                 520                 525

Ser Leu Thr Ala Ser Ile Lys Ala Pro Ser Gly Arg Asp Glu Pro Cys
530                 535                 540

Leu Leu Lys Arg Leu Pro Asn Asn His Ile Gly Ile Ser Phe Ile Pro
545                 550                 555                 560

Arg Glu Val Gly Glu His Leu Val Ser Ile Lys Lys Asn Gly Asn His
                565                 570                 575

Val Ala Asn Ser Pro Val Ser Ile Met Val Val Gln Ser Glu Ile Gly
            580                 585                 590

Asp Ala Arg Arg Ala Lys Val Tyr Gly Arg Gly Leu Ser Glu Gly Arg
595                 600                 605

Thr Phe Glu Met Ser Asp Phe Ile Val Asp Thr Arg Asp Ala Gly Tyr
            610                 615                 620

Gly Gly Ile Ser Leu Ala Val Glu Gly Pro Ser Lys Val Asp Ile Gln
625                 630                 635                 640

Thr Glu Asp Leu Glu Asp Gly Thr Cys Lys Val Ser Tyr Phe Pro Thr
                645                 650                 655

Val Pro Gly Val Tyr Ile Val Ser Thr Lys Phe Ala Asp Glu His Val
            660                 665                 670

Pro Gly Ser Pro Phe Thr Val Lys Ile
                675                 680

<210> SEQ ID NO 38
<211> LENGTH: 698
<212> TYPE: PRT
<213> ORGANISM: Homo sapiens
<220> FEATURE:
<221> NAME/KEY: misc_feature
<222> LOCATION: (1)..(698)
<223> OTHER INFORMATION: Partial filamin C (aa 1438-2128)

<400> SEQUENCE: 38

Met His His His His His Lys Asp Val Asp Pro Gly Lys Val
1               5                   10                  15

Lys Cys Ser Gly Pro Gly Leu Gly Ala Gly Val Arg Ala Arg Val Pro
                20                  25                  30

Gln Thr Phe Thr Val Asp Cys Ser Gln Ala Gly Arg Ala Pro Leu Gln
            35                  40                  45

Val Ala Val Leu Gly Pro Thr Gly Val Ala Glu Pro Val Glu Val Arg
50                  55                  60

Asp Asn Gly Asp Gly Thr His Thr Val His Tyr Thr Pro Ala Thr Asp
65                  70                  75                  80

Gly Pro Tyr Thr Val Ala Val Lys Tyr Ala Asp Gln Glu Val Pro Arg
                85                  90                  95

Ser Pro Phe Lys Ile Lys Val Leu Pro Ala His Asp Ala Ser Lys Val
```

```
                100             105             110
Arg Ala Ser Gly Pro Gly Leu Asn Ala Ser Gly Ile Pro Ala Ser Leu
            115                 120                 125

Pro Val Glu Phe Thr Ile Asp Ala Arg Asp Ala Gly Glu Gly Leu Leu
            130                 135                 140

Thr Val Gln Ile Leu Asp Pro Glu Gly Lys Pro Lys Lys Ala Asn Ile
145                 150                 155                 160

Arg Asp Asn Gly Asp Gly Thr Tyr Thr Val Ser Tyr Leu Pro Asp Met
                165                 170                 175

Ser Gly Arg Tyr Thr Ile Thr Ile Lys Tyr Gly Gly Asp Glu Ile Pro
            180                 185                 190

Tyr Ser Pro Phe Arg Ile His Ala Leu Pro Thr Gly Asp Ala Ser Lys
            195                 200                 205

Cys Leu Val Thr Val Ser Ile Gly Gly His Gly Leu Gly Ala Cys Leu
210                 215                 220

Gly Pro Arg Ile Gln Ile Gly Gln Glu Thr Val Ile Thr Val Asp Ala
225                 230                 235                 240

Lys Ala Ala Gly Glu Gly Lys Val Thr Cys Thr Val Ser Thr Pro Asp
                245                 250                 255

Gly Ala Glu Leu Asp Val Asp Val Val Glu Asn His Asp Gly Thr Phe
                260                 265                 270

Asp Ile Tyr Tyr Thr Ala Pro Glu Pro Gly Lys Tyr Val Ile Thr Ile
            275                 280                 285

Arg Phe Gly Gly Glu His Ile Pro Asn Ser Pro Phe His Val Leu Ala
            290                 295                 300

Cys Asp Pro Leu Pro His Glu Glu Pro Ser Glu Val Pro Gln Leu
305                 310                 315                 320

Arg Gln Pro Tyr Ala Pro Pro Arg Pro Gly Ala Arg Pro Thr His Trp
                325                 330                 335

Ala Thr Glu Glu Pro Val Val Pro Val Glu Pro Met Glu Ser Met Leu
                340                 345                 350

Arg Pro Phe Asn Leu Val Ile Pro Phe Ala Val Gln Lys Gly Glu Leu
            355                 360                 365

Thr Gly Glu Val Arg Met Pro Ser Gly Lys Thr Ala Arg Pro Asn Ile
            370                 375                 380

Thr Asp Asn Lys Asp Gly Thr Ile Thr Val Arg Tyr Ala Pro Thr Glu
385                 390                 395                 400

Lys Gly Leu His Gln Met Gly Ile Lys Tyr Asp Gly Asn His Ile Pro
                405                 410                 415

Gly Ser Pro Leu Gln Phe Tyr Val Asp Ala Ile Asn Ser Arg His Val
            420                 425                 430

Ser Ala Tyr Gly Pro Gly Leu Ser His Gly Met Val Asn Lys Pro Ala
            435                 440                 445

Thr Phe Thr Ile Val Thr Lys Asp Ala Gly Glu Gly Gly Leu Ser Leu
            450                 455                 460

Ala Val Glu Gly Pro Ser Lys Ala Glu Ile Thr Cys Lys Asp Asn Lys
465                 470                 475                 480

Asp Gly Thr Cys Thr Val Ser Tyr Leu Pro Thr Ala Pro Gly Asp Tyr
                485                 490                 495

Ser Ile Ile Val Arg Phe Asp Asp Lys His Ile Pro Gly Ser Pro Phe
            500                 505                 510

Thr Ala Lys Ile Thr Gly Asp Asp Ser Met Arg Thr Ser Gln Leu Asn
            515                 520                 525
```

```
Val Gly Thr Ser Thr Asp Val Ser Leu Lys Ile Thr Glu Ser Asp Leu
        530                 535                 540

Ser Gln Leu Thr Ala Ser Ile Arg Ala Pro Ser Gly Asn Glu Glu Pro
545                 550                 555                 560

Cys Leu Leu Lys Arg Leu Pro Asn Arg His Ile Gly Ile Ser Phe Thr
                565                 570                 575

Pro Lys Glu Val Gly Glu His Val Val Ser Val Arg Lys Ser Gly Lys
            580                 585                 590

His Val Thr Asn Ser Pro Phe Lys Ile Leu Val Gly Pro Ser Glu Ile
        595                 600                 605

Gly Asp Ala Ser Lys Val Arg Val Trp Gly Lys Gly Leu Ser Glu Gly
610                 615                 620

His Thr Phe Gln Val Ala Glu Phe Ile Val Asp Thr Arg Asn Ala Gly
625                 630                 635                 640

Tyr Gly Gly Leu Gly Leu Ser Ile Glu Gly Pro Ser Lys Val Asp Ile
                645                 650                 655

Asn Cys Glu Asp Met Glu Asp Gly Thr Cys Lys Val Thr Tyr Cys Pro
                660                 665                 670

Thr Glu Pro Gly Thr Tyr Ile Ile Asn Ile Lys Phe Ala Asp Lys His
            675                 680                 685

Val Pro Gly Ser Pro Phe Thr Val Lys Val
690                 695
```

<210> SEQ ID NO 39
<211> LENGTH: 2609
<212> TYPE: PRT
<213> ORGANISM: Homo sapiens
<220> FEATURE:
<221> NAME/KEY: misc_feature
<222> LOCATION: (1)..(2609)
<223> OTHER INFORMATION: Full length filamin B

<400> SEQUENCE: 39

```
Met Asp Tyr Lys Asp Asp Asp Lys Pro Val Thr Glu Lys Asp Leu
1               5                   10                  15

Ala Glu Asp Ala Pro Trp Lys Lys Ile Gln Gln Asn Thr Phe Thr Arg
            20                  25                  30

Trp Cys Asn Glu His Leu Lys Cys Val Asn Lys Arg Ile Gly Asn Leu
                35                  40                  45

Gln Thr Asp Leu Ser Asp Gly Leu Arg Leu Ile Ala Leu Leu Glu Val
        50                  55                  60

Leu Ser Gln Lys Arg Met Tyr Arg Lys Tyr His Gln Arg Pro Thr Phe
65                  70                  75                  80

Arg Gln Met Gln Leu Glu Asn Val Ser Val Ala Leu Glu Phe Leu Asp
                85                  90                  95

Arg Glu Ser Ile Lys Leu Val Ser Ile Asp Ser Lys Ala Ile Val Asp
            100                 105                 110

Gly Asn Leu Lys Leu Ile Leu Gly Leu Val Trp Thr Leu Ile Leu His
        115                 120                 125

Tyr Ser Ile Ser Met Pro Val Trp Glu Asp Glu Gly Asp Asp Asp Ala
130                 135                 140

Lys Lys Gln Thr Pro Lys Gln Arg Leu Leu Gly Trp Ile Gln Asn Lys
145                 150                 155                 160

Ile Pro Tyr Leu Pro Ile Thr Asn Phe Asn Gln Asn Trp Gln Asp Gly
                165                 170                 175
```

```
Lys Ala Leu Gly Ala Leu Val Asp Ser Cys Ala Pro Gly Leu Cys Pro
                180                 185                 190

Asp Trp Glu Ser Trp Asp Pro Gln Lys Pro Val Asp Asn Ala Arg Glu
            195                 200                 205

Ala Met Gln Gln Ala Asp Asp Trp Leu Gly Val Pro Gln Val Ile Thr
        210                 215                 220

Pro Glu Glu Ile Ile His Pro Asp Val Asp Glu His Ser Val Met Thr
225                 230                 235                 240

Tyr Leu Ser Gln Phe Pro Lys Ala Lys Leu Lys Pro Gly Ala Pro Leu
                245                 250                 255

Lys Pro Lys Leu Asn Pro Lys Lys Ala Arg Ala Tyr Gly Arg Gly Ile
            260                 265                 270

Glu Pro Thr Gly Asn Met Val Lys Gln Pro Ala Lys Phe Thr Val Asp
        275                 280                 285

Thr Ile Ser Ala Gly Gln Gly Asp Val Met Val Phe Val Glu Asp Pro
290                 295                 300

Glu Gly Asn Lys Glu Ala Gln Val Thr Pro Asp Ser Asp Lys Asn
305                 310                 315                 320

Lys Thr Tyr Ser Val Glu Tyr Leu Pro Lys Val Thr Gly Leu His Lys
                325                 330                 335

Val Thr Val Leu Phe Ala Gly Gln His Ile Ser Lys Ser Pro Phe Glu
            340                 345                 350

Val Ser Val Asp Lys Ala Gln Gly Asp Ala Ser Lys Val Thr Ala Lys
        355                 360                 365

Gly Pro Gly Leu Glu Ala Val Gly Asn Ile Ala Asn Lys Pro Thr Tyr
370                 375                 380

Phe Asp Ile Tyr Thr Ala Gly Ala Gly Val Gly Asp Ile Gly Val Glu
385                 390                 395                 400

Val Glu Asp Pro Gln Gly Lys Asn Thr Val Glu Leu Leu Val Glu Asp
                405                 410                 415

Lys Gly Asn Gln Val Tyr Arg Cys Val Tyr Lys Pro Met Gln Pro Gly
            420                 425                 430

Pro His Val Val Lys Ile Phe Phe Ala Gly Asp Thr Ile Pro Lys Ser
        435                 440                 445

Pro Phe Val Val Gln Val Gly Glu Ala Cys Asn Pro Asn Ala Cys Arg
450                 455                 460

Ala Ser Gly Arg Gly Leu Gln Pro Lys Gly Val Arg Ile Arg Glu Thr
465                 470                 475                 480

Thr Asp Phe Lys Val Asp Thr Lys Ala Ala Gly Ser Gly Glu Leu Gly
                485                 490                 495

Val Thr Met Lys Gly Pro Lys Gly Leu Glu Glu Leu Val Lys Gln Lys
            500                 505                 510

Asp Phe Leu Asp Gly Val Tyr Ala Phe Glu Tyr Tyr Pro Ser Thr Pro
        515                 520                 525

Gly Arg Tyr Ser Ile Ala Ile Thr Trp Gly Gly His His Ile Pro Lys
530                 535                 540

Ser Pro Phe Glu Val Gln Val Gly Pro Glu Ala Gly Met Gln Lys Val
545                 550                 555                 560

Arg Ala Trp Gly Pro Gly Leu His Gly Gly Ile Val Gly Arg Ser Ala
                565                 570                 575

Asp Phe Val Val Glu Ser Ile Gly Ser Glu Val Gly Ser Leu Gly Phe
            580                 585                 590

Ala Ile Glu Gly Pro Ser Gln Ala Lys Ile Glu Tyr Asn Asp Gln Asn
```

```
                 595                 600                 605
Asp Gly Ser Cys Asp Val Lys Tyr Trp Pro Lys Glu Pro Gly Glu Tyr
    610                 615                 620

Ala Val His Ile Met Cys Asp Glu Asp Ile Lys Asp Ser Pro Tyr
625                 630                 635                 640

Met Ala Phe Ile His Pro Ala Thr Gly Gly Tyr Asn Pro Asp Leu Val
                645                 650                 655

Arg Ala Tyr Gly Pro Gly Leu Glu Lys Ser Gly Cys Ile Val Asn Asn
            660                 665                 670

Leu Ala Glu Phe Thr Val Asp Pro Lys Asp Ala Gly Lys Ala Pro Leu
        675                 680                 685

Lys Ile Phe Ala Gln Asp Gly Glu Gly Gln Arg Ile Asp Ile Gln Met
690                 695                 700

Lys Asn Arg Met Asp Gly Thr Tyr Ala Cys Ser Tyr Thr Pro Val Lys
705                 710                 715                 720

Ala Ile Lys His Thr Ile Ala Val Val Trp Gly Gly Val Asn Ile Pro
                725                 730                 735

His Ser Pro Tyr Arg Val Asn Ile Gly Gln Gly Ser His Pro Gln Lys
            740                 745                 750

Val Lys Val Phe Gly Pro Gly Val Glu Arg Ser Gly Leu Lys Ala Asn
        755                 760                 765

Glu Pro Thr His Phe Thr Val Asp Cys Thr Glu Ala Gly Glu Gly Asp
770                 775                 780

Val Ser Val Gly Ile Lys Cys Asp Ala Arg Val Leu Ser Glu Asp Glu
785                 790                 795                 800

Glu Asp Val Asp Phe Asp Ile Ile His Asn Ala Asn Asp Thr Phe Thr
                805                 810                 815

Val Lys Tyr Val Pro Pro Ala Ala Gly Arg Tyr Thr Ile Lys Val Leu
            820                 825                 830

Phe Ala Ser Gln Glu Ile Pro Ala Ser Pro Phe Arg Val Lys Val Asp
        835                 840                 845

Pro Ser His Asp Ala Ser Lys Val Lys Ala Glu Gly Pro Gly Leu Ser
850                 855                 860

Lys Ala Gly Val Glu Asn Gly Lys Pro Thr His Phe Thr Val Tyr Thr
865                 870                 875                 880

Lys Gly Ala Gly Lys Ala Pro Leu Asn Val Gln Phe Asn Ser Pro Leu
                885                 890                 895

Pro Gly Asp Ala Val Lys Asp Leu Asp Ile Ile Asp Asn Tyr Asp Tyr
            900                 905                 910

Ser His Thr Val Lys Tyr Thr Pro Thr Gln Gln Gly Asn Met Gln Val
        915                 920                 925

Leu Val Thr Tyr Gly Gly Asp Pro Ile Pro Lys Ser Pro Phe Thr Val
930                 935                 940

Gly Val Ala Ala Pro Leu Asp Leu Ser Lys Ile Lys Leu Asn Gly Leu
945                 950                 955                 960

Glu Asn Arg Val Glu Val Gly Lys Asp Gln Glu Phe Thr Val Asp Thr
                965                 970                 975

Arg Gly Ala Gly Gly Gln Gly Lys Leu Asp Val Thr Ile Leu Ser Pro
            980                 985                 990

Ser Arg Lys Val Val Pro Cys Leu Val Thr Pro Val Thr Gly Arg Glu
        995                 1000                1005

Asn Ser Thr Ala Lys Phe Ile Pro Arg Glu Glu Gly Leu Tyr Ala
    1010                1015                1020
```

-continued

```
Val Asp Val Thr Tyr Asp Gly His Pro Val Pro Gly Ser Pro Tyr
   1025              1030              1035

Thr Val Glu Ala Ser Leu Pro Pro Asp Pro Ser Lys Val Lys Ala
   1040              1045              1050

His Gly Pro Gly Leu Glu Gly Gly Leu Val Gly Lys Pro Ala Glu
   1055              1060              1065

Phe Thr Ile Asp Thr Lys Gly Ala Gly Thr Gly Leu Gly Leu
   1070              1075              1080

Thr Val Glu Gly Pro Cys Glu Ala Lys Ile Glu Cys Ser Asp Asn
   1085              1090              1095

Gly Asp Gly Thr Cys Ser Val Ser Tyr Leu Pro Thr Lys Pro Gly
   1100              1105              1110

Glu Tyr Phe Val Asn Ile Leu Phe Glu Glu Val His Ile Pro Gly
   1115              1120              1125

Ser Pro Phe Lys Ala Asp Ile Glu Met Pro Phe Asp Pro Ser Lys
   1130              1135              1140

Val Val Ala Ser Gly Pro Gly Leu Glu His Gly Lys Val Gly Glu
   1145              1150              1155

Ala Gly Leu Leu Ser Val Asp Cys Ser Glu Ala Gly Pro Gly Ala
   1160              1165              1170

Leu Gly Leu Glu Ala Val Ser Asp Ser Gly Thr Lys Ala Glu Val
   1175              1180              1185

Ser Ile Gln Asn Asn Lys Asp Gly Thr Tyr Ala Val Thr Tyr Val
   1190              1195              1200

Pro Leu Thr Ala Gly Met Tyr Thr Leu Thr Met Lys Tyr Gly Gly
   1205              1210              1215

Glu Leu Val Pro His Phe Pro Ala Arg Val Lys Val Glu Pro Ala
   1220              1225              1230

Val Asp Thr Ser Arg Ile Lys Val Phe Gly Pro Gly Ile Glu Gly
   1235              1240              1245

Lys Asp Val Phe Arg Glu Ala Thr Thr Asp Phe Thr Val Asp Ser
   1250              1255              1260

Arg Pro Leu Thr Gln Val Gly Gly Asp His Ile Lys Ala His Ile
   1265              1270              1275

Ala Asn Pro Ser Gly Ala Ser Thr Glu Cys Phe Val Thr Asp Asn
   1280              1285              1290

Ala Asp Gly Thr Tyr Gln Val Glu Tyr Thr Pro Phe Glu Lys Gly
   1295              1300              1305

Leu His Val Val Glu Val Thr Tyr Asp Asp Val Pro Ile Pro Asn
   1310              1315              1320

Ser Pro Phe Lys Val Ala Val Thr Glu Gly Cys Gln Pro Ser Arg
   1325              1330              1335

Val Gln Ala Gln Gly Pro Gly Leu Lys Glu Ala Phe Thr Asn Lys
   1340              1345              1350

Pro Asn Val Phe Thr Val Val Thr Arg Gly Ala Gly Ile Gly Gly
   1355              1360              1365

Leu Gly Ile Thr Val Glu Gly Pro Ser Glu Ser Lys Ile Asn Cys
   1370              1375              1380

Arg Asp Asn Lys Asp Gly Ser Cys Ser Ala Glu Tyr Ile Pro Phe
   1385              1390              1395

Ala Pro Gly Asp Tyr Asp Val Asn Ile Thr Tyr Gly Gly Ala His
   1400              1405              1410
```

```
Ile Pro Gly Ser Pro Phe Arg Val Pro Val Lys Asp Val Val Asp
1415                1420                1425

Pro Ser Lys Val Lys Ile Ala Gly Pro Gly Leu Gly Ser Gly Val
1430                1435                1440

Arg Ala Arg Val Leu Gln Ser Phe Thr Val Asp Ser Ser Lys Ala
1445                1450                1455

Gly Leu Ala Pro Leu Glu Val Arg Val Leu Gly Pro Arg Gly Leu
1460                1465                1470

Val Glu Pro Val Asn Val Val Asp Asn Gly Asp Gly Thr His Thr
1475                1480                1485

Val Thr Tyr Thr Pro Ser Gln Glu Gly Pro Tyr Met Val Ser Val
1490                1495                1500

Lys Tyr Ala Asp Glu Glu Ile Pro Arg Ser Pro Phe Lys Val Lys
1505                1510                1515

Val Leu Pro Thr Tyr Asp Ala Ser Lys Val Thr Ala Ser Gly Pro
1520                1525                1530

Gly Leu Ser Ser Tyr Gly Val Pro Ala Ser Leu Pro Val Asp Phe
1535                1540                1545

Ala Ile Asp Ala Arg Asp Ala Gly Glu Gly Leu Leu Ala Val Gln
1550                1555                1560

Ile Thr Asp Gln Glu Gly Lys Pro Lys Arg Ala Ile Val His Asp
1565                1570                1575

Asn Lys Asp Gly Thr Tyr Ala Val Thr Tyr Ile Pro Asp Lys Thr
1580                1585                1590

Gly Arg Tyr Met Ile Gly Val Thr Tyr Gly Gly Asp Asp Ile Pro
1595                1600                1605

Leu Ser Pro Tyr Arg Ile Arg Ala Thr Gln Thr Gly Asp Ala Ser
1610                1615                1620

Lys Cys Leu Ala Thr Gly Pro Gly Ile Ala Ser Thr Val Lys Thr
1625                1630                1635

Gly Glu Glu Val Gly Phe Val Val Asp Ala Lys Thr Ala Gly Lys
1640                1645                1650

Gly Lys Val Thr Cys Thr Val Leu Thr Pro Asp Gly Thr Glu Ala
1655                1660                1665

Glu Ala Asp Val Ile Glu Asn Glu Asp Gly Thr Tyr Asp Ile Phe
1670                1675                1680

Tyr Thr Ala Ala Lys Pro Gly Thr Tyr Val Ile Tyr Val Arg Phe
1685                1690                1695

Gly Gly Val Asp Ile Pro Asn Ser Pro Phe Thr Val Met Ala Thr
1700                1705                1710

Asp Gly Glu Val Thr Ala Val Glu Glu Ala Pro Val Asn Ala Cys
1715                1720                1725

Pro Pro Gly Phe Arg Pro Trp Val Thr Glu Glu Ala Tyr Val Pro
1730                1735                1740

Val Ser Asp Met Asn Gly Leu Gly Phe Lys Pro Phe Asp Leu Val
1745                1750                1755

Ile Pro Phe Ala Val Arg Lys Gly Glu Ile Thr Gly Glu Val His
1760                1765                1770

Met Pro Ser Gly Lys Thr Ala Thr Pro Glu Ile Val Asp Asn Lys
1775                1780                1785

Asp Gly Thr Val Thr Val Arg Tyr Ala Pro Thr Glu Val Gly Leu
1790                1795                1800

His Glu Met His Ile Lys Tyr Met Gly Ser His Ile Pro Glu Ser
```

```
        1805                1810                1815

Pro Leu Gln Phe Tyr Val Asn Tyr Pro Asn Ser Gly Ser Val Ser
        1820                1825                1830

Ala Tyr Gly Pro Gly Leu Val Tyr Gly Val Ala Asn Lys Thr Ala
        1835                1840                1845

Thr Phe Thr Ile Val Thr Glu Asp Ala Gly Glu Gly Gly Leu Asp
        1850                1855                1860

Leu Ala Ile Glu Gly Pro Ser Lys Ala Glu Ile Ser Cys Ile Asp
        1865                1870                1875

Asn Lys Asp Gly Thr Cys Thr Val Thr Tyr Leu Pro Thr Leu Pro
        1880                1885                1890

Gly Asp Tyr Ser Ile Leu Val Lys Tyr Asn Asp Lys His Ile Pro
        1895                1900                1905

Gly Ser Pro Phe Thr Ala Lys Ile Thr Asp Ser Arg Arg Cys
        1910                1915                1920

Ser Gln Val Lys Leu Gly Ser Ala Ala Asp Phe Leu Leu Asp Ile
        1925                1930                1935

Ser Glu Thr Asp Leu Ser Ser Leu Thr Ala Ser Ile Lys Ala Pro
        1940                1945                1950

Ser Gly Arg Asp Glu Pro Cys Leu Leu Lys Arg Leu Pro Asn Asn
        1955                1960                1965

His Ile Gly Ile Ser Phe Ile Pro Arg Glu Val Gly Glu His Leu
        1970                1975                1980

Val Ser Ile Lys Lys Asn Gly Asn His Val Ala Asn Ser Pro Val
        1985                1990                1995

Ser Ile Met Val Val Gln Ser Glu Ile Gly Asp Ala Arg Arg Ala
        2000                2005                2010

Lys Val Tyr Gly Arg Gly Leu Ser Glu Gly Arg Thr Phe Glu Met
        2015                2020                2025

Ser Asp Phe Ile Val Asp Thr Arg Asp Ala Gly Tyr Gly Gly Ile
        2030                2035                2040

Ser Leu Ala Val Glu Gly Pro Ser Lys Val Asp Ile Gln Thr Glu
        2045                2050                2055

Asp Leu Glu Asp Gly Thr Cys Lys Val Ser Tyr Phe Pro Thr Val
        2060                2065                2070

Pro Gly Val Tyr Ile Val Ser Thr Lys Phe Ala Asp Glu His Val
        2075                2080                2085

Pro Gly Ser Pro Phe Thr Val Lys Ile Ser Gly Glu Gly Arg Val
        2090                2095                2100

Lys Glu Ser Ile Thr Arg Thr Ser Arg Ala Pro Ser Val Ala Thr
        2105                2110                2115

Val Gly Ser Ile Cys Asp Leu Asn Leu Lys Ile Pro Glu Ile Asn
        2120                2125                2130

Ser Ser Asp Met Ser Ala His Val Thr Ser Pro Ser Gly Arg Val
        2135                2140                2145

Thr Glu Ala Glu Ile Val Pro Met Gly Lys Asn Ser His Cys Val
        2150                2155                2160

Arg Phe Val Pro Gln Glu Met Gly Val His Thr Val Ser Val Lys
        2165                2170                2175

Tyr Arg Gly Gln His Val Thr Gly Ser Pro Phe Gln Phe Thr Val
        2180                2185                2190

Gly Pro Leu Gly Glu Gly Gly Ala His Lys Val Arg Ala Gly Gly
        2195                2200                2205
```

```
Pro Gly Leu Glu Arg Gly Glu Ala Gly Val Pro Ala Glu Phe Ser
    2210            2215            2220

Ile Trp Thr Arg Glu Ala Gly Ala Gly Gly Leu Ser Ile Ala Val
    2225            2230            2235

Glu Gly Pro Ser Lys Ala Glu Ile Thr Phe Asp Asp His Lys Asn
    2240            2245            2250

Gly Ser Cys Gly Val Ser Tyr Ile Ala Gln Glu Pro Gly Asn Tyr
    2255            2260            2265

Glu Val Ser Ile Lys Phe Asn Asp Glu His Ile Pro Glu Ser Pro
    2270            2275            2280

Tyr Leu Val Pro Val Ile Ala Pro Ser Asp Asp Ala Arg Arg Leu
    2285            2290            2295

Thr Val Met Ser Leu Gln Glu Ser Gly Leu Lys Val Asn Gln Pro
    2300            2305            2310

Ala Ser Phe Ala Ile Arg Leu Asn Gly Ala Lys Gly Lys Ile Asp
    2315            2320            2325

Ala Lys Val His Ser Pro Ser Gly Ala Val Glu Glu Cys His Val
    2330            2335            2340

Ser Glu Leu Glu Pro Asp Lys Tyr Ala Val Arg Phe Ile Pro His
    2345            2350            2355

Glu Asn Gly Val His Thr Ile Asp Val Lys Phe Asn Gly Ser His
    2360            2365            2370

Val Val Gly Ser Pro Phe Lys Val Arg Val Gly Glu Pro Gly Gln
    2375            2380            2385

Ala Gly Asn Pro Ala Leu Val Ser Ala Tyr Gly Thr Gly Leu Glu
    2390            2395            2400

Gly Gly Thr Thr Gly Ile Gln Ser Glu Phe Phe Ile Asn Thr Thr
    2405            2410            2415

Arg Ala Gly Pro Gly Thr Leu Ser Val Thr Ile Glu Gly Pro Ser
    2420            2425            2430

Lys Val Lys Met Asp Cys Gln Glu Thr Pro Glu Gly Tyr Lys Val
    2435            2440            2445

Met Tyr Thr Pro Met Ala Pro Gly Asn Tyr Leu Ile Ser Val Lys
    2450            2455            2460

Tyr Gly Gly Pro Asn His Ile Val Gly Ser Pro Phe Lys Ala Lys
    2465            2470            2475

Val Thr Gly Gln Arg Leu Val Ser Pro Gly Ser Ala Asn Glu Thr
    2480            2485            2490

Ser Ser Ile Leu Val Glu Ser Val Thr Arg Ser Ser Thr Glu Thr
    2495            2500            2505

Cys Tyr Ser Ala Ile Pro Lys Ala Ser Ser Asp Ala Ser Lys Val
    2510            2515            2520

Thr Ser Lys Gly Ala Gly Leu Ser Lys Ala Phe Val Gly Gln Lys
    2525            2530            2535

Ser Ser Phe Leu Val Asp Cys Ser Lys Ala Gly Ser Asn Met Leu
    2540            2545            2550

Leu Ile Gly Val His Gly Pro Thr Thr Pro Cys Glu Glu Val Ser
    2555            2560            2565

Met Lys His Val Gly Asn Gln Gln Tyr Asn Val Thr Tyr Val Val
    2570            2575            2580

Lys Glu Arg Gly Asp Tyr Val Leu Ala Val Lys Trp Gly Glu Glu
    2585            2590            2595
```

```
His Ile Pro Gly Ser Pro Phe His Val Thr Val
    2600                2605

<210> SEQ ID NO 40
<211> LENGTH: 9
<212> TYPE: PRT
<213> ORGANISM: Artificial Sequence
<220> FEATURE:
<223> OTHER INFORMATION: Synthetic: peptide

<400> SEQUENCE: 40

Ala Gly Val Ala Pro Leu Gln Val Lys
1               5

<210> SEQ ID NO 41
<211> LENGTH: 14
<212> TYPE: PRT
<213> ORGANISM: Artificial Sequence
<220> FEATURE:
<223> OTHER INFORMATION: Synthetic: peptide

<400> SEQUENCE: 41

Tyr Asn Glu Gln His Val Pro Gly Ser Pro Phe Thr Ala Arg
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Synthetic: peptide

<400> SEQUENCE: 42

Glu Arg Pro Leu Val Gly Val
1               5
```